United States Patent
Frankard et al.

(10) Patent No.: US 8,455,719 B2
(45) Date of Patent: Jun. 4, 2013

(54) METHOD FOR INCREASING SEED YIELD OR BIOMASS BY EXPRESSING RNA BINDING PROTEINS IN TRANSGENIC PLANTS

(75) Inventors: Valerie Frankard, Waterloo (BE); Christophe Reuzeau, La Chapelle Gonaguet (FR); Ana Isabel Sanz Molinero, Gentbrugge (BE)

(73) Assignee: CropDesign N.V., Zwijnaarde (BE)

( * ) Notice: Subject to any disclaimer, the term of this patent is extended or adjusted under 35 U.S.C. 154(b) by 1424 days.

(21) Appl. No.: 11/660,395

(22) PCT Filed: Aug. 16, 2005

(86) PCT No.: PCT/EP2005/054034
§ 371 (c)(1),
(2), (4) Date: Jan. 14, 2008

(87) PCT Pub. No.: WO2006/018432
PCT Pub. Date: Feb. 23, 2006

(65) Prior Publication Data
US 2008/0250534 A1 Oct. 9, 2008

Related U.S. Application Data

(60) Provisional application No. 60/602,680, filed on Aug. 19, 2004.

(30) Foreign Application Priority Data

Aug. 16, 2004 (EP) .................................... 04103926

(51) Int. Cl.
*C12N 15/82* (2006.01)
*C07H 21/04* (2006.01)
*A01H 5/00* (2006.01)

(52) U.S. Cl.
USPC ........... 800/290; 800/278; 800/287; 800/295; 800/298; 536/23.1; 536/23.6

(58) Field of Classification Search
None
See application file for complete search history.

(56) References Cited

U.S. PATENT DOCUMENTS 6,018,106 A 1/2000 Hunt et al.
2006/0150283 A1* 7/2006 Alexandrov et al. ......... 800/288

FOREIGN PATENT DOCUMENTS

| WO | WO-01/81599 A2 | 11/2001 |
| WO | WO-03/027299 A2 | 4/2003 |
| WO | WO-03/085115 A2 | 10/2003 |

OTHER PUBLICATIONS

Macknight et al. FCA, a gene controlling flowering time in *Arabidopsis*, encodes a protein containing RNA-binding domains. (1997) Cell; vol. 89; pp. 737-745.*
Suzuki et al. An RNA-binding protein, AtRBP1, is expressed in actively proliferative regions in *Arabidopsis thaliana*. (2000) Plant Cell Physiology; vol. 41; pp. 282-288.*
Lorkovic et al. Genome analysis: RNA recognition motif (RRM) and K homology (KH) domain RNA-binding proteins from the flowering plant *Arabidopsis thaliana*. (2002) Nucleic Acids Research; vol. 30; pp. 623-635.*
Schomburg et al. FPA, a gene involved in floral induction in *Arabidopsis*, encodes a protein containing RNA-Recognition motifs. (2001) The Plant Cell; vol. 13; pp. 1427-1436.*
GenBank Accession NM_129902; *Arabidopsis thaliana* RNA recognition motif (RRM)—containing protein (At2g43410) mRNA, complete cds. (2004); pp. 1-3.*
Mena et al. An endosperm-specific DOF protein from barley, highly conserved in wheat, binds to and activates transcription from the prolamin-box of a native B-hordein promoter in barley endosperm. (1998) The Plant Journal; vol. 16; pp. 53-62.*
Lee et al. Expansins: ever-expanding numbers and functions. (2001) Current Opinion in Plant Biology; vol. 4; pp. 527-532.*
Veylder et al. Functional analysis of cyclin-dependent kinase inhibitors of *Arabidopsis*. (2001) The Plant Cell; vol. 13; pp. 1653-1667.*
MacKnight, R., et al., "FCA, a Gene Controlling Flowering Time in *Arabidopsis*, Encodes a Protein Containing RNA-Binding Domains", Cell, 1997, vol. 89, pp. 737-745.
Lorković, Z., et al., "Genome Analysis: RNA Recognition Motif (RRM) and K Homology (KH) Domain RNA-binding Proteins from the Flowering Plant *Arabidopsis thaliana*", Nucleic Acids Research, 2002, vol. 30, No. 3, pp. 623-635.

* cited by examiner

*Primary Examiner* — Cathy Kingdon Worley
(74) *Attorney, Agent, or Firm* — Novak Druce Connolly Bove + Quigg LLP

(57) ABSTRACT

The invention concerns a method for improving growth characteristics of plants by increasing activity in a plant of an RNA-binding protein, which is: (i) a polypeptide having RNA-binding activity and comprising 2 or 3 RNA recognition motifs (RRMs) and a motif having at least 75% identity to motif I: PYEAAVVALPVVVKERLVRILRLGIATRYD (SEQ ID NO: 12) and/or a motif having at least 50% identity to motif II: RFDPFTGEPYKFDP (SEQ ID NO: 13); or (ii) an RBP1 polypeptide having (a) RNA-binding activity; (b) two RRM domains, (c) the following two motifs: (i) KIFVGGL (SEQ ID NO: 41); and (ii) RPRGFGF (SEQ ID NO: 42), allowing for up to three amino acid substitutions and any conservative change in the motifs; and (d) having at least 20% identity to SEQ ID NO: 15. Also provided is transgenic plants introduced with an RNA-binding protein-encoding nucleic acid having improved growth characteristics and constructs useful in the methods.

22 Claims, 27 Drawing Sheets

```
newriceCDS701homologue    MVRARDSIREILPVFSIQSALGTADSAPAIRPVAAASDLVRISSEKSRLD  50
rice                      --------------------------------------------------
maize                     --------------------------------------------------
CDS701Proteinprediction   -------------------------------------MSRLIEHHLANNK  13
BAC83046.1                ----------------------------------MEPTRRCVPGHLATAA  16 newriceCDS701homologue    LPVPLFFFVARG---GFQEKRGAASHGDYDEQGYWMGFFSLIPRASLALR  97
rice                      --------------------------------------------------
maize                     --------------------------------------------------
CDS701Proteinprediction   QDMKGTEVFVGG---LARTTTESKIHEVFSSCGEIVEIRLIKDQTGVPKG  60
BAC83046.1                AAAAASPFSPPPSLPLPSALMPPKKRRLFTPAPRHAATPPPPPPPPTPAV  66 newriceCDS701homologue    GRRVKGAEVFVGGLPRSVTERALREVGVLPRSQQVFSPCGEIVDLRIMKD 147
rice                      --------------------------------------------------
maize                     --------------------------------------------------
CDS701Proteinprediction   FCFVRFATKYAADKALKEKSGYVLDGKKLGVRPSVEQDTLFLGNLNKGWG 110
BAC83046.1                EPTLPIPPASTPPTPPQPSASTEPSTAPPPAVDDAAARSSSSSSPASAAA 116 newriceCDS701homologue    QNGISKVLCQLQGKRLAVDLSLDQDTLFFGNLCKGSDWGIEEFEELIRKV 197
rice                      --------------------------------------------------
maize                     --------------------------------------------------
CDS701Proteinprediction   AEEFESIVRQVFPDVVSVDLALLGDVQPG----QKQRNRGFAFVKFPSHA 156
BAC83046.1                ARKVRKVVKKVIVKKVVPKGTFAAR----------KAAAAAVAAAAAVS 155 newriceCDS701homologue    RPVVDLAMARNHDSSVGKRRLNRGFAFVRFSSHAVSQVKTAFVGNLPANV 247
rice                      ----------------------------------MAKVKTAFVGNLPANV  16
maize                     GSRTDFMLG-----DILHPAINWADKESHLDPDEMAKMKSAFIGNLPEDV  45
CDS701Proteinprediction   AAARAFRVGSQSDFLIDGKLHPSVQWAEEPDPNELAQIKAAFVRNVPPGA 206
BAC83046.1                GAAASSEAGGEAPTDEPASDQDGGVGNEQKLDESKPATDCNAVAVVEESV 205
                                                             .  .  :  ..

newriceCDS701homologue    TEEYLRKLFEHCGEVCYAVVRVAVSRKGQYPVGFVHFASRTWK------E 291
rice                      TEEYLRKLFEHCGEV----VRVAVSRKGQYPVGFVHFASRT--------E  54
maize                     NEEYLRKLFGQFGEV----VRVAISRKGQCPVAFVHFAKRS--------E  83
CDS701Proteinprediction   DEDYLKKLFQPFGNV----ERIALSRKGSSTIGFVYFDKRS--------D 244
BAC83046.1                CKEEEEVALVVGKGVEEEEAGMSERRKRMTMEVFVGGLHRDAKEDDVRAV 255
                          ::  . :    *        ::             * newriceCDS701homologue    LDNAIKEMDGETVRGPDRGATFRIQVSVARPVVENDKKRIREEVKTRRSN 341
rice                      LDNAIKEMDGETVRGPDRGATFRIQVSVARPVVENDKKRIREEVKTRRSN 104
maize                     LENAIEEMDGKTVRGPGRGPSFKIQVSVARPTADNDKKRSEEVVRTRRSN 133
CDS701Proteinprediction   LDNAIMALNEKTVQGPMGGPSCKLQVEVARPMDKN-RKRGREDPNMSSTI 293
BAC83046.1                FAKAGEITEVRMIMNPLAGKNKGYCFVRYRHAAQAKKAIAEFGNVKICGK 305
                          : :*      :  .  .*  *  .      *      . :    .

newriceCDS701homologue    VSTDKPDIISYGRRGHDSYDRQAKAPRLYNEVLIITNDKVDMITLFCQFSFL 391
rice                      VSTDKPDHSYGRRGHDSYDRQAKAPRLYN-------------------- 133
maize                     ASGDRRDYSHGRYGHDSLDRQVKAPRLSN--------------------Y 163
CDS701Proteinprediction   ESIISKLLK------DDPDVEMIRAPKSTAQ------------------L 318
BAC83046.1                LCRAAVPVGNDRIFLGNINKKWKKEDVIKQ------------------L 336
                                           .      .  . :

newriceCDS701homologue    QVSDTDPYEAAVVSLPSAVKELLLRILRLRIGTRYDVSNLYIRSLLVSIL 441
rice                      EVSDTDPYEAAVVSLPSAVKELLLRILRLRIGTRYD------------- 169
maize                     VADAADPYESAVNSLPSAVKEVLLRILRLRIGTRYD------------- 199
CDS701Proteinprediction   EMDYSDPYEAAVVALPVVVKERLVRILRLGIATRYD------------- 354
BAC83046.1                KKIGIENIDSVTLKSDSNNPVCNRGFAFLELETSDAR------------ 374
                              :  ::..             :   *  :  *    *
```

FIGURE 1

```
newriceCDS701homologue  LFQIDIHCIRSLNELPEKAAVAVLNQCSQFLISGADKHNKGDYFASLIAK  491
rice                    ---IDIHCIRSLNELPEKAAVAVLN---QFLISGADKHNKGDYFASLIAK  213
maize                   ---IDIHCVKSLDELPESSALAVLN---QFLISGGDKHNKGDYFASLVAK  243
CDS701Proteinprediction ---IDVESLTSLKILPQSAAISILD---QFMLSGADMQNKGGYLASLISK  398
BAC83046.1              ---MAYKKLSQKNAFGKGLNIRVAWAEPLNDPDEKDMQVKSIFVDGIPTS  421
                           :  . :  . .: ::      . * :*. :. .: :.

newriceCDS701homologue  -------ETFSSALRLQGSTYLPRNPEIQNKRFPH---------SSRYSS  525
rice                    YQA----ETFSSALRLQGSTYLPRNPGIQNKRFPHQDYEYTASGSSRYSS  259
maize                   HQA----ETFGLTHALHGTTYLSRNPEMHSKRYPHEDYDFVTPRSSRYDS  289
CDS701Proteinprediction QVEKLGPKQFDSRSRIEDVGLRVPEPDRFSTRVRLPDLDSYASRVPLPMP  448
BAC83046.1              WDHAQLKEIFKKHGKIESVVLSRDMPSAKRRDFAFINYITREAAISCLES  471
                                  : *       :..         *                  . .

newriceCDS701homologue  LGDYPS---SSYVDDPASSQSRNRRYDEYRPDLVRYPDSRSRQEEIVRIE  572
rice                    LGDYPS---SSYVDDPASSQSRNRRYDEYRPDLVRYPDSRSRQEEIVRIE  306
maize                   SAHHPS---TYYEDDPPVSESRVRRYAEERSTIVRSPEPRPRYDETD-IR  335
CDS701Proteinprediction RTDVYTSHYSAYLDPHILSGRMTAKRMEEASSHLQATSLLSSRVATRMEEA 498
BAC83046.1              FDKEEFSKNGSKVNIKVSLAKPAQQSKQTKEDHKSSITGEGKMKTSKIRY  521
                           .                 :        ::  :             :

newriceCDS701homologue  RYPEPRFAHEPRQDTGRHLDLGYVQERNSNIERSAQVAFSSREGGYLSAS  622
rice                    RYPEPRFAHEPRQDTGRHLDLGYVQERNSNIERSAQVAFSSREGGYLSAS  356
maize                   INPEPRLPYESRHNAEKHLDRRYIQEHSSNIERPAEEALLSRERRFLPAA  385
CDS701Proteinprediction GSTLQSLLSGGVTTRRMEEASPILQATLLPSGRVSRMDEASPNLQATWSP  548
BAC83046.1              PVQDYTHIYSGEKRPFSTLGDPYYPLRGHSCRRHEGSTYTTAASSYGALP  571
                                                         *      :          .

newriceCDS701homologue  RYNTN-IVPEFSSRSSAEYSTARQQV RFDPFTGEPYKFDP YTGEPIRPES  671
rice                    RYNTN-IVPEFSSRSSAEYSTARQQV RFDPFTGEPYKFDP YTGEPIRPES  405
maize                   GYMPNPGGSDFRSRSPAEYSAQRQQM RFDPFTGEPYKFXP FTGEPIRPDP  435
CDS701Proteinprediction SPTNDRIGLHSHITATADHQHTRPRI RFDPFTGEPYKFDP FTGEPIVPKS  598
BAC83046.1              PATAESSLPHYHDSN----------- RYPPHLGEAIKFSP TSAVLSKQAW  610
                          :     .                  *:  *.  **.  **  *       :.

newriceCDS701homologue  NPR--RSGSLY-- 680
rice                    NPR--RSGSLY-- 414
maize                   NPAPLRKPVIXSE 448
CDS701Proteinprediction SSH---HRSLY-- 606
BAC83046.1              QKM---------  613
```

FIGURE 1 (continued)

```
Translation of AK067725-Os-RBP1   (1) ----------------MEADSGKLFVGGISWETDEDRLREYFSRFGEVTEAVIMRDR
Translation of AK070544-Os-RBP1   (1) ----------------MEADAGKLFIGGISWDTNEDRLREYFDKYGEVVEAVIMRDR
Translation of NM_196957-Os-RBP1  (1) ----------------MESDQGKLFIGGISWETTEEKLRDHFAAYGDVSQAAVMRDK
NP_176143-At-RBP1                 (1) ----------------MDYDRYKLFVGGIAKETSEEALKQYFSRYGAVLEAVVAKEK
NP_567753-At-RBP1                 (1) MNPEEQKMESASDLGKLFIGGISWDTDEERLQEYFGKYGDLVEAVIMRDR
NP_974937-At-RBP1                 (1) ----------------MESDLGKLFIGGISWDTDEERLRDYFSNYGDVVEAVIMRDR
NP_193166-At-RBP1                 (1) ----------------MDSDQGKLFVGGISWETDEDKLREHFTNYGEVSQAIVMRDK
NP_850539-At-RBP1                 (1) ----------------MQSDNGKLFIGGISWDTNEERLKEYFSSFGEVIEAVILKDR
NP_180899-At-RBP1                 (1) ----------------MESDQGKLFIGGISWDTDENLLREYFSNFGEVLQVTVMREK
NP_974899-At-RBP1                 (1) ---------------------------------------------------------

51                                              100
Translation of AK067725-Os-RBP1  (42) NTGRARGFGFVVFTDAGVAERVTMDKHMIDGRMEAKKAVPRDDQSITSK
Translation of AK070544-Os-RBP1  (42) ATGRARGFGFIVFADPAVAERVIMEKHMIDGRMEAKKAVPRDDQHALSK
Translation of NM_196957-Os-RBP1 (42) LTGRPRGFGFVVFSDPSSVDAALVDPHTIDGRTYDVKRALSREEQQAAKA
NP_176143-At-RBP1                (42) VTGKPRGFGFVVRFAMDCDVVKALRDTHFTLGKPYDVRKAIRKHELYQQPF
NP_567753-At-RBP1                (51) TTGRARGFGFIVFADPSVAERVIMDKHIIDGRTYEAKKAVPRDDQQVLKR
NP_974937-At-RBP1                (42) ATGRARGFGFIVFADPCVSERVIMDKHIIDGRTYEAKKAVPRDDQQVLKR
NP_193166-At-RBP1                (42) LTGRPRGFGFVIFSDPSVLDRVLQEKHSIDTREYDVKRAMSREEQQVSGR
NP_850539-At-RBP1                (42) TTGRARGFGFVVFADPAVAEIVITEKHNIDGRLVEAKKAVPRDDQNMVNR
NP_180899-At-RBP1                (42) ATGRPRGFGFVAFSDPAVIDRVLQDKHHIDNRDVDVKRAMSREEQSPAGR
NP_974899-At-RBP1                 (1) ----------------MVEAKKAVPRDDHVVFNK 101                                             150
Translation of AK067725-Os-RBP1  (92) NNGS------SIGSPG--------------------PGRTRKIFVGGLASNVE
Translation of AK070544-Os-RBP1  (92) SGGS------AHGSPG--------------------PSRTKKIFVGGLASTVE
Translation of NM_196957-Os-RBP1 (92) ANPSAGGRHASGGGGGGGGAGGGGGGDAGGARTKKIFVGGLPSNLE
NP_176143-At-RBP1                (92) SMQFLERKVQQMNGGLREMS-------------SNGVTSRTKKIFVGGLSSNTE
NP_567753-At-RBP1               (101) HASPMHLISPSHGGNGG-------------------GARTKKIFVGGLPSSTE
NP_974937-At-RBP1                (92) HASPIHLMSPVHGGGG--------------------RTKKIFVGGLPSSTE
NP_193166-At-RBP1                (92) IGNLNTSRSSGG------------------------DAYNKTKKIFVGGLPPTLD
NP_850539-At-RBP1                (92) SNSSS-----IQGSPGG-------------------PGRTRKIFVGGLPSSVE
NP_180899-At-RBP1                (92) SGTFNASRNFDS------------------------GANVRTKKIFVGGLPPALIS
NP_974899-At-RBP1                (19) SNSS------LQGSPG--------------------PSNSKKIFVGGLASSVE
```

FIGURE 3

```
                                                                    200
Translation of AK067725-Os-RBP1    (120) VETRRYEQFGVTDVVVYIHNQIPRGTGITYSEDAVDKALHKNE
Translation of AK070544-Os-RBP1    (120) ADTRKYEQFGTTDVVVYIHNQIPRGTGITYSEDAVDKALFKTE
Translation of NM_196957-Os-RBP1   (142) DETRQYQTYGVTDVVVYIQNQIPRGTGITFAEDAVDRVLHKTE
              NP_176143-At-RBP1    (134) EETKSYFERFGRTTDVVVYIHGVNIPRGTGVTYSEDSEVVMQSNE
              NP_567753-At-RBP1    (136) AETKNYFDQFGTTADVVVYIHNQIPRGTGITFSEESVDMVLHKTE
              NP_974937-At-RBP1    (124) EETKNYFDQFGTTADVVVYIHNQIPRGTGITFSDDAVDRVLHKTE
              NP_193166-At-RBP1    (124) EETRQYEQFGTTTDVVVYIHNQAPRGTGVSFSEDAVDSVLHKTE
              NP_850539-At-RBP1    (122) SDTKTYFEQFGTTTDVVVYIHNQIPRGTGITYSEEAVEKVLLKTE
              NP_180899-At-RBP1    (124) DETRAYFETYGPVSDAVMLIQTQIPRGTGVSFSEDSVDLVLHKTE
              NP_974899-At-RBP1    (47)  AETKKYFAQFGMTDVVVYIHRQIPRGTGISYSEEAVDKVLQKTE 250
Translation of AK067725-Os-RBP1    (170) EINGKMYEVKRAVPKEQSPGPA--ARSPAGG--QNYAMSRVHSFLNGENQ
Translation of AK070544-Os-RBP1    (170) EINGKMYEVKRAVPKELSPGPS--MRSPVGG--FNYAVNRANMFLNGYTQ
Translation of NM_196957-Os-RBP1   (192) DLSGKMYEVKPALREANPGSGSGGRSMGGGGGYQSNNGPNSNSGGYDS
              NP_176143-At-RBP1    (184) ELSDYRVEVKRAIPKE-----------------G--IQSNNGNAVNIPP
              NP_567753-At-RBP1    (186) EINGKMYEVKRAVPKELSSTTP--NRSPLIGYGNNYGVVPNRSSANSYFN
              NP_974937-At-RBP1    (174) EINGKLYEVKRAVPKEISPVSN--IRSPLAS-GVNYGGGSNRMPANSYFN
              NP_193166-At-RBP1    (174) DLSGQYEVKRALLKDAMPGGG--GRSMGGGGSGGYQGYGGNESS---YDG
              NP_850539-At-RBP1    (172) EINGKMEVKRAVPKELSPGPS--RSPLGAG--YSYGVNRVNNLLNGYAQ
              NP_180899-At-RBP1    (174) DINGKQYEVKRALFKDAMPGIASGGGRGSGGAGGFPGYGGSGSG--YEG
              NP_974899-At-RBP1    (97)  EINGKMEVKVLAVPKDMALMTMRNQMN------VNSFGTSRISSLLNEYTQ 300
Translation of AK067725-Os-RBP1    (216) GYNPNPIGGYGMRVDG--RYGLLT--GARNGFSSFFGPYGMGMNSESGMNAN
Translation of AK070544-Os-RBP1    (216) GYNPSPVGGYGMRMDA--RFGLLS--GGRSSYPSFGGYGVGMNFDPGMNPA
 ranslation of NM_196957-Os-RBP1   (242) RGDASRYGQAQQGSGG--YPGY--GAGGYGAGTV YGYGHANPGTAYGN
              NP_176143-At-RBP1    (214) SYSSFQATPYVPEQNG------YGMVLQFPPVFFYHHNVQAVQYPYGY
              NP_567753-At-RBP1    (234) SFPPG--YNNMNLGSAG--RFSPIG--SGRNAFSSFGLGLMQELNLNSN---
              NP_974937-At-RBP1    (221) NFAPGPGFYNSLGPVGRRFSPVIGSGRNAVSAFGLGLMHDLSLNLNPSCD
              NP_193166-At-RBP1    (220) RMDSNRFLQHQSVGNG---LPSY--GSSGYGA--GYGNG--SNGAGYC-
              NP_850539-At-RBP1    (218) GFNPAAVGGYGLRMDG--RFSPVG-AGRSGFANYSSGYGMNVNFDQGLPTG
              NP_180899-At-RBP1    (222) RVDSNRYMQPQNTGSG---YPPY--GGSGYGT---GYGYG--SNGVGYG-
              NP_974899-At-RBP1    (142) GFSPSPISGYGVKPEVRYSPAVG--NRGGFSPFGHGYGIELNFEPNQTQN
```

FIGURE 3(continued)

```
                                                301                                                350
Translation of AK067725-Os-RBP1   (264)  FGANSSFVNNSN-GRQIGSFYNGSS-NRLGSPIGYVGLN-DDSGSLLSSM
Translation of AK070544-Os-RBP1   (264)  IGGSSSFNNSLQYGRQLNPYYSGNS-GRYNSWVSYGGVN-DSTGSVFNSL
Translation of NM_196957-Os-RBP1  (287)  YCAGGFGGVPAGYG---GHYGNPM----APGGYQGGP------PGA
              NP_176143-At-RBP1   (257)  QFTAQVANVSWN--------------NPIMQPTGFYCAP--------
              NP_567753-At-RBP1   (277)  FDGNTLGYSRIP----GNQYFNSASPNRYNSPIGYNRGD-----SAYNPS
              NP_974937-At-RBP1   (271)  GTSSTFGYNRIP----SNPYENGASPNRYTSPIGHNRTE-----SPYNSN
              NP_193166-At-RBP1   (259)  -AYGGYTGSAGGYGAGATAGYGATN----IPGAGYGSST------GVA
              NP_850539-At-RBP1   (266)  FTGGTNYNGNVDYGRGMSPYYIGNT-NRFGPAVGYEGGNGGGNSSFFSSV
              NP_180899-At-RBP1   (261)  -GFGGYGNPAG-----APYGNPS----VPGAGFGS----------G
              NP_974899--At-RBP1  (190)  YGSGSSGGFGRPFSPGYAASLGRFGSQMESGGASVGNGS-------VLNAAP 351                                                400
Translation of AK067725-Os-RBP1   (311)  SRNVWGNEN-LNYPNNPTNMSS--FAPSGTGG-----QMGITSDGINWGG-
Translation of AK070544-Os-RBP1   (312)  ARNLWGNSG-LSYSSNSASSNS--FMSSANGG-----LGGIGNNNVNWGNP
Translation of NM_196957-Os-RBP1  (321)  NRGPWGGQAPSGYG----------TGS----------YGG
              NP_176143-At-RBP1   (282)  PHPTPPPTNNLG-------------------------
              NP_567753-At-RBP1   (318)  NRDLWGNRS-----------DSSG-------------
              NP_974937-At-RBP1   (312)  NRDLWGNRT-----------DTAG-------------
              NP_193166-At-RBP1   (296)  PRNSWDTPASSGYG------NPG---------YGS
              NP_850539-At-RBP1   (315)  TRNLWGNNGGLNYNNNNTNSNTYMGGSSGNNTLSGPFGNSGVNWGA-
              NP_180899-At-RBP1   (287)  PRSSWGAQAPSGYG------MVG---------YGN
              NP_974899--At-RBP1  (235)  KMHLWGNGG-LGYMS-----NS---

401                                                450
Translation of AK067725-Os-RBP1   (353)  PTPGHGMGNISSLGLANLGRGAG--DSFGLPSGSYGRSNATGTIGEPFS-
Translation of AK070544-Os-RBP1   (355)  PVPAQGANAGPGYGSGNFGYGSSE-TNFGLGTNAYGR-NAGSGVVNTFN-
Translation of NM_196957-Os-RBP1  (341)  NAGYAAWNNSSAGGNAPTSQAQAGAGTGYGSQGYGYGG-YGGDASYGNHGG
              NP_176143-At-RBP1   (294)  --YIQYMNGFDLSGTNISGYNPLAWPVTGDAAGALIHQFVDLKLDVHSQA
              NP_567753-At-RBP1   (331)  --PGWNLGVSVGNMRGNWGLSS------VVSDNNGYGRSYCAGSGLSGLSF
              NP_974937-At-RBP1   (325)  --PGWNLNVSNGNMRGNWGLPSS--SAVSNDNNGFGRNYGTSSGLS--
              NP_193166-At-RBP1   (316)  GAAHSGYG----VPGAAPPTQS---PSGYSNQGYGYGGYGSDSGYGNQAA
              NP_850539-At-RBP1   (364)  --PGGGNNAVSNEM-VKFGYGGNGESGFGLGTGGYAARNPGANKAAPSSS
              NP_180899-At-RBP1   (307)  AAPWGGSG----GPGSAVMGQAG-ASAGYGSQGYGYG---GMDSSYGTPSA
              NP_974899--At-RBP1  (251)  --PISRSSFSGMSGMSSLGSIGDNWGTVARARSSYHGERGGVGLEAMRG-
```

FIGURE 3(continued)

```
                                              451                                                       500
Translation of AK067725-Os-RBP1      (400)    -APPNAYEVANADTYGSS-------SIYGDSTWRFTSSEID--------MP
Translation of AK070544-Os-RBP1      (402)    -QSTNGYGRNFGDSSGGGGGGGSIYGDTTWRSGSSELDG--------TS
Translation of NM_196957-Os-RBP1     (390)    YGGYGGRGDGAGNPAAGG-------GSGYCAGYGSGNGGSGYP------NA
              NP_176143-At-RBP1      (342)    HQRMNGGNMGIPLQNGTYI-------------------------------
              NP_567753-At-RBP1      (374)    AGNTNGFDGSIGELYRGS-------SVYSDSTWQSMPHHQSSNELDGLSR
              NP_974937-At-RBP1      (367)    SSPFNGFEGSIGELYRGG-------SVYSDSTWQQQLPSQSSHELDNLSR
              NP_193166-At-RBP1      (360)    YGVVGGRPSGGGSNNPGS-------GGYMGGGYGDGS----------W
              NP_850539-At-RBP1      (411)    FSSASATNNTGYDTAGLAEFYGNGAVYSDPTWRSPTPETEG-------PA
              NP_180899-At-RBP1      (350)    YGAVGGR-SGNMPNNHGG-------GGYADALDGSGG------------Y
              NP_974899-At-RBP1      (298)    -VHVGGYSSGSSILEADS-------LYSDSMWLSLP---AK--------A 501                                                       550
Translation of AK067725-Os-RBP1      (435)    PFGNDLGN--VDPDIKSNIP-ASYMGNYTVNNQTSRGITS----------
Translation of AK070544-Os-RBP1      (444)    PFGYGLGN--AASDVTAKNS-AGYMGH-----------------------
Translation of NM_196957-Os-RBP1     (428)    WADPSQGGFGASVNGVSEGQSNYGSYGGVQPRVAQ---------------
              NP_176143-At-RBP1      (361)    --------------------------------------------------
              NP_567753-At-RBP1      (418)    SYGFGIDN--VGSDPSANAS-EGYSGNYNVGNRQTHRGIEA---------
              NP_974937-At-RBP1      (411)    AYGYDIDN--VGSDPSANDP-ETYNGSYNVGNRQTNRGNKKIHLNKTCNL
              NP_193166-At-RBP1      (391)    RSDPSQ----------------GYGGGYNDGQGRGQ--------------
              NP_850539-At-RBP1      (454)    PFSYGIGGGVPSSDVSARSSSPGYVGSYVNKRQPNRGEPSR---------
              NP_180899-At-RBP1      (380)    GNHQGNNG--------------QAGYGGYGSGRQAQQQ------------
              NP_974899-At-RBP1      (329)    EEGLGMGP-----LDFMS---R------GPAGYINRQPNGGIAA------

551
Translation of AK067725-Os-RBP1      (473)    ---
Translation of AK070544-Os-RBP1      (468)    ---
Translation of NM_196957-Os-RBP1     (465)    ---
              NP_176143-At-RBP1      (361)    ---
              NP_567753-At-RBP1      (456)    ---
              NP_974937-At-RBP1      (458)    DTF
              NP_193166-At-RBP1      (412)    ---
              NP_850539-At-RBP1      (496)    ---
              NP_180899-At-RBP1      (405)    ---
              NP_974899-At-RBP1      (359)    ---
```

FIGURE 3(continued)

seq id no 01: *Nicotiana tabacum* RNA-binding protein DNA
CCACGCGTCCGCTTAGGGTTCCAAATTGCTCTAAATTCCCGCGGATTGAGAGTTCATTGGAGAC
TTCCATTGTTCCCAGCGGCTAAGATGAGCCGGTTGATTGAGCATCACCTAGCAAATAATAAACA
GGACATGAAAGGGACAGAGGTTTTTGTTGGTGGTTTGGCCCGTACTACTACTGAAAGCAAAATT
CATGAGGTATTTTCTTCATGTGGTGAGATTGTGGAAATACGGTTGATAAAAGACCAGACAGGCG
TTCCTAAGGGGTTTTGCTTTGTACGATTTGCAACAAAATATGCTGCTGACAAAGCTCTGAAGGA
AAAATCTGGATATGTGCTGGATGGGAAGAAACTCGGGGTTCGCCCCTCAGTTGAGCAGGACACT
TTATTTCTTGGAAATCTTAACAAAGGTTGGGGTGCGGAGGAATTTGAGAGTATTGTGCGCCAGG
TTTTTCCAGATGTTGTATCTGTTGATCTTGCACTTCTTGGAGATGTCCAACCTGGTCAGAAGCA
ACGGAATCGGGGTTTTGCTTTCGTGAAATTCCCATCTCATGCTGCTGCGGCTCGTGCTTTTCGG
GTAGGCTCCCAATCTGATTTTCTCATTGATGGCAAGTTACATCCATCTGTACAGTGGGCTGAGG
AACCTGATCCCAATGAACTTGCTCAGATCAAAGCAGCCTTCGTTAGAAATGTACCTCCTGGTGC
TGATGAAGATTACTTGAAGAAGCTCTTTCAGCCCTTTGGCAATGTAGAGAGGATAGCTCTATCC
AGGAAAGGTAGCTCCACCATTGGATTCGTTTACTTCGATAAGCGATCTGATCTTGACAATGCTA
TTATGGCGTTGAATGAGAAAACTGTACAAGGGCCAATGGGAGGTCCCTCATGCAAGCTTCAGGT
CGAAGTTGCTAGGCCAATGGACAAGAACAGGAAACGAGGTCGTGAGGATCCAAACATGTCCAGT
ACCATTGAGAGTCATTCCAAGCTTTTGAAGGATGATCCAGATGTTGAGATGATTAGGGCTCCTA
AATCAACTGCTCAACTGGAGATGGATTATTCGGATCCTTATGAAGCTGCTGTAGTTGCATTACC
TGTGGTTGTCAAGGAGCGTTTAGTTCGGATCTTGCGGCTTGGTATTGCTACTAGATATGATATA
GATGTTGAAAGTTTAACCAGTCTTAAGATATTGCCCCAGTCAGCTGCCATATCTATTCTTGACC
AGTTCATGTTGTCTGGAGCTGATATGCAGAACAAGGGAGGATATCTAGCTTCATTAATTTCTAA
GCAGGTTGAAAAACTGGGACCGAAACAATTCGATAGTAGGTCAAGGATAGAAGATGTTGGCTTG
AGGGTGCCAGAACCAGACAGGTTCTCTACAAGAGTTCGTTTGCCAGATCTAGATTCATATGCCT
CACGAGTACCCTTGCCCATGCCTAGGACTGATGTTTACACATCTCACTATTCAGCGTATTTAGA
TCCCCATCTGTCTGGTCGGATGACAGCAAAGAGGATGGAGGAAGCAAGTTCCCATTTGCAGGCG
ACTTCACTTCTGTCTAGTCGGGTGGCAACGAGGATGGAGGAGGCAGGTTCCACTTTGCAGTCGC
TCCTATCTGGTGGGGTGACGACAAGAAGGATGGAGGAAGCAAGTCCGATTTTGCAGGCAACACT
CCTTCCATCTGGTCGGGTATCAAGGATGGATGAAGCAAGTCCCAATTTGCAGGCAACATGGAGC
CCTTCTCCTACTAATGACAGAATTGGACTTCATTCACACATTACCGCAACTGCTGATCATCAAC
ATACTCGACCACGGATCAGGTTTGATCCCTTCACTGGTGAGCCATACAAATTTGACCCCTTCAC
TGGCGAGCCAATTGTTCCCAAGAGCTCAAGTCATCATCGAAGCCTGTACTGAACGTTCTGAGCA
TTCTAATTTACAAATGGCTTATTGCCAAACCTATGTAACATAATGATGCGTATTTTTGTTCATC
CGCAGCTGTAAAATAGTAGCTGTTAGCAGGATTATTTGGTTATGTTTCTCATTGACTTCATTGA
TTGCGAAGGTGCATTTGGAATCTCGGCAATCACAATTTATAGCCGGTGCA seq id no 02: *Nicotiana tabacum* RNA-binding protein
MSRLIEHHLANNKQDMKGTEVFVGGLARTTTESKIHEVFSSCGEIVEIRLIKDQTGVPKGFCFV
RFATKYAADKALKEKSGYVLDGKKLGVRPSVEQDTLFLGNLNKGWAEEFESIVRQVFPDVVSV
DLALLGDVQPGQKQRNRGFAFVKFPSHAAAARAFRVGSQSDFLIDGKLHPSVQWAEEPDPNELA
QIKAAFVRNVPPGADEDYLKKLFQPFGNVERIALSRKGSSTIGFVYFDKRSDLDNAIMALNEKT
VQGPMGGPSCKLQVEVARPMDKNRKRGREDPNMSSTIESHSKLLKDDPDVEMIRAPKSTAQLEM
DYSDPYEAAVVALPVVVKERLVRILRLGIATRYDIDVESLTSLKILPQSAAISILDQFMLSGAD
MQNKGGYLASLISKQVEKLGPKQFDSRSRIEDVGLRVPEPDRFSTRVRLPDLDSYASRVPLPMP
RTDVYTSHYSAYLDPHLSGRMTAKRMEEASSHLQATSLLSSRVATRMEEAGSTLQSLLSGGVTT
RRMEEASPILQATLLPSGRVSRMDEASPNLQATWSPSPTNDRIGLHSHITATADHQHTRPRIRF
DPFTGEPYKFDPFTGEPIVPKSSSHHRSLY

FIGURE 6

**seq id no 03: *Oryza sativa* RNA-binding protein DNA**
ATGGTGCGTGCTCGAGACTCAATCCGCGAAATCCTCCCTGTTTTTTCGATTCAATCCGCCCTGG
GGACGGCGGATTCGGCGCCGGCGATCCGGCCGGTCGCCGCCGCGTCCGATTTGGTGCGGATTTC
GTCGGAGAAATCGCGTCTTGACCTTCCTGTGCCTCTTTTTTTTTTGTTGCTCGTGGGGGATTT
CAGGAGAAGAGGGGGGCGGCGTCGCATGGCGACTACGACGAGCAAGGTTATTGGATGGGTTTCT
TCTCTTTGATACCTCGAGCGAGTCTTGCGTTGCGTGGGTGAAAGGCGCCGAGGTGTTCGTCGGC
GGGTTGCCGCGGTCGGTGACGGAGCGGGCGCTCCGAGAGGTTGGTGTTCTTCCGAGAGGTGTAA
TCTCAACAGGTATTTTCTCCTTGTGGAGAGATTGTTGATTTGCGGATAATGAAAGATCAGAATG
GCATTTCAAAGTGGTTCTCTGCCAGCTTCAAGGAAAGAGACTTGCTGTTGATCTTTCGTTGGAT
CAAGATACACTCTTCTTTGGGAATCTTTGCAAAGGTAGTCAGACTGGGGCATCGAAGAATTTGA
AGAATTGATTCGCAAGGTAAGACCTGTAGGTTGACCTTGCAATGGCTCGAAACCATGACTCTTC
AGTTGGGAAAAGACGTCTAAATCGAGGCTTTGCATTTGTGCGATTTTCTTCTCATGCAGTAAGT
GTTGACATGATAACCCTTTTCTGCCAATTTTCTTTTTTGCAGGTGTCTGATACGGACCCCTATG
AAGCAGCTGTTGTTTCACTACCTTCAGCCGTCAAGGAACTCCTACTTCGTATTCTACGTCTTAG
AATTGGCACTCGATATGATGTAAGTAATCTGTACATAAGGTCTCTACTTGTGCAGCTCCAGGTC
ATCTGCTGAATACTCTACTGCTCGCCAACAAGTAAGGTTTGATCCATTCACAGGGGAACCATAC
AAGTTTGATCCCTACACCGGTGAACCCATCAGGCCAGAATCGAACCCACGTCGCTCAGGAAGCT
TATACTGACTTTGATTGATTGAAGCAACAGTTTGGATATGGTAGATTAGATTTACATCCCTGAA
CCAAAAGGACCATAT

**seq id no 04: *Oryza sativa* RNA-binding protein**
MVRARDSIREILPVFSIQSALGTADSAPAIRPVAAASDLVRISSEKSRLDLPVPLFFFVARGGF
QEKRGAASHGDYDEQGYWMGFFSLIPRASLALRGRRVKGAEVFVGGLPRSVTERALREVGVLPR
SQQVFSPCGEIVDLRIMKDQNGISKVLCQLQGKRLAVDLSLDQDTLFFGNLCKGSDWGIEEFEE
LIRKVRPVVDLAMARNHDSSVGKRRLNRGFAFVRFSSHAVSQVKTAFVGNLPANVTEEYLRKLF
EHCGEVCYAVVRVAVSRKGQYPVGFVHFASRTWKELDNAIKEMDGETVRGPDRGATFRIQVSVA
RPVVENDKKRIREEVKTRRSNVSTDKPDHSYGRRGHDSYDRQAKAPRLYNEVLHTNDKVDMITL
FCQFSFLQVSDTDPYEAAVVSLPSAVKELLLRILRLRIGTRYDVSNLYIRSLLVSILLFQIDIH
CIRSLNELPEKAAVAVLNQCSQFLISGADKHNKGDYFASLIAKETFSSALRLQGSTYLPRNPEI
QNKRFPHSSRYSSLGDYPSSSYVDDPASSQSRNRRYDEYRPDLVRYPDSRSRQEEIVRIERYPE
PRFAHEPRQDTGRHLDLGYVQERNSNIERSAQVAFSSREGGYLSASRYNTNIVPEFSSRSSAEY
STARQQVRFDPFTGEPYKFDPYTGEPIRPESNPRRSGSLY

**seq id no 05: *Zea mays* RNA-binding protein DNA (AY105295)**
TCTAGCTGTGTTCTTGTGGCTGTGAATTATATCTCCCATGCTGATACTTGATTCCCTTATCTT
TGCTTCATTACTACACCACAGTAATTTGGATCTGCCATTATGTTACTATGTAACTCTCATTTGA
TATCAATCACAGCTGCCACATACAAAATACAAGTATGTTTATCTAGATAAGATCTTGATTCATC
AATCACCACTGATCTGAGTTTTCGCCACTGCGATGCGAGGAAAAGACAGATATCTAATAACATC
TTGGTGAAGATGTTCTTAGGTCCTTTGCTTTCTCTTCAAGTCAGCTTCCTTTGATTTCATTCCT
CAAACTATCAATCACAGGCTGCAGCACGTGTAATCCGCATCGGTTCAAGAACAGATTTCATGCT
TGGTGATATTTTGCATCCTGCGATAAATTGGGCTGATAAAGAGTCTCATCTGGATCCTGATGAA
ATGGCCAAGATGAAGTCTGCTTTTATTGGTAACCTGCCAGAAGATGTTAATGAGGAGTACTTGA
GAAAGCTTTTTGGACAGTTCGGTGAGGTAGTACGGGTTGCTATCTCAAGAAAGGACAATGTCC
AGTTGCTTTTGTTCACTTCGCCAAACGTTCAGAGCTTGAGAATGCTATAGAAGAAATGGATGGT

FIGURE 6 (continued)

```
AAAACGGTGAGAGGACCTGGTCGAGGGCCGTCTTTCAAGATCCAGGTGTCAGTTGCTCGACCTA
CGGCAGACAACGACAAGAAGCGATCTCGTGAAGAAGTGAGAACTAGAAGATCAAATGCATCAGG
AGATAGGCGAGATTATTCTCATGGAAGATATGGACACGATTCACTTGATCGTCAAGTGAAAGCT
CCAAGATTATCTAATTATGTGGCCGATGCTGCTGACCCCTATGAATCAGCTGTTAATTCATTAC
CTTCAGCTGTCAAGGAAGTCTTGCTTCGAATTCTACGTCTAAGAATTGGTACTCGATATGATAT
TGATATCCATTGTGTTAAAAGCCTTGATGAGCTTCCTGAGTCATCTGCTCTTGCTGTCCTTAAT
CAGTTTTTGATATCAGGTGGAGACAAACACAACAAGGAGATTATTTTGCATCGTTGGTTGCTA
AGCACCAGGCTGAGACCTTTGGCTTAACACATGCATTACACGGTACCACTTATTTGTCAAGAAA
TCCGGAAATGCATAGCAAGCGATACCCACATGAAGATTATGATTTTGTGACACCCAGGAGCAGT
AGGTACGATTCGTCAGCCCATCATCCTTCAACATACTACGAAGACGATCCACCAGTGTCTGAGT
CAAGGGTTAGAAGATATGCTGAAGAAAGGTCCACCATTGTAAGAAGCCCAGAACCACGTCCGCG
ATATGACGAAACAGACATAAGAATAAACCCAGAACCAAGATTACCATATGAATCAAGACACAAC
GCCGAAAAGCATCTCGATCGAAGATACATACAAGAGCATAGTTCAAATATTGAAAGACCAGCTG
AAGAAGCTCTCCTTTCTAGGGAAAGGAGATTTCTGCCTGCTGCAGGGTACATGCCGAACCCAGG
CGGCTCGGATTTCCGCTCCAGGTCGCCCGCCGAATATTCAGCACAACGCCAACAAATGAGGTTT
GATCCATTCACAGGTGAACCTTACAAGTTTGNACCCTTCACAGGGGAGCCCATCAGGCCAGATC
CGAACCCAGCGCCGCTCAGGAAGCCTGTAATTGANTCAGAATAAGTTTGGAAGCCGANAATGCC
AGATTAAGAACCCTGAAANCAAAGCNAAGA
``` seq id no 06: Zea mays RNA-binding protein (AY105295)
```
GSRTDFMLGDILHPAINWADKESHLDPDEMAKMKSAFIGNLPEDVNEEYLRKLFGQFGEVVRVA
ISRKGQCPVAFVHFAKRSELENAIEEMDGKTVRGPGRGPSFKIQVSVARPTADNDKKRSREEVR
TRRSNASGDRRDYSHGRYGHDSLDRQVKAPRLSNYVADAADPYESAVNSLPSAVKEVLLRILRL
RIGTRYDIDIHCVKSLDELPESSALAVLNQFLISGGDKHNKGDYFASLVAKHQAETFGLTHALH
GTTYLSRNPEMHSKRYPHEDYDFVTPRSSRYDSSAHHPSTYYEDDPPVSESRVRRYAEERSTIV
RSPEPRPRYDETDIRINPEPRLPYESRHNAEKHLDRRYIQEHSSNIERPAEEALLSRERRFLPA
AGYMPNPGGSDFRSRSPAEYSAQRQQMRFDPFTGEPYKFXPFTGEPIRPDPNPAPLRKPVIXSE
``` seq id no 07: Oryza sativa RNA-binding protein DNA (AK059444)
```
ATCGATCACAGGCTGCAGCACGCGTACTTCGTATTGGTTCCAGAACAGATTTTCTGCTTGGTGG
ATTGCATCCTTCAATAAATTGGGCTGAGAAGGAGTCTCATGTAGATGAGGACGAAATGGCCAAG
GTTAAGACAGCTTTCGTTGGAAATTTACCAGCAAATGTTACAGAGGAGTATTTAAGAAAGCTTT
TTGAACATTGTGGAGAGGTAGTACGGGTTGCAGTCTCAAGGAAAGGACAATATCCAGTTGGATT
TGTCCACTTTGCCAGTCGTACAGAGCTCGACAATGCAATAAAAGAAATGGATGGTGAAACAGTG
AGAGGACCTGACCGAGGGGCAACTTTCAGGATCCAGGTCTCAGTTGCTCGGCCTGTGGTAGAGA
ACGATAAAAGAGAATTCGTGAAGAAGTGAAAACTAGAAGATCAAACGTATCAACAGACAAGCC
GGACCATTCTTATGGAAGACGTGGACATGATTCATATGATCGTCAAGCAAAAGCTCCAAGGCTA
TATAATGAGGTGTCTGATACGGACCCCTATGAAGCAGCTGTTGTTTCACTACCTTCAGCCGTCA
AGGAACTCCTACTTCGTATTCTACGTCTTAGAATTGGCACTCGATATGATATAGACATTCATTG
CATAAGGAGTCTTAATGAACTTCCTGAAAAGGCTGCAGTTGCTGTCCTTAATCAGTTTTTGATA
TCAGGTGCAGATAAACACAATAAAGGAGACTATTTCGCTTCATTAATTGCTAAGTACCAGGCTG
AGACATTTAGCTCAGCACTAAGATTGCAGGGTTCTACTTATTTGCCAAGAAATCCTGGAATACA
GAACAAGAGATTCCCACATCAAGATTACGAGTACACAGCATCCGGGAGTAGTAGATACAGTTCC
TTAGGTGATTATCCTTCCTCATCTTATGTGGATGATCCCGCATCATCTCAGTCAAGGAATAGAA
```

GGTATGATGAATACAGACCTGATCTTGTAAGATATCCAGATTCAAGATCACGGCAAGAGGAAAT
AGTCCGCATTGAAAGATATCCAGAACCAAGATTTGCACATGAACCAAGACAGGATACTGGAAGG
CATCTCGATCTAGGGTACGTACAAGAACGGAATTCGAATATTGAGAGATCAGCTCAAGTAGCTT
TTTCATCTAGGGAAGGAGGATACTTATCTGCTTCAAGGTACAACACAAACATAGTCCCAGAATT
CAGCTCCAGGTCATCTGCTGAATACTCTACTGCTCGCCAACAAGTAAGGTTTGATCCATTCACA
GGGGAACCATACAAGTTTGATCCCTACACCGGTGAACCCATCAGGCCAGAATCGAACCCACGTC
GCTCAGGAAGCTTATACTGACTTTGATTGATTGAAGCAACAGTTTGGATATGGTAGATTAGATT
TACATCCCTGAACCAAAAGGACCATATACTGCTCTTGCATGTTGTAAACCTAGTGTATTTGATG
TGCCTCAGCATTGTAATGTTAGAAATCCATTTTCATCCATGTCACTGGAAAACTATGGTTGAAA
CAACAGTAATAAGTTCTATCATTTATGATGGCATCTGATGATATGAATTAGGGAAAACTAAGC

**seq id no 08: *Oryza sativa* RNA-binding protein (AK059444)**
MAKVKTAFVGNLPANVTEEYLRKLFEHCGEVVRVAVSRKGQYPVGFVHFASRTELDNAIKEMDG
ETVRGPDRGATFRIQVSVARPVVENDKKRIREEVKTRRSNVSTDKPDHSYGRRGHDSYDRQAKA
PRLYNEVSDTDPYEAAVVSLPSAVKELLLRILRLRIGTRYDIDIHCIRSLNELPEKAAVAVLNQ
FLISGADKHNKGDYFASLIAKYQAETFSSALRLQGSTYLPRNPGIQNKRFPHQDYEYTASGSSR
YSSLGDYPSSSYVDDPASSQSRNRRYDEYRPDLVRYPDSRSRQEEIVRIERYPEPRFAHEPRQD
TGRHLDLGYVQERNSNIERSAQVAFSSREGGYLSASRYNTNIVPEFSSRSSAEYSTARQQVRFD
PFTGEPYKFDPYTGEPIRPESNPRRSGSLY

**seq id no 09: *Oryza sativa* RNA-binding protein DNA (BAC83046.1)**
ATGGAACCGACGCGCCGTTGCGTCCCCGGCCATCTCGCCACCGCCGCCGCCGCCGCCGCCGCCT
CGCCGTTCTCCCCGCCGCCGTCGCTGCCGCTGCCGTCCGCGCTCATGCCCCCCAAGAAGCGCCG
CCTCTTCACGCCCGCCCCTCGCCACGCCGCCACCCCGCCACCACCACCACCTCCCCCCACCCCC
GCCGTCGAGCCCACCCTACCAATCCCCCCGCCTCGACACCGCCGACGCCGCCTCAGCCCTCCG
CCTCCACGGAGCCCTCGACGGCGCCGCCTCCCGCTGTCGACGACGCGGCGGCGAGGTCGTCGTC
GTCGTCGTCGCCGGCGTCGGCGGCGGCGGCGCGGAAGGTTCGGAAAGTGGTTAAGAAGGTCATC
GTCAAGAAGGTCGTCCCCAAGGGCACGTTCGCCGCTCGGAAGGCCGCGGCGGCGGCGGTTGCTG
CTGCTGCGGCGGTCTCCGGAGCAGCAGCATCATCGGAGGCAGGGGGAGAAGCCCCAACCGACGA
GCCAGCAAGTGATCAGGACGGCGGAGTTGGGAATGAGCAAAAATTGGATGAATCCAAACCTGCC
ACGGATTGCAATGCCGTTGCGGTGGTGGAAGAATCGGTGTGTAAGGAGGAGGAGGAGGTGGCCT
TAGTGGTGGGTAAGGGAGTGGAGGAGGAGGAGGCGGGGATGTCGGAGCGGCGGAAGAGGATGAC
CATGGAGGTGTTTGTTGGTGGGCTTCACCGGGACGCCAAGGAGGATGATGTGAGGGCGGTGTTC
GCCAAGGCCGGGGAAATCACCGAGGTCCGGATGATAATGAATCCTCTTGCAGGGAAGAACAAGG
GGTACTGCTTCGTGCGCTACCGCCACGCCGCGCAGGCGAAGAAGGCCATCGCGGAATTCGGCAA
TGTGAAGATTTGTGGGAAGCTCTGTCGAGCTGCAGTTCCAGTTGGGAATGACAGAATTTTTCTT
GGAAACATCAACAAGAAATGGAAAAAGAAGATGTCATCAAGCAGCTAAAGAAAATTGGAATTG
AGAACATTGATTCTGTAACACTTAAGTCTGATTCAAATAATCCAGTCTGTAATCGTGGTTTTGC
ATTTCTTGAACTGGAAACTAGTAGAGATGCACGGATGGCATACAAAAAGCTTTCACAGAAAAAT
GCTTTTGGCAAAGGCCTGAATATAAGAGTTGCATGGGCTGAACCATTGAATGATCCAGATGAGA
AAGATATGCAGGTTAAATCGATTTTGTGGATGGGATACCAACGTCCTGGGATCATGCTCAGCT
AAAAGAAATCTTCAAGAAACATGGGAAGATTGAAAGTGTGGTTCTGTCACGCGATATGCCGTCA
GCTAAAAGGAGGGACTTTGCCTTTATTAATTACATTACTCGTGAGGCTGCAATCTCGTGTCTTG
AATCTTTTGACAAGGAAGAGTTCAGTAAGAACGGCTCAAAGGTGAATATTAAAGTTTCATTGGC
TAAACCTGCCCAACAGAGCAAGCAGACCAAGGAAGACCATAAATCTAGTATTACTGGGGAAGGC

FIGURE 6 (continued)

```
AAAATGAAGACTTCTAAAATAAGATACCCTGTTCAAGATTATACCCACATTTATTCTGGAGAGA
AGCGTCCCTTTTCAACACTGGGTGATCCTTATTATCCATTGAGAGGTCATTCTTGTCGTCGTCA
TGAGGGTAGCACCTATACTACAGCAGCATCAAGCTATGGTGCGCTGCCCCCTGCTACTGCTGAA
TCTTCTCTGCCACATTATCATGACAGCAATAGATATCCTCCACACCTAGGTGAGGCAATCAAGT
TCTCGCCAACCAGCGCAGTCCTATCGAAGCAGGCATGGCAAAAAATGTAA
```

**seq id no 10: *Oryza sativa* RNA-binding protein (BAC83046.1)**
```
MEPTRRCVPGHLATAAAAAAASPFSPPPSLPLPSALMPPKKRRLFTPAPRHAATPPPPPPPPTP
AVEPTLPIPPASTPPTPPQPSASTEPSTAPPPAVDDAAARSSSSSSPASAAAARKVRKVVKKVI
VKKVVPKGTFAARKAAAAAVAAAAAVSGAAASSEAGGEAPTDEPASDQDGGVGNEQKLDESKPA
TDCNAVAVVEESVCKEEEEVALVVGKGVEEEEAGMSERRKRMTMEVFVGGLHRDAKEDDVRAVF
AKAGEITEVRMIMNPLAGKNKGYCFVRYRHAAQAKKAIAEFGNVKICGKLCRAAVPVGNDRIFL
GNINKKWKKEDVIKQLKKIGIENIDSVTLKSDSNNPVCNRGFAFLELETSRDARMAYKKLSQKN
AFGKGLNIRVAWAEPLNDPDEKDMQVKSIFVDGIPTSWDHAQLKEIFKKHGKIESVVLSRDMPS
AKRRDFAFINYITREAAISCLESFDKEEFSKNGSKVNIKVSLAKPAQQSKQTKEDHKSSITGEG
KMKTSKIRYPVQDYTHIYSGEKRPFSTLGDPYYPLRGHSCRRHEGSTYTTAASSYGALPPATAE
SSLPHYHDSNRYPPHLGEAIKFSPTSAVLSKQAWQKM
```

**seq id no 11: *Oryza sativa* prolamin promoter**
```
CTTCTACATCGGCTTAGGTGTAGCAACACGACTTTATTATTATTATTATTATTATTATTATTAT
TTTACAAAAATATAAAATAGATCAGTCCCTCACCACAAGTAGAGCAAGTTGGTGAGTTATTGTA
AAGTTCTACAAAGCTAATTTAAAAGTTATTGCATTAACTTATTTCATATTACAAACAAGAGTGT
CAATGGAACAATGAAAACCATATGACATACTATAATTTTGTTTTTATTATTGAAATTATATAAT
TCAAAGAGAATAAATCCACATAGCCGTAAAGTTCTACATGTGGTGCATTACCAAAATATATATA
GCTTACAAAACATGACAAGCTTAGTTTGAAAAATTGCAATCCTTATCACATTGACACATAAAGT
GAGTGATGAGTCATAATATTATTTTCTTTGCTACCCATCATGTATATATGATAGCCACAAAGTT
ACTTTGATGATGATATCAAAGAACATTTTTAGGTGCACCTAACAGAATATCCAAATAATATGAC
TCACTTAGATCATAATAGAGCATCAAGTAAAACTAACACTCTAAAGCAACCGATGGGAAAGCAT
CTATAAATAGACAAGCACAATGAAAATCCTCATCATCCTTCACCACAATTCAAATATTATAGTT
GAAGCATAGTAGTA
``` seq id no 12: Artificial sequence - motif I (consensus sequence)
```
PYEAAVVALPVVVKERLVRILRLGIATRYD
``` seq id no 13: Artificial sequence - motif II (consensus sequence)
```
RFDPFTGEPYKFDP
``` seq id no 14: At1g58470 (contig f9k23 - coordinates: 4229-5089, 5173-5394)
```
aagatttgggcttacaatctttatcacaaaggcttttttaaagcccattagttacattcatcat
tatctctcgacattaaaaaaaaaagttaaactgaagaagctaaaaagagttttttaacttttaa
ctctcttcgtcttctccctcgtgccgtgtcaaatcaatctactgttctctctcctatctggtaa
acttttcctcttcgccatgaaatttttttcttgctagggttttagtttctacagttcgcttccc
aaaaattaggggttttgtcacaatttctcaatttcttgttccattttttcttcttttctccataa
```

FIGURE 6 (continued)

tcattgcttaatttagaatcccaaattttacaaattagggttttgttttaattttagggttt
tgattttcaactgttaatagtgttctcgatgtcataattctgatttttttattatctattccg
aaattagggcaaaaatctcagacaaacctgcaaaattagggtatttgaggatATGGATTATGAT
CGGTACAAGTTATTTGTTGGTGGTATTGCGAAAGAGACAAGTGAAGAAGCTCTGAAGCAGTATT
TTAGCAGATATGGAGCTGTGTTGGAAGCTGTTGTAGCTAAAGAGAAAGTCACTGGAAAACCTAG
AGGTTTTGGGTTTGTTCGCTTTGCTAATGATTGTGATGTTGTTAAAGCTCTTAGAGACACTCAC
TTCATTCTCGGTAAACCCgtaagtgttaccgcctttttatgcttgtgtcaattgggttttgtgt
atactctgtggattgattatgtgtgtgtttgtattagGTTGATGTGAGAAAGGCGATTAGGAAA
CATGAACTATACCAACAGCCGTTTAGCATGCAGTTTTTGGAGAGAAAAGTGCAACAGATGAATG
GTGGTTTGCGTGAGATGTCGAGTAATGGTGTGACCAGTAGGACTAAGAAGATATTTGTTGGGGG
TTTGTCGTCTAACACGACTGAGGAAGAGTTTAAGAGTTACTTTGAGAGGTTTGGTAGGACTACT
GATGTAGTTGTGATGCATGACGGTGTGACTAACAGGCCAAGGGGTTTTGGGTTTGTTACTTATG
ATTCGGAGGACTCTGTTGAGGTTGTTATGCAGAGTAATTTCCATGAGTTGAGTGATAAACGCGT
GGAAGTGAAACGGGCAATACCTAAAGAAGGAATCCAGAGCAATAACGGTAATGCTGTTAATATT
CCTCCTTCCTACAGCAGCTTTCAAGCAACACCTTATGTCCCTGAGCAAAACGGATATGGGATGG
TTTTACAGTTTCCTCCTCCTGTCTTTGGTTATCATCACAATGTCCAAGCCGTTCAATATCCTTA
TGGTTACCAATTCACAGCACAAGTGGCTAACGTTTCATGGAACAATCCGATTATGCAACCCACC
GGTTTTTACTGTGCTCCTCCTCATCCTACTCCTCCTCCCACCAACAATCTTGGTTATATCCAAT
ACATGAACGGGTTTGATCTTTCGGGTACGAACATTTCCGGGTACAATCCTCTAGCATGGCCTGT
AACGGGGGATGCAGCTGGTGCGCTAATACATCAGTTTGTAGATTTGAAGCTTGATGTCCACAGT
CAAGCCCATCAGAGAATGAATGGAGGTAACATGGGAATACCATTGCAGAATGGTACATATATAT
GAcagttgcagaatgataaatgcaaataggctcacaagggtagtgaaattctttggactctttt
aaatggttttttaggttcctcatctttcttcattaactctttggtaaatgtgttgggttggttt
ggttaccttgtatattgtttaggtatttgattttaaccccaagacttatgtatcatatattact
gcatttgtaatatatcacactcatttagttcattttgttgcttttatggttttgttgattttgt
ggtttcgttgattaaattggcaatgatgttttaaattcatcaaggaaaacaaagaaatagattg
tcgattaaacagtagaaaaggaaatagttttgtagaaataggaactgaatctggaaatctcta
agaataccatattgtagaaagaaaataaatctgagacgggagaaactatcgagcatccttgagc
tttaagtggagaaaccgggtaagcgtttgtgggattttgttgtaagattgaac seq id no 15: At1g58470 protein sequence
MDYDRYKLFVGGIAKETSEEALKQYFSRYGAVLEAVVAKEKVTGKPRGFGFVRFANDCDVVKAL
RDTHFILGKPVDVRKAIRKHELYQQPFSMQFLERKVQQMNGGLREMSSNGVTSRTKKIFVGGLS
SNTTEEEFKSYFERFGRTTDVVVMHDGVTNRPRGFGFVTYDSEDSVEVVMQSNFHELSDKRVEV
KRAIPKEGIQSNNGNAVNIPPSYSSFQATPYVPEQNGYGMVLQFPPPVFGYHHNVQAVQYPYGY
QFTAQVANVSWNNPIMQPTGFYCAPPHPTPPPTNNLGYIQYMNGFDLSGTNISGYNPLAWPVTG
DAAGALIHQFVDLKLDVHSQAHQRMNGGNMGIPLQNGTYI seq id no 16: At4g26650 (contig wt_d_33 – coordinates: 74595-74606, 74780-75016, 75420-76524, 76622-76635)
cttcattgagagagagatatagagagagaaagagagagaggccatatttgataagagaagaa
gaacccttatagagaaagagaaagagagagacagagagagtggatggatgtcttatagaatgaa
caaacatcctctgtttctcttgtccttgtcccttttccagatcttaaggttttccacatttt
atcatctgggtcctctccttaatggtgaattctccatctttacaagtttgatgtttttgttcat
caaatctggcgttttttttctcttctaatatatattgtctctgctcattttccgtttctcttc FIGURE 6 (continued)

```
ccattgattgttctgtttcatttctgtttttttttttttcaatagttttgattggatgctttgat
gatccattgtcagatttgaagacactcaattcctatttgatcggggactagaatttggattctg
tttcagacaaaagtagatttccctgtctctttcccgtttgattttcaataagATGAATCCGGAG
gtaaaacattgaacaattcttcataaatctcagaactttgagcttttttgaatcttaaaacacg
atcgaagtaaaaaatcgaattgttagatgaaatgggcaatcgtcattttcgcaaatctgatccg
tatttgtgagatcggattcattggatcgactttggggttttgcagGAGCAAAAGATGGAATCTG
CATCGGATCTGGGCAAGCTCTTCATTGGCGGGATTTCATGGGACACAGATGAAGAACGACTGCA
AGAGTATTTTGGCAAGTATGGAGATTTGGTTGAAGCTGTGATCATGAGAGACCGTACTACCGGA
CGTGCCCGTGGCTTTGGGTTTATCGTTTTTGCAGATCCTTCTGTTGCCGAGAGAGTCATCATGG
ACAAACACATCATTGATGGCCGCACGgttagtattcttggatccattgcttgacaattcatcta
attatcagtcttgagtaatcgagtgttctaaagtctcgatctttctgtaatgattctgtcttag
aggtcttattggtctcgctgctcgttaatgagcaacggattgttctataatctcgatctttctg
tattcatgctctcttagagatctgtttggtgtcatccattaatgagtttttaagcagcaacgttt
agatctttctgtaatcatgctcttttcgaaatcttctgttgtcattagcttctggatttgctgt
tactgttataacttgtgagaatgtgttgttgctttgtgttgaagtggcaatgttagtgttagat
caatgagaaaagaatgaaagatctttttttatttctttgttgcagGTCGAGGCGAAGAAAGCTG
TCCCGCGGGATGATCAGCAAGTGCTAAAACGACACGCCAGTCCAATGCACCTTATCTCACCTAG
CCATGGTGGTAATGGTGGTGGAGCACGGACAAAGAAGATCTTTGTTGGAGGTTTACCGTCTAGC
ATTACTGAGGCCGAGTTCAAGAACTACTTTGATCAGTTTGGTACAATTGCTGATGTTGTGGTAA
TGTATGATCATAATACACAGAGGCCAAGAGGCTTTGGCTTCATCACTTTTGATTCCGAAGAGTC
TGTTGATATGGTTCTCCACAAGACCTTTCATGAGCTAAACGGAAAAATGGTTGAGGTTAAAAGA
GCAGTGCCAAAGGAGCTCTCCTCGACTACTCCTAACCGAAGCCCACTTATTGGGTATGGTAACA
ACTATGGAGTAGTCCCTAATAGGTCTTCTGCTAATAGCTACTTCAATAGTTTTCCTCCTGGTTA
TAATAATAATAATCTAGGCTCTGCTGGCCGGTTTAGTCCTATTGGTAGCGGTAGAAATGCTTTC
TCTAGCTTCGGGCTCGGATTGAATCAAGAACTGAATTTGAATTCAAACTTTGATGGAAACACTC
TTGGGTATAGCCGGATCCCTGGCAACCAATACTTCAACAGTGCTTCACCAAACCGTTACAACTC
TCCAATTGGGTACAACAGAGGAGACTCTGCTTACAACCCGAGCAACAGAGACTTGTGGGGAAAC
AGAAGCGATTCCTCTGGTCCAGGTTGGAACTTGGGAGTTTCGGTTGGTAACAACAGAGGAAACT
GGGGACTTTCTTCTGTGGTGAGCGATAACAATGGCTATGGAAGAAGCTATGGGGCTGGTTCTGG
ACTTTCGGGGTTATCATTCGCGGGTAATACAAACGGTTTTGATGGCTCTATAGGGGAATTGTAT
AGAGGCAGCTCAGTTTATAGCGACTCAACATGGCAGCAGTCAATGCCTCATCATCAGTCTTCTA
ATGAGTTAGACGGCTTGTCTCGCTCTTATGGCTTTGGTATTGACAATGTAGGCTCAGACCCATC
AGCCAATGCCTCAGAAGGATACTCCGGAAACTACAATGTCGGAAATAGACAAACACATAGAGgt
acactcatcgatgtcaaactttttccttttgcatctcatctgctacatttatttttgcctgtt
gaaaagtaattagattgattaacgttttcagGTATTGAAGCATAGaaagaaatcgacgaagaga
agtgagaattgtagatcaagaagaacagccatttccgttgcagagtttgaagagttgttatttc
gatatcaagtagagaaagaaaccaactttcttcatcacagtgagtttcttgttttgttttttc
gtcgttagcatcacaaacacaaaaagagaagtttatttttactttaaaaattcttacataaga
taagatcagattggtagctgcaaagatacaacatggatgataaaaaagatttggtttcgtctc
catagcaataaccagagatcgttgattctcgatcactattctttaggtttctctccttcttctt
ccatgatttcttgatgttgtgtgctctgtttgtaactctaattgttaaaattttttatgttaca
gatttttttttttcttttggttttttaaactttggattcgaattgttcatgggaacttttggatttt
ttctattagcgtgagagaaaacacattgtgcaa
```

FIGURE 6 (continued)

seq id no 17: At4g26650 protein sequence
MNPEEQKMESASDLGKLFIGGISWDTDEERLQEYFGKYGDLVEAVIMRDRTTGRARGFGFIVFA
DPSVAERVIMDKHIIDGRTVEAKKAVPRDDQQVLKRHASPMHLISPSHGGNGGGARTKKIFVGG
LPSSITEAEFKNYFDQFGTIADVVVMYDHNTQRPRGFGFITFDSEESVDMVLHKTFHELNGKMV
EVKRAVPKELSSTTPNRSPLIGYGNNYGVVPNRSSANSYFNSFPPGYNNNNLGSAGRFSPIGSG
RNAFSSFGLGLNQELNLNSNFDGNTLGYSRIPGNQYFNSASPNRYNSPIGYNRGDSAYNPSNRD
LWGNRSDSSGPGWNLGVSVGNNRGNWGLSSVVSDNNGYGRSYGAGSGLSGLSFAGNTNGFDGSI
GELYRGSSVYSDSTWQQSMPHHQSSNELDGLSRSYGFGIDNVGSDPSANASEGYSGNYNVGNRQ
THRGIEA seq id no 18: At5g55550 (contig mte17 - coordinates: 77934-79094, 79236-79457)
atatgtgagactaactattgttctctgtctcttttttcttttta attatcaaagaaagaaact
ctttcttaatggaaaccatttacagataaaaaaaacattaaaaggaaaggttttta ataaagcc
tttgagagagaagatgtttattataggatgaacaaaaacatcctctgtttctctcttttcatat
ttttctccacatttcctcatctgggtcatctccaaaaatggtgcttttttttaataattcttca
cgtttctgggttttggttttgtgatttgatgatgctttttttttgttttttcagatttgatg
ataacccaaattcgcaatttgattaggacaacaacaacaactttatttatctgattccgtcttt
gatttcagacaagaaaagtatgttgtttctaagtcttttgattttttttcaatttcatctcctt
actcgatttttttttttttgggtttctctgaattggagcagaaaaaaaaaagATGGAATCGGAT
CTGGGGAAGCTCTTCATTGGTGGGATTTCGTGGGATACAGACGAAGAAAGGTTAAGAGACTACT
TTAGCAACTATGGTGATGTTGTTGAAGCTGTGATCATGAGAGATCGTGCCACAGGTCGTGCACG
TGGCTTCGGCTTCATTGTCTTTGCAGACCCCTGTGTCTCAGAGAGTGATCATGGATAAACAC
ATCATCGATGGCCGCACGgtttgtgatttcaatcatttctcaatctttcagcagaacaaacaaa
gttcagatcttattgcaacttcctcaatttgcgttttttgaatcatctctcaatctttgtttctc
aaagtgtaaagatcaaatttatgttttgcagGTTGAGGCGAAGAAGGCTGTGCCTCGAGATGAT
CAGCAGGTGCTAAAGCGACACGCTAGTCCTATCCACCTTATGTCACCTGTCCATGGTGGTGGTG
GAAGGACAAAGAAGATCTTCGTTGGAGGTTTACCGTCTAGCATTACCGAGGAGGAGTTCAAGAA
CTACTTTGATCAGTTTGGTACTATTGCTGATGTTGTTGTAATGTATGATCATAACACGCAGAGG
CCAAGAGGTTTTGGCTTCATCACATTTGATTCAGATGATGCTGTTGATAGAGTTCTTCACAAGA
CCTTCCATGAGCTCAATGGGAAACTAGTTGAGGTCAAAAGAGCTGTACCTAAGGAGATTTCCCC
TGTTTCTAATATCCGAAGCCCGCTTGCTAGCGGTGTTAACTATGGAGGCGGGTCTAATAGGATG
CCTGCTAATAGCTACTTTAACAACTTTGCTCCTGGTCCTGGTTTTTATAACAGTCTAGGTCCTG
TTGGTCGTCGGTTTAGTCCTGTTATTGGTAGTGGTAGAAATGCGGTTTCTGCTTTTGGCCTCGG
TTTGAATCATGACTTGAGTTTGAATTTGAATCCAAGCTGCGATGGGACAAGTTCTACGTTTGGT
TATAACCGTATTCCAAGCAACCCTTACTTCAACGGTGCTTCCCCGAACCGTTACACCTCTCCAA
TCGGGCACAATAGAACTGAGTCTCCTTACAATTCGAACAATAGAGACTTATGGGGAAACAGAAC
CGACACTGCAGGTCCCGGTTGGAACTTGAATGTCTCGAATGGAAACAACAGAGGAAATTGGGGA
CTTCCTTCTTCTTCTGCTGTTAGTAATGATAACAATGGCTTTGGAAGGAACTATGGGACAAGTT
CTGGACTTTCCTCGTCCCCATTTAATGGTTTTGAAGGTTCTATAGGGGAACTGTACAGAGGCGG
CTCAGTCTACAGCGACTCAACGTGGCAGCAACAGCAGCTACCATCTCAGTCTTCTCACGAGCTA
GACAATTTGTCTCGCGCTTACGGTTATGATATTGACAATGTAGGTTCAGACCCATCTGCAAATG
ACCCAGAAACTTACAATGGAAGCTACAATGTTGGAAATAGACAAACTAATAGAGGTAACAAAA
AATTCATCTCAATAAAACTTGTAACTTGGATACATTTTGAtcgcaatcgaaatgttctgatctg
tgttttatttacttgttgaggtattgctgcataggttatcaaaaaccaagaaaacaaaaaaaaa
agttgagagatttgtagattgaaagcaaccaaatttcagttgcagagtttgaacaggttctcat

FIGURE 6 (continued)

gacaaagaaaccaactttgttgatcacagtgccaaagattatggtttgctttctcttttgttag
accaaaaaaaaaaaaaaaaagagagaaaaacaaagaaccgttttttgttttcttcttcttacata
aagatcagatcgtagcagccagacaaccaaagatactacaagtggatttagatttgcttctca
aaaaagtttttttttttctttcatagaataaccaaacaaagatcgtagaattttcgatcaaaga
ttcttcagagttctgtgctctgttttgtaattgtacttttttttttcttgtttacaaaatgaatt
gttcatgaaaactttgttttcttaaaaa seq id no 19: At5g55550 protein sequence
MESDLGKLFIGGISWDTDEERLRDYFSNYGDVVEAVIMRDRATGRARGFGFIVFADPCVSERVI
MDKHIIDGRTVEAKKAVPRDDQQVLKRHASPIHLMSPVHGGGGRTKKIFVGGLPSSITEEEFKN
YFDQFGTIADVVVMYDHNTQRPRGFGFITFDSDDAVDRVLHKTFHELNGKLVEVKRAVPKEISP
VSNIRSPLASGVNYGGGSNRMPANSYFNNFAPGPGFYNSLGPVGRRFSPVIGSGRNAVSAFGLG
LNHDLSLNLNPSCDGTSSTFGYNRIPSNPYFNGASPNRYTSPIGHNRTESPYNSNNRDLWGNRT
DTAGPGWNLNVSNGNNRGNWGLPSSSAVSNDNNGFGRNYGTSSGLSSSPFNGFEGSIGELYRGG
SVYSDSTWQQQQLPSQSSHELDNLSRAYGYDIDNVGSDPSANDPETYNGSYNVGNRQTNRGNKK
IHLNKTCNLDTF seq id no 20: At4g14300 (contig fca_all - coordinates: 189072-189220, 189554-189611, 189665-190678)
ctgtaatgtggagtttggaattttcgacaacaaagtgcacatctggcacagagattgtcacagc
acgaaagatttttttgtcgttcttgtaggatttgctggcacgtgtggaatagaaaacacacgag
tgaaaccatcgtcggtctttgtagcccattatttatacttctattgggctggacttaagcccat
aagtaagcatctctgttacaagaaaacgggaaacagatctgaaccgttaataatattagaaagg
atctagaccgttgatttatttatctgctgacagattcgtaccttcgcgaatatcaataccaaac
caatagaaatattcgttcgctgtcttcttcctcttcctcctctcaaatcggctacagccattgg
aaaagctaaagccttttcgtaatttctggaagtttctgcagtcggttttcacggtttcgtagat
tgaggtggatttgtgattctgggtcagaagtaagatagtggaatataaattcATGGATTCGGAT
CAAGGAAAGCTTTTTGTCGGTGGTATTTCATGGGAAACTGATGAAGATAAGCTGAGAGAACATT
TCACCAACTATGGAGAGGTTTCTCAGGCTATTGTGATGAGAGACAAGCTCACAGGTCGACCTAG
GGGTTTTGGgttcgttatcttctcggatccttctgttctcgatagggttcttcaagagaaacac
agcattgataccagagaggttattattgttctcttatagctccatttctctaattgtgttaaag
ttttatccttttttgcgttttgctgtgttgattgagaacgagagtaaatatagaattttgtttgg
ttggcaaattcgccttagtgtttcttagattctaggattggttttaacttgtataagaggtatt
ataggggtactcgatatatgttaatcgtacactctatgaagtgattgagtatagtattagaaaag
agagcttggtttggtttattagGATAAGGAAAAACAGATGTATATATTTTCTGTTGCGTTATGT
TCTCGATTTGGGTAAAgtatgattcttggaagtttattatgagctttattgattttggttaatg
tttagGTTGATGTGAAGAGAGCCATGTCAAGAGAGGAGCAGCAAGTCTCTGGAAGAACTGGGAA
TCTTAATACATCTAGAAGTTCTGGAGGTGATGCTTACAATAAAACCAAGAAGATCTTTGTTGGA
GGCTTGCCACCTACTTTGACTGATGAAGAGTTTCGCCAGTACTTTGAAGTTTATGGCCCTGTGA
CTGATGTTGCAATCATGTATGACCAGGCTACCAACCGTCCTCGTGGGTTTGGATTTGTTTCCTT
CGACTCTGAAGATGCGGTAGACAGTGTTTTGCACAAGACTTTCCATGATTTGAGCGGTAAACAA
GTTGAAGTAAAGCGTGCTCTTCCTAAAGATGCCAATCCTGGAGGTGGTGGACGATCAATGGGTG
GTGGTGGCTCTGGTGGTTACCAGGGTTATGGTGGCAATGAAAGCAGTTATGATGGACGTATGGA
TTCCAATAGGTTTTTGCAGCATCAAAGTGTTGGAAATGGTTTACCATCTTATGGTTCTTCTGGT
TATGGCGCTGGCTATGGAAATGGTAGTAATGGTGCCGGGTATGGTGCCTATGGAGGTTACACTG
GTTCTGCTGGAGGTTATGGCGCTGGTGCTACTGCTGGATATGGAGCAACGAACATTCCAGGTGC

FIGURE 6 (continued)

```
TGGCTATGGAAGTAGTACTGGAGTTGCTCCGAGAAACTCATGGGACACTCCAGCTTCTAGTGGT
TATGGGAACCCAGGCTATGGGAGTGGTGCTGCTCATAGTGGATATGGAGTTCCTGGTGCAGCTC
CTCCTACGCAGTCACCATCTGGCTATAGTAACCAAGGCTACGGTTATGGAGGGTACAGTGGAAG
TGATTCTGGTTATGGAAATCAAGCTGCATATGGTGTGGTTGGAGGGCGTCCTAGTGGTGGCGGT
TCAAACAACCCTGGTAGTGGTGGCTACATGGGAGGTGGTTATGGTGATGGATCTTGGCGATCTG
ACCCGTCACAAGGTTATGGTGGTGGGTACAATGATGGTCAGGGTCGACAAGGCCAGTAGtgact
gtgtaaggggattatgaccgccctggtttctggatccttgtcaagaagaatttagctcaaatca
aaggttccacaacttcctaacgggttggactgcttgaatctctttataagcatgtgctatctat
tacaataagtcacttctattaagttattttcggttgagtgtacttttgagttttggcagagtt
attataactacaggctttgctgttttcgtattatgtttgtcttcctagtattcttgccggattg
tttgttttgattgtgttattttgttttggccctgatggatataacttaagcagggaataatgct
tcagggtacttgttaagaaagcagatggtgagagcagaactcgatggaggtgagagtcaaattg
ctgaatgtatggtttgagtagaaagtagaggtagttggtaacgttagtggtaccattaagaaga
aggtgtagaaatagtgagaggtagctttgagaaaaaggcataatca
``` seq id no 21: At4g14300 protein sequence
```
MDSDQGKLFVGGISWETDEDKLREHFTNYGEVSQAIVMRDKLTGRPRGFGIRKNRCIYFLLRYV
LDLGKVDVKRAMSREEQQVSGRTGNLNTSRSSGGDAYNKTKKIFVGGLPPTLTDEEFRQYFEVY
GPVTDVAIMYDQATNRPRGFGFVSFDSEDAVDSVLHKTFHDLSGKQVEVKRALPKDANPGGGGR
SMGGGGSGGYQGYGGNESSYDGRMDSNRFLQHQSVGNGLPSYGSSGYGAGYGNGSNGAGYGAYG
GYTGSAGGYGAGATAGYGATNIPGAGYGSSTGVAPRNSWDTPASSGYGNPGYGSGAAHSGYGVP
GAAPPTQSPSGYSNQGYGYGGYSGSDSGYGNQAAYGVVGGRPSGGGSNNPGSGGYMGGGYGDGS
WRSDPSQGYGGGYNDGQGRQGQ
``` seq id no 22: At3g07810 (contig f17a17 - coordinates: 43905-44126, 44339-45587, 46069-46082)
```
ttgaaattgggttaaatcggtttgaatcggattgaacaaaaactgtattaataataattcttcc
tctacttttctctctgattgattccaatcttctttcattttcttcttcttcttctggggaa
ggggcaggttaaaattatgccatctattcaaatcgtgcctatcctcagatcttaactcttttct
ctacgagattcggcatctgggttttattcttcttggtgggttttttttattcttcttcttctg
atctcagatttcccctgattggttttttttttgctaaatccgttttatgttttcccgatcaaa
ctctcctggcagattctcggatctgttgttttctagattcaatctgaatttgattttacgtttt
tgtcttgtaaagatgtttccttttgatcagattttgataatccattgacatctctgattcaag
caaaagctaattaactttgatccgattcctttgtgtgtgtgtgcagagcaaaATGAATCGGAT
AATGGAAAGCTTTTCATCGGTGGGATATCTTGGGACACCAATGAGGAACGTCTCAAGGAGTATT
TCAGCAGTTTTGGAGAAGTGATCGAAGCTGTCATCTTGAAAGATCGTACCACTGGTCGTGCTCG
TGGTTTCGGTTTTGTTGTTTTGCTGATCCTGCTGTTGCTGAGATTGTTATCACCGAAAAACAT
AATATTGATGGCAGATTGgtatgttcactgttctctgcctttcgttttgtacaatgtaacttg
ttttcgaagcttccttatgcaatcaagccttcaagagttacagtttgttctcatttggttccga
ttaatcattttgtgctttgattggattttgagaagaaatgagtgatctttagttatatgagc
ttagttttcattttcaagttgtttgatcttccgcagGTTGAAGCCAAGAAAGCTGTTCCCAG
AGATGACCAAAACATGGTAAATAGAAGCAACAGCAGTAGCATCCAAGGTTCTCCCGGTGGTCCA
GGTCGCACAAGGAAGATATTTGTTGGAGGATTACCTTCTTCGGTTACAGAGAGTGATTTCAAGA
CGTATTTTGAGCAGTTTGGTACAACTACGGATGTGGTTGTCATGTATGATCACAACACACAAAG
GCCTAGAGGTTTCGGGTTTATAACCTACGATTCCGAGGAGGCGGTTGAAAAGGTATTGCTCAAG
ACATTCCATGAACTAAATGGTAAAATGGTTGAGGTTAAGCGAGCTGTTCCAAAGGAGTTATCTC
```

FIGURE 6 (continued)

```
CAGGTCCAAGTCGCAGTCCTCTTGGTGCAGGTTACAGCTATGGAGTTAATAGGGTCAATAACCT
CCTTAATGGGTATGCTCAAGGGTTTAATCCCGCTGCAGTTGGAGGCTACGGACTTAGGATGGAT
GGTCGGTTCAGTCCGGTTGGTGCTGGAAGAAGCGGGTTTGCAAATTACAGTTCTGGATACGGGA
TGAATGTGAACTTTGATCAGGGATTGCCCACAGGGTTCACGGGAGGTACAAATTACAATGGAAA
TGTTGACTATGGCCGAGGAATGAGCCCGTACTACATTGGTAACACAAACAGGTTTGGTCCTGCG
GTTGGCTATGAAGGGGGCAACGGAGGAGGAAACTCATCCTTCTTCAGTTCGGTTACACGGAACT
TATGGGGAAACAATGGTGGTCTTAACTATAACAACAATAATACAAACTCAAACTCCAATACATA
TATGGGAGGATCATCAAGTGGGAACAACACACTTAGTGGTCCATTTGGAAATTCAGGAGTCAAT
TGGGGTGCTCCTGGAGGAGGAAACAATGCTGTGAGTAACGAGAATGTGAAGTTTGGTTATGGAG
GAAACGGTGAATCTGGTTTTGGGTTGGAACAGGTGGTTATGCAGCAAGAAACCCAGGGGCTAA
CAAGGCAGCACCATCCTCTTCATTCTCTTCTGCCTCAGCAACCAACAACACGGGTTATGATACA
GCAGGACTTGCAGAGTTTTACGGGAATGGTGCAGTTTATAGTGACCCTACATGGAGATCACCAA
CTCCTGAGACAGAAGGGCCTGCTCCTTTTAGCTATGGGATTGGAGGAGGGGTTCCTTCTTCAGA
TGTTTCAGCTAGAAGTTCATCTCCAGGTTATGTTGGCAGTTACAGTGTGAACAAGAGACAACCA
AACAGAGgtaattgagttcagagtaattttctgctttaacatgtgattctatgaaaagcaaagg
actcttgagaaaagaatttagaaagcctagatagtttccaaattttgattatcctcgtcttc
tttctggaatatacaaaccatggtttagggtcttgcactaatggtgatctagaacaccttcgta
tcactagtgaattggcttttcctcagaaacacgaatatacttgcatgcagaaacagtagccatt
ctgcatctttattgtttttagttcatcagagattatttagaggaaagtttctttccgtgcttt
agatataagctcatggaactagaaaactagttgaatcttttatgttgctcacaccagtgtctat
gggaagtctaagaaacttgtgatgaagaaactcaattgcatgactggtttcttatcgctcttct
cttctctgaattatatttccttttcggttttgttgcagGAATTGCTACTTAGtacaatcgtt
tttgttttaccacgatattgtaggcgagccatcacggtgaacgatctgtgtcttttggcgaatc
ttttagattatcttcttttcccttcatacaaagccagtgaggacgaaacttgatcatatcatca
cctagagctaaccagagaatcccgcagacttttctgtcatggtttggttttctaaattcattgt
tcctcctaggcttttttctgctttctttttttttctattttgttttcttttcttcttcaatg
agggacagaagaaactgtatcagtctccggcgaggcggtaatacataaggagagttcaaaacaa
aaacccaaaaaaaaaaaaaaaagatgatccttcttcctcagttttcttcttcattgtcatgta
atggttcttcttcttttcttcttcttgggggttatggttaaggtttgtgttttgaggcagattg
tactagagttttttttcatgtttcttttgttttgtcgttttt
``` seq id no 23: At3g07810 protein sequence
MQSDNGKLFIGGISWDTNEERLKEYFSSFGEVIEAVILKDRTTGRARGFGFVVFADPAVAEIVI
TEKHNIDGRLVEAKKAVPRDDQNMVNRSNSSSIQGSPGGPGRTRKIFVGGLPSSVTESDFKTYF
EQFGTTTDVVVMYDHNTQRPRGFGFITYDSEEAVEKVLLKTFHELNGKMVEVKRAVPKELSPGP
SRSPLGAGYSYGVNRVNNLLNGYAQGFNPAAVGGYGLRMDGRFSPVGAGRSGFANYSSGYGMNV
NFDQGLPTGFTGGTNYNGNVDYGRGMSPYYIGNTNRFGPAVGYEGGNGGGNSSFFSSVTRNLWG
NNGGLNYNNNNTNSNSNTYMGGSSSGNNTLSGPFGNSGVNWGAPGGGNNAVSNENVKFGYGGNG
ESGFGLGTGGYAARNPGANKAAPSSSFSSASATNNTGYDTAGLAEFYGNGAVYSDPTWRSPTPE
TEGPAPFSYGIGGGVPSSDVSARSSSPGYVGSYSVNKRQPNRGIAT seq id no 24: At2g33410 (contig f4p9 - coordinates: 71729-71950, 72087-73079)
atgatctaacatttttctcaaataataaggtcattgatccttatataacatggaatcactata
acatttataacctacattcttgctcatatatctctctccttttttttccaacatattaacgact
aataataaaatttatcaaccattttaaatctctaaatggaacttattattacatgactaaaaaa

FIGURE 6 (continued)

```
taaaaataaataaataaataaacgaagctgatatggaaaagtcttctctttcttttttttttt
tggtaagtcgatctctctttcactcactttaacccaattggccgctattttccaaagtctgttt
atttttttaatctctctctcttctctctcacccaatttcacaaacccgaaaccctaattttctc
gggacactgaaattttacagcttctttcctcttcttcaccggggagatttgtcggtactaaat
ctagggttttgggtatcaccggagggttgaagagagagaaaaaaactcacaATGGAATCAGAT
CAGGGAAAGCTATTTATCGGCGGGATTTCATGGGATACCGACGAGAATCTTCTGAGAGAGTACT
TCAGCAATTTCGGCGAGGTTTTGCAGGTCACTGTTATGCGAGAGAAAGCTACTGGTCGTCCTAG
AGGATTCGGATTCGTCGCATTCTCGGATCCTGCTGTTATTGATAGGGTTCTTCAGGACAAGCAC
CATATTGATAATAGAGATgtaagcaaaaatcttgtttctcaaatgggtctttctaaattttgaa
tctttatagtaaaaattgatactttgaatcttgttgttgtcgaggtttgatttcatctttgat
ggatttaagttgtgttaatttcttagGTTGATGTGAAGAGAGCAATGTCTAGAGAGGAGCAGAG
TCCTGCTGGGAGATCAGGGACTTTTAATGCTTCTAGGAATTTTGATAGTGGAGCTAACGTGAGG
ACTAAGAAGATATTCGTGGGAGGTTTGCCTCCTGCATTAACATCAGATGAATTTCGGGCTTACT
TTGAGACTTATGGTCCTGTGAGTGATGCAGTCATTATGATTGATCAGACTACACAGCGTCCTCG
AGGATTTGGGTTTGTTTCTTTTGATTCTGAAGATTCGGTTGACCTTGTTTTACATAAGACTTTC
CACGATTTGAATGGTAAACAAGTCGAAGTTAAAAGAGCTCTTCCTAAAGATGCTAACCCTGGAA
TAGCCAGTGGTGGTGGTCGTGGCAGTGGTGGAGCTGGAGGGTTTCCGGGCTATGGTGGTTCTGG
TGGAAGTGGCTATGAGGGTCGTGTGGATTCTAATAGATACATGCAGCCGCAAAACACTGGAAGT
GGTTATCCTCCTTATGGTGGTTCTGGGTATGGTACTGGTTATGGTTATGGAAGCAATGGTGTAG
GTTATGGGGGTTTTGGTGGGTATGGCAATCCAGCTGGTGCGCCTTATGGGAATCCTAGTGTCCC
TGGAGCTGGGTTTGGAAGTGGTCCAAGAAGTTCATGGGCGCTCAAGCACCATCGGGTTATGGG
AATGTGGGATATGGAAATGCAGCTCCGTGGGGTGGTTCTGGTGGTCCTGGTTCAGCAGTAATGG
GTCAAGCTGGTGCATCTGCAGGTTATGGCAGTCAAGGTTATGGCTATGGTGGAAATGATTCCTC
TTACGGGACTCCATCTGCCTATGGTGCAGTAGGGGGGCGATCTGGGAATATGCCTAACAACCAT
GGTGGCGGTGGCTATGCGGATGCTTTAGATGGCTCTGGAGGCTATGGGAATCACCAAGGGAACA
ACGGGCAAGCTGGTTATGGTGGAGGTTATGGAAGTGGTAGGCAAGCTCAACAACAGTGAttgaa
gaagaaatactactagaatgtggttttatcgctgaccttgaaacctcctgctttccgccttaac
catgtcacgtctttggcggttagaccaggaggtggacctacgctggattatctcttttgttagt
ttctcaataagttgttttcaggcaattccggatactatttcctatcaagttgtagttttaagt
ttgcgtgcttatttatatttgtcgctttggaatggttttctttctctgttatcctctagtgttt
gtgtttaacgatacatcctccagattatcattattcatctcccttttggttcattcattttgt
tgaatattccattcacagattcttgcttttgcatctcctctgtttaggggaagatgatttgctc
agtgttcaatgtgatctaagaaaagtgtttggtagagcaagagctgcaataaatcactttgaga
ttgcgttgttacatgaaggtcgtgttggcggaaacttaacagtccca
``` seq id no 25: At2g33410 protein sequence
MESDQGKLFIGGISWDTDENLLREYFSNFGEVLQVTVMREKATGRPRGFGFVAFSDPAVIDRVL
QDKHHIDNRDVDVKRAMSREEQSPAGRSGTFNASRNFDSGANVRTKKIFVGGLPPALTSDEFRA
YFETYGPVSDAVIMIDQTTQRPRGFGFVSFDSEDSVDLVLHKTFHDLNGKQVEVKRALPKDANP
GIASGGGRGSGGAGGFPGYGGSGGSGYEGRVDSNRYMQPQNTGSGYPPYGGSGYGTGYGYGSNG
VGYGGFGGYGNPAGAPYGNPSVPGAGFGSGPRSSWGAQAPSGYGNVGYGNAAPWGGSGGPGSAV
MGQAGASAGYGSQGYGYGGNDSSYGTPSAYGAVGGRSGNMPNNHGGGGYADALDGSGGYGNHQG
NNGQAGYGGGYGSGRQAQQQ

FIGURE 6 (continued)

seq id no 26: At5g47620 (contig mnj7 - coordinates: 62491-62504, 62602-63661, 64000-64221)
tgagcattgcttatttgcttccatcctttttgttccttttaattcgatttggattgcagaaaa
agaaaagaaaagaaaagactaaaaatttggacgataagcagaaaagagagaggagggcctctcg
ccctcttattaaaaccttgccttctccaaatctgaagatttctcaatcctaaaatcttttttt
ttcctctttctccgtttctttattttcggtattacacacatacatagattctctgtcttctggg
tttttcattccttccttcctccaagcttacacctttattgatcatttgtgtttttttttgtttc
tgcaggaatccaagatcgtgggtcgatcggttttacacaatccgatcacgacccatctgctct
ttttcatcctatttgcttcccttgaggtgtttctatcgattccattctccttctcacttagat
cgatatagaatctggaaccaaaaacaaaccttttttgtttgtttggcagaaATGGAAATGGAA
TCATGTAAGCTCTTCATCGGTGGTATATCTTGGGAAACCAGTGAAGATCGTCTTCGTGACTATT
TTCACAGTTTTGGTGAGGTTTTAGAGGCTGTTATTATGAAGGATCGTGCCACTGGCCGTGCTCG
TGGCTTTGGTTTCGTTGTCTTTGCTGATCCTAATGTTGCTGAAAGAGTCGTCTTGCTTAAACAT
ATCATTGATGGTAAAATTgtaagtttcctcctgctatataccaacatacattgcttccaatttc
aacaatcttcctgcttacttgcttcattttgaggttgctgcttctcaaagcaaagcaaagctac
tcactttattccttcctgttttagttagtagactctattgtttacaatcagctttgccgctct
gataaatgcatatctttgtcagaagttgttcatttcacactcacaaataaaaatgtaaaacttg
gatcgtttcatatcctcatgtgaaagaaagtggttcacaatgaatgaaaaactgctttctttga
gttgtgtcgtgtgttgattttctccatgatatacagGTTGAGGCAAAGAAGGCTGTTCCAAGAG
ATGATCACGTAGTATTTAATAAAAGTAACAGCAGCCTTCAGGGATCACCTGGCCCATCAAACTC
CAAGAAGATCTTTGTGGGAGGTTTGGCATCATCCGTGACAGAGGCTGAGTTCAAAAAGTATTTT
GCTCAGTTTGGGATGATCACTGATGTTGTGGTGATGTATGACCACAGAACCCAGCGGCCTAGAG
GCTTTGGGTTCATTTCATATGACTCTGAGGAAGCTGTTGACAAAGTACTGCAGAAGACATTCCA
CGAACTCAATGGTAAGATGGTGGAGGTCAAACTGGCTGTTCCTAAGGATATGGCTCTCAACACA
ATGCGGAACCAAATGAATGTAAATAGCTTTGGCACTAGTAGAATCAGTTCATTACTGAATGAGT
ACACCCAGGGATTCAGCCCGAGTCCAATCTCTGGTTATGGAGTGAAACCTGAAGTTAGGTACAG
TCCAGCAGTAGGTAATAGGGGAGGATTCTCACCGTTTGGACATGGATACGGAATCGAGCTGAAT
TTTGAGCCAAACCAGACTCAGAACTACGGTTCTGGTTCCAGTGGAGGCTTTGGACGACCCTTTA
GCCCTGGATATGCTGCGAGTCTCGGCAGGTTCGGTAGCCAAATGGAGTCGGGAGGAGCTAGTGT
TGGGAACGGTTCTGTCCTAAATGCAGCACCAAAGAACCATTTATGGGGAAATGGTGGTCTAGGT
TACATGTCAAACTCTCCGATATCAAGAAGCAGCTTCAGTGGAAACTCTGGAATGTCTTCACTAG
GCAGCATTGGTGACAACTGGGGAACAGTTGCACGTGCACGCAGTAGCTACCACGGTGAGAGAGG
AGGTGTAGGATTAGAAGCAATGAGAGGAGTTCATGTTGGTGGTTACAGCAGCGGCTCAAGCATC
TTGGAGGCAGACTCTCTGTACAGCGACTCGATGTGGCTTTCGCTGCCTGCAAAGGCAGAGGAAG
GATTGGGAATGGGACCATTGGACTTCATGTCTAGAGGACCAGCTGGATACATCAACAGGCAACC
AAACGGAGgtatgaataatgaatgaatgaacgcttttttctatccgagaattcaagcatttgt
agaaaatctgatgatatcatatgaaaatggtgttgttgcagGAATTGCAGCTTAGagaagtgac
aaatctataccatggagatcagatgattgcagaagagagttttttagaagaggaaaaaagtttat
taaaaaaaaaaaattattggtaccaaaaagcttaaagcttttatttacttttactattttga
tttgttgttatagctttcttttcacccttttttctaatttggggttttgtttcttttgtttta
tcgttaaagaaaaagatgtaaacttgagtgatataaaaagagacaaagaaacaatgaagtgta
ttttgttcttgtctttctctctcttttatcatctaaatccatatattgacaaattcaaacatga
aaacgaattaaaaaagagcaatttgcctagaatgtaggcaacgtagtgtgaggacgacgtgtg
gcaaacatgtggatgatgataagccacaggacaaagaaagcaatccctcatccatcgcaataat
atccattaatgtgaagtggaccaaaagagagagaagcgagtgt

FIGURE 6 (continued)

seq id no 27: At5g47620 protein sequence
MEMESCKLFIGGISWETSEDRLRDYFHSFGEVLEAVIMKDRATGRARGFGFVVFADPNVAERVV
LLKHIIDGKIVEAKKAVPRDDHVVFNKSNSSLQGSPGPSNSKKIFVGGLASSVTEAEFKKYFAQ
FGMITDVVVMYDHRTQRPRGFGFISYDSEEAVDKVLQKTFHELNGKMVEVKLAVPKDMALNTMR
NQMNVNSFGTSRISSLLNEYTQGFSPSPISGYGVKPEVRYSPAVGNRGGFSPFGHGYGIELNFE
PNQTQNYGSGSSGGFGRPFSPGYAASLGRFGSQMESGGASVGNGSVLNAAPKNHLWGNGGLGYM
SNSPISRSSFSGNSGMSSLGSIGDNWGTVARARSSYHGERGGVGLEAMRGVHVGGYSSGSSILE
ADSLYSDSMWLSLPAKAEEGLGMGPLDFMSRGPAGYINRQPNGGIAA

**seq id no 28: NM_196957 DNA sequence (*Oryza sativa*)**
atggagtcggatcaggggaagctgttcatcggcggcatctcgtgggagaccaccgaggagaagc
tccgcgaccacttcgccgcctacggcgacgtctcccaggccgccgtcatgcgcgacaagctcac
cggccgccccgcggcttcggcttcgtcgtcttctccgacccttcctccgtcgacgccgccctc
gtcgaccccacaccctcgacggccgcacggttgatgtgaagcgggcgctctcgcgggaggagc
agcaggccgcgaaggcggcgaaccctagcgcggggggaggcacgcctccggtggggcggtgg
tgggggaggcgccggtggtggtggtggcggcggtggtgacgccggcggtgcgcggacgaag
aagatcttcgtcggcgggctgccctccaacctgacggaggacgagttccggcagtacttccaga
cctacggggtcgtcaccgacgtcgtcgtcatgtacgaccagaacacgcagcggccgaggggtt
cgggttcatcaccttcgacgcggaggacgccgttgaccgcgtgctgcacaagaccttccatgac
ctgagcgggaagatggtggaggtgaagcgcgccctgcccagggaggccaaccctggctccggca
gtggtggccgttccatgggaggcggcggtggggttaccagagtaacaatgggccgaactccaa
ttctgggggctatgatagcagaggtgacgctagcaggtatggtcaggcgcagcagggtagtggt
ggttatcccggttatggtgctggaggatatggtgctggtacggttggttatggatatggcatg
ctaaccctggaactgcgtatggaattatggggctggaggatttggaggtgttcctgctgggta
tggtgggcattatggcaatccaaatgcgcctggttcaggttaccagggtggtcctccaggagca
aacagaggaccatgggtggtcaagctccgtctggttatggcactgggagttatggtggcaatg
caggctatgctgcttggaacaactcttctgctggaggtaatgcacccactagtcaggccgctgg
tgcaggcacaggctatgggagccagggctatggatatggtggatatggaggagatgcatcgtat
ggtaatcatggtggatatgggggttatggaggaagggggagatggtgctggcaatccagctgctg
gcggtggatctgggtatggtgctggctatggaagcgggaatggcggttctggttatccaaatgc
ttgggctgatccttcacaaggtggagggtttgggcttcagtcaatggagtgtctgaaggccaa
tcaaattatggcagtggttatggtggtgtgcaacctagggttgctcagtaa

**seq id no 29: NP_921939 protein sequence (*Oryza sativa*)**
MESDQGKLFIGGISWETTEEKLRDHFAAYGDVSQAAVMRDKLTGRPRGFGFVVFSDPSSVDAAL
VDPHTLDGRTVDVKRALSREEQQAAKAANPSAGGRHASGGGGGGGAGGGGGGGGDAGGARTK
KIFVGGLPSNLTEDEFRQYFQTYGVVTDVVVMYDQNTQRPRGFGFITFDAEDAVDRVLHKTFHD
LSGKMVEVKRALPREANPGSGSGGRSMGGGGGGYQSNNGPNSNSGGYDSRGDASRYGQAQQGSG
GYPGYGAGGYGAGTVGYGYGHANPGTAYGNYGAGGFGGVPAGYGGHYGNPNAPGSGYQGGPPGA
NRGPWGGQAPSGYGTGSYGGNAGYAAWNNSSAGGNAPTSQAAGAGTGYGSQGYGYGGYGGDASY
GNHGGYGGYGGRGDGAGNPAAGGGSGYGAGYGSGNGGSGYPNAWADPSQGGGFGASVNGVSEGQ
SNYGSGYGGVQPRVAQ

FIGURE 6 (continued)

**seq id no 30: AK067725 DNA sequence (*Oryza sativa*)**
ggtccattatttataccatttccgcgtcccccaccctcctccccgctttcccaatcgaggcg
agcaccgcaattgcagggttccggaggccgaataaaaaagtttggcctctccccgcaaaaagt
aaaaaacccaaaacaaccatccaccagcgcatcgcggcaccgcgagcgagcgagcggagggagg
gaggtggagagcaaaagttcgataaaaggagaggaggagacgaagcgtcgaagcccaagtaaca
tcccccaacctccgcctcctcctcctcccccctcctcccatgcccgcatcgagatcttagccgc
gccggagatcgagagggaggagcggcgacgcgggcgccccgatccctcctcctcgccgccgcc
gccgccggcggcgccggagcagcagcagccgacgacgacgacgaccgccgcagcagccgatcgg
gggaggaggggaggggaggacgcgatggaggcggactccgggaagctcttcgtcggcggcatct
cgtgggagacggacgaggaccgcctccgcgagtacttcagccggttcggggaggtcaccgaggc
cgtcatcatgcgggaccgcaacaccggccgcgcccgtgggttcggcttcgtggtcttcaccgac
gcaggcgtcgccgagcgggtcaccatggataagcacatgatcgacgggcgcatggtggaagcga
agaaagctgttcccagggacgaccagagcatcaccagcaagaacaatggcagcagcatagggtc
acctggaccaggccgtactagaaagatctttgttggaggcttggcctctaatgttactgaggtt
gaatttagaaggtattttgagcaatttggtgtgattacggatgtggttgtcatgtacgaccaca
acacgcagaggcctagggctttggattcatcacctatgactcagaagatgcggtggacaaggc
actgcacaagaacttccatgagctgaatggtaagatggttgaggtcaagagagctgttccaaag
gagcaatcacctggacctgctgcacgttcacctgcgggagggcagaactatgctatgagcaggg
tccatagcttcttgaatggtttcaaccagggttataacccaaaccctattggaggttatggcat
gagggttgatggaaggtatggtctgcttacaggcgcacggaatggattctcttcatttggccct
ggttatggaatgggcatgaattctgaatctgggatgaatgcgaattttggcgccaattctagtt
ttgtcaataactccaatgggcggcagataggttcattctacaatggtagttcaaacagattagg
tagtcctattggttatgttggtcttaatgatgattcaggatcactattgagttcaatgtcaagg
aatgtttggggtaatgaaaatctgaactacccaaacaaccccacaaacatgagttcttttgcac
catctggaactggaggtcaaatgggtattaccagtgacggtattaattggggagggcctactcc
tggccatggaatgggcaacatttcaagccttgggctggctaaccttggccgtggagctggagac
agttttggcttgccttctggcagctatggaaggagcaatgcaactggtaccattggtgaaccct
tctctgcaccacccaatgcatatgaagtgaacaatgcagatacatatggcagcagctccattta
tggagactcaacttggaggttcacgtcatctgagattgatatgcctccttttggtaatgacctt
ggaaatgttgatccagatatcaaatcaaacataccagcaagttacatgggcaactatactgtta
ataataatcagacaagcagaggtatcacttcctagcgagagtactattatattcatatatgact
tgggatagatgaaagaagcattatatcaggtattcaggtgcatgactatgaattggtgatatca
ggttaatatacgggttagttaattgtttctagctaaccagaggtgtggtttatggacaccacca
tgctagaggagcgaatacaaacgttttgtgaaggtttcagattttagtttaattcctacatgta
ttaggtcttggttttgaatgagatgtgcagtggtgattgcggcacatacttagagtgttccaa
cataagctggaatcctgtcatatggacaaacttgtataccaaaggaatgctttattatcttgcc
catttatggctacattagctcgcttgttttcattcccttttaaccaattccatttgtatacta
gagatctgcttgacttactagtgaaactattcggggacgccgatcctatctttgcagttggctc
ccagaaataaagccaccaaaagtgcatacttatttgttctaccttgatttgccatatgtatatg
cttctgttcgttttaaaatagaactttgggtttgatt

**seq id no 31: AK067725 protein sequence (*Oryza sativa*)**
MEADSGKLFVGGISWETDEDRLREYFSRFGEVTEAVIMRDRNTGRARGFGFVVFTDAGVAERVT
MDKHMIDGRMVEAKKAVPRDDQSITSKNNGSSIGSPGPGRTRKIFVGGLASNVTEVEFRRYFEQ
FGVITDVVVMYDHNTQRPRGFGFITYDSEDAVDKALHKNFHELNGKMVEVKRAVPKEQSPGPAA

FIGURE 6 (continued)

rspaggqnyamsrvhsflngfnqgynpnpiggygmrvdgrygllllllltgarngfssfgpgygmgmns
esgmnanfganssfvnnsngrqigsfyngssnrlgspigyvglnddsgsllssmsrnvwgnenl
nypnnptnmssfapsgtgqmgitsdginwggptpghgmgnisslglanlgrgagdsfglpsgs
ygrsnatgtigepfsappnayevnnadtygsssiygdstwrftsseidmppfgndlgnvdpdik
snipasymgnytvnnnqtsrgits

**seq id no 32: AK070544 DNA sequence (*Oryza sativa*)**
ttggagatagaatagagagagacacacaaacacctacaacaccaacaacaacaagagaaagaga
gaaagaagagaaggaaaggagaggaagaagaggtggtggtggtggtggtggtgtgtggcct
ccttcccctcctcctctcgcgaggttgccatgcctcccccaagatcgatccaacccgatcatc
aatcggggcggggaaggaggaggagggggatggaggcggacgccgggaagctgttcatcggcggc
atctcgtgggacaccaacgaggaccgcctccgcgagtacttcgacaagtacggcgaggtggtgg
aggccgtcatcatgcgcgaccgcgccaccggccgcgcccggggattcggcttcatcgtcttcgc
tgaccctgccgtcgccgagcgggtcattatggagaagcacatgatcgatggccgcatggtggag
gcgaagaaagctgttcccagggacgatcagcacgctcttagcaagagcggcgggagcgctcatg
gatcgccggggcccagccgcaccaagaagatattcgttgggggctagcgtccaccgtgacgga
ggcggacttcaggaagtactttgagcagttcgggacgatcaccgatgtcgtggtgatgtatgat
cacaacacgcagcgtcccagaggttttgggttcattacgtacgattcggaggatgctgtggaca
aggcattgttcaagaccttccatgaactgaacggtaagatggttgaggtcaagcgcgcggttcc
taaggaactatcacctgggcctagcatgcgttctcctgtcggtggattcaactatgccgtgaac
agagccaataacttcctcaatggatacacccagggttataatccgagcccagtcggtggctatg
gaatgaggatggatgcaaggtttgggcttctatcgggtggccgtagtagttatccttcttttgg
tggtggttatggagtcggtatgaattttgatccagggatgaaccctgctattggggaagctca
agcttcaacaacagtctccagtatggaaggcagcttaatccatactacagtggaaattctggta
gatacaatagcaatgttagctatggtggagtcaatgacagtactgggtcagtgttcaactcgct
ggctcgtaatttatggggtaattcaggtcttagttactcttccaactctgcaagctctaattcc
ttcatgtcatctgccaatgggggccttggtggaattgggaacaacaatgtgaattggggaaacc
ctcctgtgcctgcacaaggtgctaatgctggcccaggctatggcagtgggaacttcggttatgg
atccagtgaaaccaactttggtctcggtaccaatgcttatggaaggaatgctggatctggtgtt
gttaatacattcaatcaatcaaccaatgggtatggaaggaactttggagattcatcaggaggag
gtggcggtggtggcggtggctccatctatggagacacaacttggagatccggatcttctgagct
tgatggaaccagcccatttggctatggcttgggaatgcagcttcagatgttacagcaaagaac
tcagcaggttacatggggcattaacaaatagagcaatgtcgccgcctaggaatcttttttcacat
acaacatttgtcaaaataggttgaggagagaaccacaggtgcatcaggtgcaaattttgaacct
cacatgatttacagaaatgggttagttaatagagctaaccaccagggatttggtcaatgagatc
agatatatatcctcagagaaccatttaaacgtatttccatttttatgtaaggtttgagattgtgg
tttcggatttctacagcgagtttaggttttggcaaccttgtgttttttcttggttgagatgtga
agtaagattgcgggatatatatatctgaagagtgttcagttgtacggcggcgctgcccccatat
aggccccctttttgggttttttgttcttatagtagaaactgctctagcgttttgcaaattgtgt
gctagctgttgttatcaggatgataatttttttcccttcttggttttatcttactgaagtgt
atgtaccagagatcttgctggtctgtgttttcctagtggaacttttgagggatgcccttctg
ggtctcaaagaataataatgctacattatattctaattcatttgaggctttctaaggctatat
attatttgtatgtaccctgctggaacatctgtacattctgatgctctttgcaatttgcctttgt
gctgcttttgc

**seq id no 33: AK070544 protein sequence (*Oryza sativa*)**
MEADAGKLFIGGISWDTNEDRLREYFDKYGEVVEAVIMRDRATGRARGFGFIVFADPAVAERVI
MEKHMIDGRMVEAKKAVPRDDQHALSKSGGSAHGSPGPSRTKKIFVGGLASTVTEADFRKYFEQ
FGTITDVVVMYDHNTQRPRGFGFITYDSEDAVDKALFKTFHELNGKMVEVKRAVPKELSPGPSM
RSPVGGFNYAVNRANNFLNGYTQGYNPSPVGGYGMRMDARFGLLSGGRSSYPSFGGGYGVGMNF
DPGMNPAIGGSSSFNNSLQYGRQLNPYYSGNSGRYNSNVSYGGVNDSTGSVFNSLARNLWGNSG
LSYSSNSASSNSFMSSANGGLGGIGNNNVNWGNPPVPAQGANAGPGYGSGNFGYGSSETNFGLG
TNAYGRNAGSGVVNTFNQSTNGYGRNFGDSSGGGGGGGGSIYGDTTWRSGSSELDGTSPFGYG
LGNAASDVTAKNSAGYMGH

**seq id no 34: CK210974 DNA sequence (*Triticum aestivum*)**
AAAAAGCAGGTGGGACCGGCCCGGAATTCTCGGGATATCGTCGACCCACGCGTCCGCGCACCCG
AGCGCGAGAGAATCCGAGGAGAGGAGCGGCGCAAGGAGGCGGTGATGGAGTCGGATCAGGGCAA
GCTCTTCATCGGCGGCATCTCCTGGGAGACGACGGAGGAGAAGCTGCAGGAGCACTTCTCCAAC
TTCGGCGAGGTCTCCCAGGCCGCCGTCATGCGCGACAAGCTCACTGGCCGCCCGCGGGGCTTCG
GCTTCGTAGTCTACGCCGACCCCGCCGCCGTCGACGCCGCCCTCCAGGAGCCCCACACCCTCGA
CGGCCGCACGGTCGATGTGAAGCGGGCGCTCTCGCGGGAGGAGCAGCAGGCTACCAAGGCGGTG
AACCCTAGCGCAGGAAGGAACGCTGGAGGTGGTGGCGGCGGCGGCGGCGGCGGCGATGCCG
GTGGTGCTAGGACAAAGAAGATTTTTGTGGGCGGACTGCCCTCCAGTCTGACAGATGAGGAGTT
CCGGCAGTACTTCCAGACCTTCGGGGCTGTCACCGATGTTGTGGTGATGTATGACCAGACAACA
CAGCGTCCCCGGGGCTTCGGCTTCATTACCTTTGACTCGGAGGATGCGGTTGACCGTGTGCTGC
ACAAAACCTTCCACGATCTTGGAGGGAAGATGGTAGAGGTGAAGCGTGCTCTGCCCCGAGAGGC
GAATCCTGGCTCTGGCGGCGGCGGCCGTTCCATGGGAGGTGGGGGGTTTCATAGTAACAATGGA
CCCCACTCCAATGCTAGCAGCTATGATGGCAGAGGCGATGCTAGCAGATATGGGCAGGCGCAGC
AAGGCATGGGTGGCTACCCAGGTTATGGTGCTGGAGCTTATGGCAGTGCTCCAACTGGGTTTGG
ATATGGGCCACCCAATCCGGGAACTACTTATGGAAATATTGGGTCTGCAGGGTTAGGAGCTTTT
CCTTGGTGCGTATGCGGGGGGCTTATGGGCAACCCAGGTGGCTGCGGGTTTCGGGTTACCCGGG
GGGGCCCCTCCGGGGCCCTAAATAAGGGACCCTGGGGGCAGCCAAACCTCCGCCCTGGTTTATG
GCACCTGGGGCTTTATCCTGGGCACGTGCGGGCTATTGGGTGCGTGGAAATAACCC

**seq id no 35: CK210974 protein sequence (*Triticum aestivum*)**
MESDQGKLFIGGISWETTEEKLQEHFSNFGEVSQAAVMRDKLTGRPRGFGFVVYADPAAVDAAL
QEPHTLDGRTVDVKRALSREEQQATKAVNPSAGRNAGGGGGGGGGGDAGGARTKKIFVGGLPS
SLTDEEFRQYFQTFGAVTDVVVMYDQTTQRPRGFGFITFDSEDAVDRVLHKTFHDLGGKMVEVK
RALPREANPGSGGGGRSMGGGGFHSNNGPHSNASSYDGRGDASRYGQAQQGMGGYPGYGAGAYG
SAPTGFGYGPPNPGTTYGNIGSAGLGAFPWCVCGGLMGNPGGCGFRVTRGGPSGALNKGPWGQP
NLRPGLWHLGALSWARAGLLGAWK

**seq id no 36: CA124210 DNA sequence (*Saccharum officinarum*)**
AGAATTCNCGGTTCGACCTACGCGTCCGCCCGGAATCCCCAATTCCGCTCTCTTCCTCTCTCCC
TCTCTCCCCCACCGCAGCATCAGGCGAGCGCGAGGCGGAGGTGGAGGAGAGATGGAGTTGGACC
AGGGCAAGCTCTTCATCGGCGGCATCTCCTGGGAGACGACGGAGGAGAAGCTGAGCGAGCACTT
CTCCGCCTACGGCGAGGTTACGCAGGCCGCCGTCATGCGGGACAAGATCACCGGCCGCCCCGT
GGCTTCGGGTTCGTCGTCTTCGCCGACCCCGCCGTCGTCGACCGAGCGCTGCAGGACCCCCACA
CCCTCGACGGCCGCACGGTCGATGTGAAGCGGGCACTCTCGCGGGAGGAGCAGCAGGCCTNCAA FIGURE 6 (continued)

```
GGCCGCGAACCCTAGCGGTGGGAGGAACACTGGCGGTGGANGANGCGGCGGGTGGCGGGGCGGC
GATGCAAGTGGTGCTCGGACCCAGGAAGATCTNTGGGGGGCCGGCTTGCCTTCTACTCTGACTG
ANGGATGGGTTTCGGCAGTACTTTCCGGACCTTCGGAGGGGTCACTGATGGTTGGTGGCCATGG
TTGAACCGGAACAAGCAATTGCCCGCGTTGGTTTTGGAATCAATACTTTTGAACTTTAAGATTC
CGGTGAACCGCTGCTGGCCAAGAACTTTCATGACCTGGTGGGAAGATGGTTTAAGGTGAACCAG
CATTGCGCCCTTGAGGCGAACCCTGGGGGTTCTGGAACGGGCCGTTCTGGGGGAAATGGGGGCT
TTCTAGCAACCATGGCCTTACCCCCGTTTTGG
```

**seq id no 37: CA124210 protein sequence (*Saccharum officinarum*)**
```
MELDQGKLFIGGISWETTEEKLSEHFSAYGEVTQAAVMRDKITGRPRGFGFVVFADPAVVDRAL
QDPHTLDGRTVDVKRALSREEQQAXKAANPSGGRNTGGGXXGGWRGGDASGARTQEDLWGAGLP
STLTXGWVSAVLSGPSEGSLMVGGHG
```

**seq id no 38: beta-expansin promoter (*Oryza sativa*)**
```
aaaaccaccgagggacctgatctgcaccggttttgatagttgagggacccgttgtgtctggttt
tccgatcgagggacgaaaatcggattcggtgtaaagttaagggacctcagatgaacttattccg
gagcatgattgggaaggaggacataaggcccatgtcgcatgtgtttggacggtccagatctcc
agatcactcagcaggatcggccgcgttcgcgtagcacccgcggtttgattcggcttcccgcaag
gcggcggccggtggccgtgccgccgtagcttccgccggaagcgagcacgccgccgccgccgacc
cggctctgcgtttgcaccgccttgcacgcgatacatcgggatagatagctactactctctccgt
ttcacaatgtaaatcattctactattttccacattcatattgatgttaatgaatatagacatat
atatctatttagattcattaacatcaatatgaatgtaggaaatgctagaatgacttacattgtg
aattgtgaaatggacgaagtacctacgatggatggatgcaggatcatgaaagaattaatgcaag
atcgtatctgccgcatgcaaaatcttactaattgcgctgcatatatgcatgacagcctgcatgc
gggcgtgtaagcgtgttcatccattaggaagtaaccttgtcattacttataccagtactacata
ctatatagtattgatttcatgagcaaatctacaaaactggaaagcaataagaaatacgggactg
gaaaagactcaacattaatcaccaaatatttcgccttctccagcagaatatatatctctccatc
ttgatcactgtacacactgacagtgtacgcataaacgcagcagccagcttaactgtcgtctcac
cgtcgcacactggccttccatctcaggctagctttctcagccacccatcgtacatgtcaactcg
gcgcgcgcacaggcacaaattacgtacaaaacgcatgaccaaatcaaaaccaccggagaagaat
cgctcccgcgcgcggcggcgacgcgcacgtacgaacgcacgcacgcacgcccaaccccacgaca
cgatcgcgcgcgacgccggcgacaccggccgtccacccgcgccctcacctcgccgactataaat
acgtaggcatctgcttgatcttgtcatccatctcaccaccaaaaaaaaaaggaaaaaaaaacaa
aacacaccaagccaaataaaagcgaca
``` seq id no 39: Artificial sequence (primer prm00405)
```
ggggacaagtttgtacaaaaaagcaggcttcacaatggattatgatcggtacaagttat
``` seq id no 40: Artificial sequence (primer prm00406)
```
ggggaccactttgtacaagaaagctgggtttaaaagagtccaaagaatttcact
```

FIGURE 6 (continued)

SEQUENCE LISTING

<160> NUMBER OF SEQ ID NOS: 45

<210> SEQ ID NO 1
<211> LENGTH: 2098
<212> TYPE: DNA
<213> ORGANISM: Nicotiana tabacum

<400> SEQUENCE: 1

```
ccacgcgtcc gcttagggtt ccaaattgct ctaaattccc gcggattgag agttcattgg      60
agacttccat tgttcccagc ggctaagatg agccggttga ttgagcatca cctagcaaat     120
aataaacagg acatgaaagg dacagaggtt tttgttggtg gtttggcccg tactactact     180
gaaagcaaaa ttcatgaggt attttcttca tgtggtgaga ttgtggaaat acggttgata     240
aaagaccaga caggcgttcc taaggggttt tgctttgtac gatttgcaac aaaatatgct     300
gctgacaaag ctctgaagga aaaatctgga tatgtgctgg atgggaagaa actcggggtt     360 cgccctcag ttgagcagga cactttattt cttggaaatc ttaacaaagg ttggggtgcg     420
gaggaatttg agagtattgt gcgccaggtt tttccagatg ttgtatctgt tgatcttgca     480
cttcttggag atgtccaacc tggtcagaag caacggaatc ggggttttgc tttcgtgaaa     540
ttcccatctc atgctgctgc ggctcgtgct tttcgggtag gctcccaatc tgattttctc     600
attgatggca agttacatcc atctgtacag tgggctgagg aacctgatcc caatgaactt     660
gctcagatca aagcagcctt cgttagaaat gtacctcctg gtgctgatga agattacttg     720
aagaagctct ttcagccctt tggcaatgta gagaggatag ctctatccag gaaaggtagc     780
tccaccattg gattcgttta cttcgataag cgatctgatc ttgacaatgc tattatggcg     840
ttgaatgaga aaactgtaca agggccaatg ggaggtccct catgcaagct tcaggtcgaa     900
gttgctaggc caatggacaa gaacaggaaa cgaggtcgtg aggatccaaa catgtccagt     960
accattgaga gtcattccaa gcttttgaag gatgatccag atgttgagat gattagggct    1020
cctaaatcaa ctgctcaact ggagatggat tattcggatc cttatgaagc tgctgtagtt    1080
gcattacctg tggttgtcaa ggagcgttta gttcggatct gcggcttgg tattgctact    1140 agatatgata tagatgttga aagtttaacc agtcttaaga tattgcccca gtcagctgcc    1200
atatctattc ttgaccagtt catgttgtct ggagctgata tgcagaacaa gggaggatat    1260
ctagcttcat taatttctaa gcaggttgaa aaactgggac cgaaacaatt cgatagtagg    1320
tcaaggatag aagatgttgg cttgagggtg ccagaaccag acaggttctc tacaagagtt    1380
cgtttgccag atctagattc atatgcctca cgagtaccct tgcccatgcc taggactgat    1440
gtttacacat ctcactattc agcgtattta gatcccatc tgtctggtcg gatgacagca    1500
aagaggatgg aggaagcaag ttcccatttg caggcgactt cacttctgtc tagtcgggtg    1560
```

```
gcaacgagga tggaggaggc aggttccact ttgcagtcgc tcctatctgg tggggtgacg   1620
acaagaagga tggaggaagc aagtccgatt ttgcaggcaa cactccttcc atctggtcgg   1680
gtatcaagga tggatgaagc aagtcccaat ttgcaggcaa catggagccc ttctcctact   1740
aatgacagaa ttggacttca ttcacacatt accgcaactg ctgatcatca acatactcga   1800
ccacggatca ggtttgatcc cttcactggt gagccataca aatttgaccc cttcactggc   1860
gagccaattg ttcccaagag ctcaagtcat catcgaagcc tgtactgaac gttctgagca   1920
ttctaattta caaatggctt attgccaaac ctatgtaaca aatgatgcg tattttgtt    1980 catccgcagc tgtaaaatag tagctgttag caggattatt tggttatgtt ctcattgac    2040 ttcattgatt gcgaaggtgc atttggaatc tcggcaatca caatttatag ccggtgca    2098
```

<210> SEQ ID NO 2
<211> LENGTH: 606
<212> TYPE: PRT
<213> ORGANISM: Nicotiana tabacum

<400> SEQUENCE: 2

```
Met Ser Arg Leu Ile Glu His His Leu Ala Asn Asn Lys Gln Asp Met
 1               5                   10                  15

Lys Gly Thr Glu Val Phe Val Gly Gly Leu Ala Arg Thr Thr Thr Glu
            20                  25                  30

Ser Lys Ile His Glu Val Phe Ser Ser Cys Gly Glu Ile Val Glu Ile
        35                  40                  45

Arg Leu Ile Lys Asp Gln Thr Gly Val Pro Lys Gly Phe Cys Phe Val
    50                  55                  60

Arg Phe Ala Thr Lys Tyr Ala Ala Asp Lys Ala Leu Lys Glu Lys Ser
65                  70                  75                  80

Gly Tyr Val Leu Asp Gly Lys Lys Leu Gly Val Arg Pro Ser Val Glu
                85                  90                  95

Gln Asp Thr Leu Phe Leu Gly Asn Leu Asn Lys Gly Trp Gly Ala Glu
            100                 105                 110

Glu Phe Glu Ser Ile Val Arg Gln Val Phe Pro Asp Val Val Ser Val
        115                 120                 125

Asp Leu Ala Leu Leu Gly Asp Val Gln Pro Gly Gln Lys Gln Arg Asn
    130                 135                 140

Arg Gly Phe Ala Phe Val Lys Phe Pro Ser His Ala Ala Ala Ala Arg
145                 150                 155                 160

Ala Phe Arg Val Gly Ser Gln Ser Asp Phe Leu Ile Asp Gly Lys Leu
                165                 170                 175

His Pro Ser Val Gln Trp Ala Glu Glu Pro Asp Pro Asn Glu Leu Ala
            180                 185                 190

Gln Ile Lys Ala Ala Phe Val Arg Asn Val Pro Pro Gly Ala Asp Glu
        195                 200                 205

Asp Tyr Leu Lys Lys Leu Phe Gln Pro Phe Gly Asn Val Glu Arg Ile
    210                 215                 220

Ala Leu Ser Arg Lys Gly Ser Ser Thr Ile Gly Phe Val Tyr Phe Asp
225                 230                 235                 240

Lys Arg Ser Asp Leu Asp Asn Ala Ile Met Ala Leu Asn Glu Lys Thr
                245                 250                 255

Val Gln Gly Pro Met Gly Gly Pro Ser Cys Lys Leu Gln Val Glu Val
            260                 265                 270

Ala Arg Pro Met Asp Lys Asn Arg Lys Arg Gly Arg Glu Asp Pro Asn
        275                 280                 285
```

```
Met Ser Ser Thr Ile Glu Ser His Ser Lys Leu Leu Lys Asp Asp Pro
    290                 295                 300

Asp Val Glu Met Ile Arg Ala Pro Lys Ser Thr Ala Gln Leu Glu Met
305                 310                 315                 320

Asp Tyr Ser Asp Pro Tyr Glu Ala Ala Val Val Ala Leu Pro Val Val
                325                 330                 335

Val Lys Glu Arg Leu Val Arg Ile Leu Arg Leu Gly Ile Ala Thr Arg
            340                 345                 350

Tyr Asp Ile Asp Val Glu Ser Leu Thr Ser Lys Ile Leu Pro Gln
        355                 360                 365

Ser Ala Ala Ile Ser Ile Leu Asp Gln Phe Met Leu Ser Gly Ala Asp
    370                 375                 380

Met Gln Asn Lys Gly Gly Tyr Leu Ala Ser Leu Ile Ser Lys Gln Val
385                 390                 395                 400

Glu Lys Leu Gly Pro Lys Gln Phe Asp Ser Arg Ser Arg Ile Glu Asp
                405                 410                 415

Val Gly Leu Arg Val Pro Glu Pro Asp Arg Phe Ser Thr Arg Val Arg
            420                 425                 430

Leu Pro Asp Leu Asp Ser Tyr Ala Ser Arg Val Pro Leu Pro Met Pro
        435                 440                 445

Arg Thr Asp Val Tyr Thr Ser His Tyr Ser Ala Tyr Leu Asp Pro His
    450                 455                 460

Leu Ser Gly Arg Met Thr Ala Lys Arg Met Glu Glu Ala Ser Ser His
465                 470                 475                 480

Leu Gln Ala Thr Ser Leu Leu Ser Ser Arg Val Ala Thr Arg Met Glu
                485                 490                 495

Glu Ala Gly Ser Thr Leu Gln Ser Leu Leu Ser Gly Val Thr Thr
            500                 505                 510

Arg Arg Met Glu Glu Ala Ser Pro Ile Leu Gln Ala Thr Leu Leu Pro
        515                 520                 525

Ser Gly Arg Val Ser Arg Met Asp Glu Ala Ser Pro Asn Leu Gln Ala
    530                 535                 540

Thr Trp Ser Pro Ser Pro Thr Asn Asp Arg Ile Gly Leu His Ser His
545                 550                 555                 560

Ile Thr Ala Thr Ala Asp His Gln His Thr Arg Pro Arg Ile Arg Phe
                565                 570                 575

Asp Pro Phe Thr Gly Glu Pro Tyr Lys Phe Asp Pro Phe Thr Gly Glu
            580                 585                 590

Pro Ile Val Pro Lys Ser Ser Ser His His Arg Ser Leu Tyr
        595                 600                 605
```

<210> SEQ ID NO 3
<211> LENGTH: 1103
<212> TYPE: DNA
<213> ORGANISM: Oryza sativa

<400> SEQUENCE: 3

```
atggtgcgtg ctcgagactc aatccgcgaa atcctccctg ttttttcgat tcaatccgcc    60
ctggggacgg cggattcggc gccggcgatc cggccggtcg ccgccgcgtc cgatttggtg   120
cggatttcgt cggagaaatc gcgtcttgac cttcctgtgc ctcttttttt ttttgttgct   180
cgtgggggat tcaggagaa gagggggggcg gcgtcgcatg gcgactacga cgagcaaggt   240
tattggatgg gttcttctc tttgataccct cgagcgagtc ttgcgttgcg tgggtgaaag   300
gcgccgaggt gttcgtcggc gggttgccgc ggtcggtgac ggagcgggcg ctccgagagg   360
```

```
ttggtgttct tccgagaggt gtaatctcaa caggtatttt ctccttgtgg agagattgtt      420
gatttgcgga taatgaaaga tcagaatggc atttcaaagt ggttctctgc cagcttcaag      480
gaaagagact tgctgttgat ctttcgttgg atcaagatac actcttcttt gggaatcttt      540
gcaaaggtag tcagactggg gcatcgaaga atttgaagaa ttgattcgca aggtaagacc      600
tgtaggttga ccttgcaatg gctcgaaacc atgactcttc agttgggaaa agacgtctaa      660
atcgaggctt tgcatttgtg cgatttctt ctcatgcagt aagtgttgac atgataaccc      720
ttttctgcca atttcttttt ttgcaggtgt ctgatacgga ccctatgaa gcagctgttg       780 tttcactacc ttcagccgtc aaggaactcc tacttcgtat tctacgtctt agaattggca      840
ctcgatatga tgtaagtaat ctgtacataa ggtctctact tgtgcagctc caggtcatct      900
gctgaatact ctactgctcg ccaacaagta aggtttgatc cattcacagg ggaaccatac      960
aagtttgatc cctacaccgg tgaacccatc aggccagaat cgaacccacg tcgctcagga    1020
agcttatact gactttgatt gattgaagca acagtttgga tatggtagat tagatttaca    1080
tccctgaacc aaaaggacca tat                                            1103
```

```
<210> SEQ ID NO 4
<211> LENGTH: 680
<212> TYPE: PRT
<213> ORGANISM: Oryza sativa

<400> SEQUENCE: 4
```

```
Met Val Arg Ala Arg Asp Ser Ile Arg Glu Ile Leu Pro Val Phe Ser
 1               5                  10                  15

Ile Gln Ser Ala Leu Gly Thr Ala Asp Ser Ala Pro Ala Ile Arg Pro
             20                  25                  30

Val Ala Ala Ser Asp Leu Val Arg Ile Ser Ser Glu Lys Ser Arg
         35                  40                  45

Leu Asp Leu Pro Val Pro Leu Phe Phe Val Ala Arg Gly Gly Phe
     50                  55                  60

Gln Glu Lys Arg Gly Ala Ala Ser His Gly Asp Tyr Asp Glu Gln Gly
 65                  70                  75                  80

Tyr Trp Met Gly Phe Phe Ser Leu Ile Pro Arg Ala Ser Leu Ala Leu
                 85                  90                  95

Arg Gly Arg Arg Val Lys Gly Ala Glu Val Phe Val Gly Gly Leu Pro
            100                 105                 110

Arg Ser Val Thr Glu Arg Ala Leu Arg Glu Val Gly Val Leu Pro Arg
        115                 120                 125

Ser Gln Gln Val Phe Ser Pro Cys Gly Glu Ile Val Asp Leu Arg Ile
    130                 135                 140

Met Lys Asp Gln Asn Gly Ile Ser Lys Val Leu Cys Gln Leu Gln Gly
145                 150                 155                 160

Lys Arg Leu Ala Val Asp Leu Ser Leu Asp Gln Asp Thr Leu Phe Phe
                165                 170                 175

Gly Asn Leu Cys Lys Gly Ser Asp Trp Gly Ile Glu Glu Phe Glu Glu
            180                 185                 190

Leu Ile Arg Lys Val Arg Pro Val Val Asp Leu Ala Met Ala Arg Asn
        195                 200                 205

His Asp Ser Ser Val Gly Lys Arg Leu Asn Arg Gly Phe Ala Phe
    210                 215                 220

Val Arg Phe Ser Ser His Ala Val Ser Gln Val Lys Thr Ala Phe Val
225                 230                 235                 240
```

-continued

Gly Asn Leu Pro Ala Asn Val Thr Glu Glu Tyr Leu Arg Lys Leu Phe
            245                 250                 255

Glu His Cys Gly Glu Val Cys Tyr Ala Val Val Arg Val Ala Val Ser
        260                 265                 270

Arg Lys Gly Gln Tyr Pro Val Gly Phe Val His Phe Ala Ser Arg Thr
    275                 280                 285

Trp Lys Glu Leu Asp Asn Ala Ile Lys Glu Met Asp Gly Glu Thr Val
290                 295                 300

Arg Gly Pro Asp Arg Gly Ala Thr Phe Arg Ile Gln Val Ser Val Ala
305                 310                 315                 320

Arg Pro Val Val Glu Asn Asp Lys Lys Arg Ile Arg Glu Glu Val Lys
                325                 330                 335

Thr Arg Arg Ser Asn Val Ser Thr Asp Lys Pro Asp His Ser Tyr Gly
            340                 345                 350

Arg Arg Gly His Asp Ser Tyr Asp Arg Gln Ala Lys Ala Pro Arg Leu
        355                 360                 365

Tyr Asn Glu Val Leu His Thr Asn Asp Lys Val Asp Met Ile Thr Leu
    370                 375                 380

Phe Cys Gln Phe Ser Phe Leu Gln Val Ser Asp Thr Asp Pro Tyr Glu
385                 390                 395                 400

Ala Ala Val Val Ser Leu Pro Ser Ala Val Lys Glu Leu Leu Leu Arg
                405                 410                 415

Ile Leu Arg Leu Arg Ile Gly Thr Arg Tyr Asp Val Ser Asn Leu Tyr
            420                 425                 430

Ile Arg Ser Leu Leu Val Ser Ile Leu Leu Phe Gln Ile Asp Ile His
        435                 440                 445

Cys Ile Arg Ser Leu Asn Glu Leu Pro Glu Lys Ala Ala Val Ala Val
    450                 455                 460

Leu Asn Gln Cys Ser Gln Phe Leu Ile Ser Gly Ala Asp Lys His Asn
465                 470                 475                 480

Lys Gly Asp Tyr Phe Ala Ser Leu Ile Ala Lys Glu Thr Phe Ser Ser
                485                 490                 495

Ala Leu Arg Leu Gln Gly Ser Thr Tyr Leu Pro Arg Asn Pro Glu Ile
            500                 505                 510

Gln Asn Lys Arg Phe Pro His Ser Ser Arg Tyr Ser Ser Leu Gly Asp
        515                 520                 525

Tyr Pro Ser Ser Ser Tyr Val Asp Asp Pro Ala Ser Ser Gln Ser Arg
    530                 535                 540

Asn Arg Arg Tyr Asp Glu Tyr Arg Pro Asp Leu Val Arg Tyr Pro Asp
545                 550                 555                 560

Ser Arg Ser Arg Gln Glu Glu Ile Val Arg Ile Glu Arg Tyr Pro Glu
                565                 570                 575

Pro Arg Phe Ala His Glu Pro Arg Gln Asp Thr Gly Arg His Leu Asp
            580                 585                 590

Leu Gly Tyr Val Gln Glu Arg Asn Ser Asn Ile Glu Arg Ser Ala Gln
        595                 600                 605

Val Ala Phe Ser Ser Arg Glu Gly Gly Tyr Leu Ser Ala Ser Arg Tyr
    610                 615                 620

Asn Thr Asn Ile Val Pro Glu Phe Ser Arg Ser Ser Ala Glu Tyr
625                 630                 635                 640

Ser Thr Ala Arg Gln Gln Val Arg Phe Asp Pro Phe Thr Gly Glu Pro
                645                 650                 655

Tyr Lys Phe Asp Pro Tyr Thr Gly Glu Pro Ile Arg Pro Glu Ser Asn
            660                 665                 670

Pro Arg Arg Ser Gly Ser Leu Tyr
        675                 680

<210> SEQ ID NO 5
<211> LENGTH: 1758
<212> TYPE: DNA
<213> ORGANISM: Zea mays
<220> FEATURE:
<221> NAME/KEY: misc_feature
<222> LOCATION: (1632)..(1632)
<223> OTHER INFORMATION: n is a, c, g, or t
<220> FEATURE:
<221> NAME/KEY: misc_feature
<222> LOCATION: (1699)..(1699)
<223> OTHER INFORMATION: n is a, c, g, or t
<220> FEATURE:
<221> NAME/KEY: misc_feature
<222> LOCATION: (1722)..(1722)
<223> OTHER INFORMATION: n is a, c, g, or t
<220> FEATURE:
<221> NAME/KEY: misc_feature
<222> LOCATION: (1747)..(1747)
<223> OTHER INFORMATION: n is a, c, g, or t
<220> FEATURE:
<221> NAME/KEY: misc_feature
<222> LOCATION: (1754)..(1754)
<223> OTHER INFORMATION: n is a, c, g, or t

<400> SEQUENCE: 5

| | | | | | |
|---|---|---|---|---|---|
| tctagctgtg | ttcttgtggc | tgtgaaatta | tatctcccat | gctgatactt | gattccctta | 60 |
| tctttgcttc | attactacac | cacagtaatt | tggatctgcc | attatgttac | tatgtaactc | 120 |
| tcatttgata | tcaatcacag | ctgccacata | caaaatacaa | gtatgtttat | ctagataaga | 180 |
| tcttgattca | tcaatcacca | ctgatctgag | ttttcgccac | tgcgatgcga | ggaaaagaca | 240 |
| gatatctaat | aacatcttgg | tgaagatgtt | cttaggtcct | ttgctttctc | ttcaagtcag | 300 |
| cttcctttga | tttcattcct | caaactatca | atcacaggct | gcagcacgtg | taatccgcat | 360 |
| cggttcaaga | acagatttca | tgcttggtga | tattttgcat | cctgcgataa | attgggctga | 420 |
| taaagagtct | catctggatc | ctgatgaaat | ggccaagatg | aagtctgctt | ttattggtaa | 480 |
| cctgccagaa | gatgttaatg | aggagtactt | gagaaagctt | tttggacagt | cggtgaggt | 540 |
| agtacgggtt | gctatctcaa | gaaaaggaca | atgtccagtt | gcttttgttc | acttcgccaa | 600 |
| acgttcagag | cttgagaatg | ctatagaaga | aatggatggt | aaaacggtga | aggacctgg | 660 |
| tcgagggccg | tctttcaaga | tccaggtgtc | agttgctcga | cctacggcag | acaacgacaa | 720 |
| gaagcgatct | cgtgaagaag | tgagaactag | aagatcaaat | gcatcaggag | ataggcgaga | 780 |
| ttattctcat | ggaagatatg | acacgattc | acttgatcgt | caagtgaaag | ctccaagatt | 840 |
| atctaattat | gtggccgatg | ctgctgaccc | tatgaatca | gctgttaatt | cattaccttc | 900 |
| agctgtcaag | gaagtcttgc | ttcgaattct | acgtctaaga | attggtactc | gatatgatat | 960 |
| tgatatccat | tgtgttaaaa | gccttgatga | gcttcctgag | tcatctgctc | ttgctgtcct | 1020 |
| taatcagttt | ttgatatcag | gtggagacaa | acacaacaaa | ggagattatt | ttgcatcgtt | 1080 |
| ggttgctaag | caccaggctg | agaccttttgg | cttaacacat | gcattacacg | gtaccactta | 1140 |
| tttgtcaaga | aatccggaaa | tgcatagcaa | gcgataccca | catgaagatt | atgattttgt | 1200 |
| gacacccagg | agcagtaggt | acgattcgtc | agcccatcat | ccttcaacat | actacgaaga | 1260 |
| cgatccacca | gtgtctgagt | caagggttag | aagatatgct | gaagaaaggt | ccaccattgt | 1320 |
| aagaagccca | gaaccacgtc | cgcgatatga | cgaaacagac | ataagaataa | acccagaacc | 1380 |
| aagattacca | tatgaatcaa | gacacaacgc | cgaaaagcat | ctcgatcgaa | gatacataca | 1440 |

```
agagcatagt tcaaatattg aaagaccagc tgaagaagct ctcctttcta gggaaaggag    1500
atttctgcct gctgcagggt acatgccgaa cccaggcggc tcggatttcc gctccaggtc    1560
gcccgccgaa tattcagcac aacgccaaca aatgaggttt gatccattca caggtgaacc    1620
ttacaagttt gnacccttca caggggagcc catcaggcca gatccgaacc cagcgccgct    1680
caggaagcct gtaattgant cagaataagt ttggaagccg anaatgccag attaagaacc    1740
ctgaaancaa agcnaaga                                                  1758
```

<210> SEQ ID NO 6
<211> LENGTH: 448
<212> TYPE: PRT
<213> ORGANISM: Zea mays
<220> FEATURE:
<221> NAME/KEY: misc_feature
<222> LOCATION: (424)..(424)
<223> OTHER INFORMATION: Xaa can be any naturally occurring amino acid
<220> FEATURE:
<221> NAME/KEY: misc_feature
<222> LOCATION: (446)..(446)
<223> OTHER INFORMATION: Xaa can be any naturally occurring amino acid

<400> SEQUENCE: 6

```
Gly Ser Arg Thr Asp Phe Met Leu Gly Asp Ile Leu His Pro Ala Ile
1               5                   10                  15

Asn Trp Ala Asp Lys Glu Ser His Leu Asp Pro Asp Glu Met Ala Lys
            20                  25                  30

Met Lys Ser Ala Phe Ile Gly Asn Leu Pro Glu Asp Val Asn Glu Glu
        35                  40                  45

Tyr Leu Arg Lys Leu Phe Gly Gln Phe Gly Glu Val Val Arg Val Ala
    50                  55                  60

Ile Ser Arg Lys Gly Gln Cys Pro Val Ala Phe Val His Phe Ala Lys
65                  70                  75                  80

Arg Ser Glu Leu Glu Asn Ala Ile Glu Glu Met Asp Gly Lys Thr Val
                85                  90                  95

Arg Gly Pro Gly Arg Gly Pro Ser Phe Lys Ile Gln Val Ser Val Ala
            100                 105                 110

Arg Pro Thr Ala Asp Asn Asp Lys Lys Arg Ser Arg Glu Glu Val Arg
        115                 120                 125

Thr Arg Arg Ser Asn Ala Ser Gly Asp Arg Arg Asp Tyr Ser His Gly
    130                 135                 140

Arg Tyr Gly His Asp Ser Leu Asp Arg Gln Val Lys Ala Pro Arg Leu
145                 150                 155                 160

Ser Asn Tyr Val Ala Asp Ala Ala Asp Pro Tyr Glu Ser Ala Val Asn
                165                 170                 175

Ser Leu Pro Ser Ala Val Lys Glu Val Leu Leu Arg Ile Leu Arg Leu
            180                 185                 190

Arg Ile Gly Thr Arg Tyr Asp Ile Asp Ile His Cys Val Lys Ser Leu
        195                 200                 205

Asp Glu Leu Pro Glu Ser Ser Ala Leu Ala Val Leu Asn Gln Phe Leu
    210                 215                 220

Ile Ser Gly Gly Asp Lys His Asn Lys Gly Asp Tyr Phe Ala Ser Leu
225                 230                 235                 240

Val Ala Lys His Gln Ala Glu Thr Phe Gly Leu Thr His Ala Leu His
                245                 250                 255

Gly Thr Thr Tyr Leu Ser Arg Asn Pro Glu Met His Ser Lys Arg Tyr
            260                 265                 270

Pro His Glu Asp Tyr Asp Phe Val Thr Pro Arg Ser Ser Arg Tyr Asp
```

|  |  |  | 275 |  |  |  | 280 |  |  |  | 285 |  |  |
|--|--|--|--|--|--|--|--|--|--|--|--|--|--|

Ser Ser Ala His His Pro Ser Thr Tyr Tyr Glu Asp Asp Pro Pro Val
290                     295                     300

Ser Glu Ser Arg Val Arg Arg Tyr Ala Glu Glu Arg Ser Thr Ile Val
305                     310                     315                 320

Arg Ser Pro Glu Pro Arg Pro Arg Tyr Asp Glu Thr Asp Ile Arg Ile
                    325                     330                     335

Asn Pro Glu Pro Arg Leu Pro Tyr Glu Ser Arg His Asn Ala Glu Lys
                340                     345                     350

His Leu Asp Arg Arg Tyr Ile Gln Glu His Ser Ser Asn Ile Glu Arg
            355                     360                     365

Pro Ala Glu Glu Ala Leu Leu Ser Arg Glu Arg Arg Phe Leu Pro Ala
        370                     375                     380

Ala Gly Tyr Met Pro Asn Pro Gly Gly Ser Asp Phe Arg Ser Arg Ser
385                     390                     395                 400

Pro Ala Glu Tyr Ser Ala Gln Arg Gln Gln Met Arg Phe Asp Pro Phe
                    405                     410                     415

Thr Gly Glu Pro Tyr Lys Phe Xaa Pro Phe Thr Gly Glu Pro Ile Arg
                420                     425                     430

Pro Asp Pro Asn Pro Ala Pro Leu Arg Lys Pro Val Ile Xaa Ser Glu
            435                     440                     445

```
<210> SEQ ID NO 7
<211> LENGTH: 1599
<212> TYPE: DNA
<213> ORGANISM: Oryza sativa

<400> SEQUENCE: 7
atcgatcaca ggctgcagca cgcgtacttc gtattggttc cagaacagat tttctgcttg      60
gtggattgca tccttcaata aattgggctg agaaggagtc tcatgtagat gaggacgaaa     120
tggccaaggt taagacagct ttcgttggaa atttaccagc aaatgttaca gaggagtatt     180
taagaaagct ttttgaacat tgtggagagg tagtacgggt tgcagtctca aggaaaggac     240
aatatccagt tggatttgtc cactttgcca gtcgtacaga gctcgacaat gcaataaaag     300
aaatggatgg tgaaacagtg agaggacctg accgaggggc aactttcagg atccaggtct     360
cagttgctcg gcctgtggta gagaacgata aaaagagaat tcgtgaagaa gtgaaaacta     420
gaagatcaaa cgtatcaaca gacaagccgg accattctta tggaagacgt ggacatgatt     480
catatgatcg tcaagcaaaa gctccaaggc tatataatga ggtgtctgat acggacccct     540
atgaagcagc tgttgtttca ctaccttcag ccgtcaagga actcctactt cgtattctac     600
gtcttagaat tggcactcga tatgatatag acattcattg cataaggagt cttaatgaac     660
ttcctgaaaa ggctgcagtt gctgtcctta atcagttttt gatatcaggt gcagataaac     720
acaataaagg agactatttc gcttcattaa ttgctaagta ccaggctgag acatttagct     780
cagcactaag attgcagggt tctacttatt tgccaagaaa tcctggaata cagaacaaga     840
gattcccaca tcaagattac gagtacacag catccgggag tagtagatac agttccttag     900
gtgattatcc ttcctcatct tatgtggatg atcccgcatc atctcagtca aggaatagaa     960
ggtatgatga atacagacct gatccttgta agatatccaga ttcaagatca cggcaagagg    1020
aaatagtccg cattgaaaga tatccagaac caagatttgc acatgaacca agacaggata    1080
ctggaaggca tctcgatcta gggtacgtac aagaacggaa ttcgaatatt gagagatcag    1140
ctcaagtagc ttttttcatct agggaaggag gatacttatc tgcttcaagg tacaacacaa    1200
```

-continued

```
acatagtccc agaattcagc tccaggtcat ctgctgaata ctctactgct cgccaacaag    1260
taaggtttga tccattcaca ggggaaccat acaagtttga tccctacacc ggtgaaccca    1320
tcaggccaga atcgaaccca cgtcgctcag gaagcttata ctgactttga ttgattgaag    1380
caacagtttg gatatggtag attagattta catccctgaa ccaaaaggac catatactgc    1440
tcttgcatgt tgtaaaccta gtgtatttga tgtgcctcag cattgtaatg ttagaaatcc    1500
attttcatcc atgtcactgg aaaactatgg ttgaaacaac agtaataagt tctatcattt    1560
atgatggcat ctgatgatat gaattaggga aaactaagc                           1599
```

<210> SEQ ID NO 8
<211> LENGTH: 414
<212> TYPE: PRT
<213> ORGANISM: Oryza sativa

<400> SEQUENCE: 8

```
Met Ala Lys Val Lys Thr Ala Phe Val Gly Asn Leu Pro Ala Asn Val
1               5                   10                  15

Thr Glu Glu Tyr Leu Arg Lys Leu Phe Glu His Cys Gly Glu Val Val
                20                  25                  30

Arg Val Ala Val Ser Arg Lys Gly Gln Tyr Pro Val Gly Phe Val His
            35                  40                  45

Phe Ala Ser Arg Thr Glu Leu Asp Asn Ala Ile Lys Glu Met Asp Gly
        50                  55                  60

Glu Thr Val Arg Gly Pro Asp Arg Gly Ala Thr Phe Arg Ile Gln Val
65                  70                  75                  80

Ser Val Ala Arg Pro Val Val Glu Asn Asp Lys Lys Arg Ile Arg Glu
                85                  90                  95

Glu Val Lys Thr Arg Arg Ser Asn Val Ser Thr Asp Lys Pro Asp His
                100                 105                 110

Ser Tyr Gly Arg Arg Gly His Asp Ser Tyr Asp Arg Gln Ala Lys Ala
            115                 120                 125

Pro Arg Leu Tyr Asn Glu Val Ser Asp Thr Asp Pro Tyr Glu Ala Ala
        130                 135                 140

Val Val Ser Leu Pro Ser Ala Val Lys Glu Leu Leu Arg Ile Leu
145                 150                 155                 160

Arg Leu Arg Ile Gly Thr Arg Tyr Asp Ile Asp Ile His Cys Ile Arg
                165                 170                 175

Ser Leu Asn Glu Leu Pro Glu Lys Ala Ala Val Ala Val Leu Asn Gln
                180                 185                 190

Phe Leu Ile Ser Gly Ala Asp Lys His Asn Lys Gly Asp Tyr Phe Ala
            195                 200                 205

Ser Leu Ile Ala Lys Tyr Gln Ala Glu Thr Phe Ser Ser Ala Leu Arg
        210                 215                 220

Leu Gln Gly Ser Thr Tyr Leu Pro Arg Asn Pro Gly Ile Gln Asn Lys
225                 230                 235                 240

Arg Phe Pro His Gln Asp Tyr Glu Tyr Thr Ala Ser Gly Ser Arg
                245                 250                 255

Tyr Ser Ser Leu Gly Asp Tyr Pro Ser Ser Tyr Val Asp Asp Pro
                260                 265                 270

Ala Ser Ser Gln Ser Arg Asn Arg Arg Tyr Asp Glu Tyr Arg Pro Asp
            275                 280                 285

Leu Val Arg Tyr Pro Asp Ser Arg Ser Arg Gln Glu Glu Ile Val Arg
        290                 295                 300

Ile Glu Arg Tyr Pro Glu Pro Arg Phe Ala His Glu Pro Arg Gln Asp
```

```
      305                 310                 315                 320
Thr Gly Arg His Leu Asp Leu Gly Tyr Val Gln Glu Arg Asn Ser Asn
                325                 330                 335
Ile Glu Arg Ser Ala Gln Val Ala Phe Ser Ser Arg Glu Gly Gly Tyr
            340                 345                 350
Leu Ser Ala Ser Arg Tyr Asn Thr Asn Ile Val Pro Glu Phe Ser Ser
        355                 360                 365
Arg Ser Ser Ala Glu Tyr Ser Thr Ala Arg Gln Gln Val Arg Phe Asp
    370                 375                 380
Pro Phe Thr Gly Glu Pro Tyr Lys Phe Asp Pro Tyr Thr Gly Glu Pro
385                 390                 395                 400
Ile Arg Pro Glu Ser Asn Pro Arg Arg Ser Gly Ser Leu Tyr
                405                 410

<210> SEQ ID NO 9
<211> LENGTH: 1842
<212> TYPE: DNA
<213> ORGANISM: Oryza sativa

<400> SEQUENCE: 9
atggaaccga cgcgccgttg cgtccccggc catctcgcca ccgccgccgc cgccgccgcc      60
gcctcgccgt tctccccgcc gccgtcgctg ccgctgccgt ccgcgctcat gccccccaag     120
aagcgccgcc tcttcacgcc cgcccctcgc cacgccgcca cccgccacc accaccacct     180 cccccaccc cgccgtcga gcccacccta ccaatccccc cgcctcgac accgccgacg     240 ccgcctcagc cctccgcctc cacggagccc tcgacggcgc cgcctcccgc tgtcgacgac     300
gcggcggcga gtcgtcgtc gtcgtcgtcg ccggcgtcgg cggcggcggc gcggaaggtt     360
cggaaagtgg ttaagaaggt catcgtcaag aaggtcgtcc ccaagggcac gttcgccgct     420
cggaaggccg cggcggcggc ggttgctgct gctgcggcgg tctccggagc agcagcatca     480
tcggaggcag ggggagaagc cccaaccgac gagccagcaa gtgatcagga cggcggagtt     540
gggaatgagc aaaaattgga tgaatccaaa cctgccacgg attgcaatgc cgttgcggtg     600
gtggaagaat cggtgtgtaa ggaggaggag gaggtggcct tagtggtggg taagggagtg     660
gaggaggagg aggcggggat gtcggagcgg cggaagagga tgaccatgga ggtgtttgtt     720
ggtgggcttc accgggacgc caaggaggat gatgtgaggc ggtgttcgc caaggccggg     780 gaaatcaccg aggtccggat gataatgaat cctcttgcag ggaagaacaa ggggtactgc     840
ttcgtgcgct accgccacgc cgcgcaggcg aagaaggcca tcgcggaatt cggcaatgtg     900
aagatttgtg ggaagctctg tcgagctgca gttccagttg ggaatgacag aatttttctt     960
ggaaacatca acaagaaatg gaaaaaagaa gatgtcatca agcagctaaa gaaaattgga    1020
attgagaaca ttgattctgt aacacttaag tctgattcaa ataatccagt ctgtaatcgt    1080
ggttttgcat ttcttgaact ggaaactagt agagatgcac ggatggcata caaaaagctt    1140
tcacagaaaa atgcttttgg caaaggcctg aatataagag ttgcatgggc tgaaccattg    1200
aatgatccag atgagaaaga tatgcaggtt aaatcgattt tgtggatgg gataccaacg    1260 tcctgggatc atgctcagct aaaagaaatc ttcaagaaac atgggaagat tgaaagtgtg    1320
gttctgtcac gcgatatgcc gtcagctaaa aggagggact tgcctttat taattacatt    1380 actcgtgagg ctgcaatctc gtgtcttgaa tcttttgaca aggaagagtt cagtaagaac    1440
ggctcaaagg tgaatattaa agtttcattg gctaaacctg cccaacgag caagcagacc    1500 aaggaagacc ataaatctag tattactggg gaaggcaaaa tgaagacttc taaaataaga    1560
```

-continued

```
taccctgttc aagattatac ccacatttat tctggagaga agcgtcccct ttcaacactg    1620
ggtgatcctt attatccatt gagaggtcat tcttgtcgtc gtcatgaggg tagcacctat    1680
actacagcag catcaagcta tggtgcgctg ccccctgcta ctgctgaatc ttctctgcca    1740
cattatcatg acagcaatag atatcctcca cacctaggtg aggcaatcaa gttctcgcca    1800
accagcgcag tcctatcgaa gcaggcatgg caaaaaatgt aa                        1842
```

<210> SEQ ID NO 10
<211> LENGTH: 613
<212> TYPE: PRT
<213> ORGANISM: Oryza sativa

<400> SEQUENCE: 10

```
Met Glu Pro Thr Arg Arg Cys Val Pro Gly His Leu Ala Thr Ala Ala
1               5                   10                  15

Ala Ala Ala Ala Ser Pro Phe Ser Pro Pro Ser Leu Pro Leu
            20                  25                  30

Pro Ser Ala Leu Met Pro Pro Lys Lys Arg Leu Phe Thr Pro Ala
        35                  40                  45

Pro Arg His Ala Ala Thr Pro Pro Pro Pro Pro Pro Thr Pro
    50                  55                  60

Ala Val Glu Pro Thr Leu Pro Ile Pro Pro Ala Ser Thr Pro Thr
65                  70                  75                  80

Pro Pro Gln Pro Ser Ala Ser Thr Glu Pro Ser Thr Ala Pro Pro
            85                  90                  95

Ala Val Asp Asp Ala Ala Ala Arg Ser Ser Ser Ser Pro Ala
        100                 105                 110

Ser Ala Ala Ala Arg Lys Val Arg Lys Val Val Lys Val Ile
    115                 120                 125

Val Lys Lys Val Val Pro Lys Gly Thr Phe Ala Ala Arg Lys Ala Ala
130                 135                 140

Ala Ala Val Ala Ala Ala Ala Val Ser Gly Ala Ala Ala Ser
145                 150                 155                 160

Ser Glu Ala Gly Gly Glu Ala Pro Thr Asp Glu Pro Ala Ser Asp Gln
                165                 170                 175

Asp Gly Gly Val Gly Asn Glu Gln Lys Leu Asp Glu Ser Lys Pro Ala
            180                 185                 190

Thr Asp Cys Asn Ala Val Ala Val Glu Glu Ser Val Cys Lys Glu
        195                 200                 205

Glu Glu Glu Val Ala Leu Val Val Gly Lys Gly Val Glu Glu Glu
    210                 215                 220

Ala Gly Met Ser Glu Arg Arg Lys Arg Met Thr Met Glu Val Phe Val
225                 230                 235                 240

Gly Gly Leu His Arg Asp Ala Lys Glu Asp Asp Val Arg Ala Val Phe
                245                 250                 255

Ala Lys Ala Gly Glu Ile Thr Glu Val Arg Met Ile Met Asn Pro Leu
            260                 265                 270

Ala Gly Lys Asn Lys Gly Tyr Cys Phe Val Arg Tyr Arg His Ala Ala
        275                 280                 285

Gln Ala Lys Lys Ala Ile Ala Glu Phe Gly Asn Val Lys Ile Cys Gly
    290                 295                 300

Lys Leu Cys Arg Ala Ala Val Pro Val Gly Asn Asp Arg Ile Phe Leu
305                 310                 315                 320

Gly Asn Ile Asn Lys Lys Trp Lys Lys Glu Asp Val Ile Lys Gln Leu
                325                 330                 335
```

```
Lys Lys Ile Gly Ile Glu Asn Ile Asp Ser Val Thr Leu Lys Ser Asp
            340                 345                 350

Ser Asn Asn Pro Val Cys Asn Arg Gly Phe Ala Phe Leu Glu Leu Glu
        355                 360                 365

Thr Ser Arg Asp Ala Arg Met Ala Tyr Lys Lys Leu Ser Gln Lys Asn
    370                 375                 380

Ala Phe Gly Lys Gly Leu Asn Ile Arg Val Ala Trp Ala Glu Pro Leu
385                 390                 395                 400

Asn Asp Pro Asp Glu Lys Asp Met Gln Val Lys Ser Ile Phe Val Asp
                405                 410                 415

Gly Ile Pro Thr Ser Trp Asp His Ala Gln Leu Lys Glu Ile Phe Lys
            420                 425                 430

Lys His Gly Lys Ile Glu Ser Val Val Leu Ser Arg Asp Met Pro Ser
        435                 440                 445

Ala Lys Arg Arg Asp Phe Ala Phe Ile Asn Tyr Ile Thr Arg Glu Ala
    450                 455                 460

Ala Ile Ser Cys Leu Glu Ser Phe Asp Lys Glu Glu Phe Ser Lys Asn
465                 470                 475                 480

Gly Ser Lys Val Asn Ile Lys Val Ser Leu Ala Lys Pro Ala Gln Gln
                485                 490                 495

Ser Lys Gln Thr Lys Glu Asp His Lys Ser Ser Ile Thr Gly Glu Gly
            500                 505                 510

Lys Met Lys Thr Ser Lys Ile Arg Tyr Pro Val Gln Asp Tyr Thr His
        515                 520                 525

Ile Tyr Ser Gly Glu Lys Arg Pro Phe Ser Thr Leu Gly Asp Pro Tyr
    530                 535                 540

Tyr Pro Leu Arg Gly His Ser Cys Arg Arg His Glu Gly Ser Thr Tyr
545                 550                 555                 560

Thr Thr Ala Ala Ser Ser Tyr Gly Ala Leu Pro Pro Ala Thr Ala Glu
                565                 570                 575

Ser Ser Leu Pro His Tyr His Asp Ser Asn Arg Tyr Pro Pro His Leu
            580                 585                 590

Gly Glu Ala Ile Lys Phe Ser Pro Thr Ser Ala Val Leu Ser Lys Gln
        595                 600                 605

Ala Trp Gln Lys Met
    610

<210> SEQ ID NO 11
<211> LENGTH: 654
<212> TYPE: DNA
<213> ORGANISM: Oryza sativa

<400> SEQUENCE: 11
cttctacatc ggcttaggtg tagcaacacg actttattat tattattatt attattatta      60
ttattttaca aaatataaa atagatcagt ccctcaccac aagtagagca agttggtgag     120
ttattgtaaa gttctacaaa gctaatttaa aagttattgc attaacttat ttcatattac     180
aaacaagagt gtcaatggaa caatgaaaac catatgacat actataattt tgtttttatt     240
attgaaatta tataattcaa agagaataaa tccacatagc cgtaaagttc tacatgtggt     300
gcattaccaa aatatatata gcttacaaaa catgacaagc ttagtttgaa aaattgcaat     360
ccttatcaca ttgacacata aagtgagtga tgagtcataa tattattttc tttgctaccc     420
atcatgtata tatgatagcc acaaagttac tttgatgatg atatcaaaga acattttag      480 gtgcacctaa cagaatatcc aaataatatg actcacttag atcataatag agcatcaagt     540
```

```
aaaactaaca ctctaaagca accgatggga aagcatctat aaatagacaa gcacaatgaa    600
aatcctcatc atccttcacc acaattcaaa tattatagtt gaagcatagt agta          654
```

<210> SEQ ID NO 12
<211> LENGTH: 30
<212> TYPE: PRT
<213> ORGANISM: Artificial sequence
<220> FEATURE:
<223> OTHER INFORMATION: motif I - consensus sequence

<400> SEQUENCE: 12

```
Pro Tyr Glu Ala Ala Val Val Ala Leu Pro Val Val Lys Glu Arg
 1               5                  10                  15

Leu Val Arg Ile Leu Arg Leu Gly Ile Ala Thr Arg Tyr Asp
            20                  25                  30
```

<210> SEQ ID NO 13
<211> LENGTH: 14
<212> TYPE: PRT
<213> ORGANISM: Artificial sequence
<220> FEATURE:
<223> OTHER INFORMATION: motif II - consensus sequence

<400> SEQUENCE: 13

```
Arg Phe Asp Pro Phe Thr Gly Glu Pro Tyr Lys Phe Asp Pro
 1               5                  10
```

<210> SEQ ID NO 14
<211> LENGTH: 2166
<212> TYPE: DNA
<213> ORGANISM: Arabidopsis thaliana

<400> SEQUENCE: 14

```
aagatttggg cttacaatct ttatcacaaa ggctttttta aagcccatta gttacattca     60
tcattatctc tcgacattaa aaaaaaaaag ttaaactgaa gaagctaaaa agagttttta    120
acttttaact ctcttcgtct tctccctcgt gccgtgtcaa atcaatctac tgttctctct    180
cctatctggt aaacttttcc tcttcgccat gaaattttt tcttgctagg gttttagttt     240
ctacagttcg cttcccaaaa attaggggtt ttgtcacaat ttctcaattt cttgttccat    300 tttttcttctt ttctccataa tcattgctta atttagaatc ccaaatttta caaattaggg   360
tttttgttta atttaggggg tttttgattt tcaactgtta atagtgttct cgatgtcata    420
attctgattt tttttattat ctattccgaa attagggcaa aaatctcaga caaacctgca    480
aaattagggt atttgaggat atggattatg atcggtacaa gttatttgtt ggtggtattg    540
cgaaagagac aagtgaagaa gctctgaagc agtattttag cagatatgga gctgtgttgg    600
aagctgttgt agctaaagag aaagtcactg gaaaacctag aggttttggg tttgttcgct    660 tgctaatga ttgtgatgtt gttaaagctc ttagagacac tcacttcatt ctcggtaaac     720
ccgtaagtgt taccgccttt ttatgcttgt gtcaattggg ttttgtgtat actctgtgga    780
ttgattatgt gtgtgtttgt attaggttga tgtgagaaag gcgattagga aacatgaact    840
ataccaacag ccgtttagca tgcagttttt ggagagaaaa gtgcaacaga tgaatggtgg    900
tttgcgtgag atgtcgagta atggtgtgac cagtaggact aagaagatat ttgttggggg    960
tttgtcgtct aacacgactg aggaagagtt taagagttac tttgagaggt ttggtaggac   1020
tactgatgta gttgtgatgc atgacggtgt gactaacagg ccaagggggtt ttgggtttgt   1080 tacttatgat tcggaggact ctgttgaggt tgttatgcag agtaatttcc atgagttgag   1140
```

```
tgataaacgc gtggaagtga acgggcaat acctaaagaa ggaatccaga gcaataacgg    1200
taatgctgtt aatattcctc cttcctacag cagctttcaa gcaacacctt atgtccctga    1260
gcaaaacgga tatgggatgg ttttacagtt tcctcctcct gtctttggtt atcatcacaa    1320
tgtccaagcc gttcaatatc cttatggtta ccaattcaca gcacaagtgg ctaacgtttc    1380
atggaacaat ccgattatgc aacccaccgg ttttactgt gctcctcctc atcctactcc    1440
tcctcccacc aacaatcttg gttatatcca atacatgaac gggtttgatc tttcgggtac    1500
gaacatttcc gggtacaatc tctagcatg gcctgtaacg ggggatgcag ctggtgcgct    1560
aatacatcag tttgtagatt tgaagcttga tgtccacagt caagcccatc agagaatgaa    1620
tggaggtaac atgggaatac cattgcagaa tggtacatat atatgacagt tgcagaatga    1680
taaatgcaaa taggctcaca agggtagtga aattctttgg actcttttaa atggtttttt    1740
aggttcctca tctttcttca ttaactcttt ggtaaatgtg ttgggttggt ttggttacct    1800
tgtatattgt ttaggtattt gattttaacc ccaagactta tgtatcatat attactgcat    1860
ttgtaatata tcacactcat ttagttcatt ttgttgcttt tatggttttg ttgattttgt    1920
ggtttcgttg attaaattgg caatgatgtt ttaaattcat caaggaaaac aaagaaatag    1980
attgtcgatt aaacagtaga aaaaggaaat agttttgtag aaataggaac tgaatctgga    2040
aatctctaag aataccatat tgtagaaaga aaataaatct gagacgggag aaactatcga    2100
gcatccttga gctttaagtt ggagaaaccg ggtaagcgtt tgtgggattt tgttgtaaga    2160
ttgaac                                                                2166

<210> SEQ ID NO 15
<211> LENGTH: 360
<212> TYPE: PRT
<213> ORGANISM: Arabidopsis thaliana

<400> SEQUENCE: 15

Met Asp Tyr Asp Arg Tyr Lys Leu Phe Val Gly Gly Ile Ala Lys Glu
1               5                   10                  15

Thr Ser Glu Glu Ala Leu Lys Gln Tyr Phe Ser Arg Tyr Gly Ala Val
            20                  25                  30

Leu Glu Ala Val Val Ala Lys Glu Lys Val Thr Gly Lys Pro Arg Gly
        35                  40                  45

Phe Gly Phe Val Arg Phe Ala Asn Asp Cys Asp Val Val Lys Ala Leu
    50                  55                  60

Arg Asp Thr His Phe Ile Leu Gly Lys Pro Val Asp Val Arg Lys Ala
65                  70                  75                  80

Ile Arg Lys His Glu Leu Tyr Gln Gln Pro Phe Ser Met Gln Phe Leu
                85                  90                  95

Glu Arg Lys Val Gln Gln Met Asn Gly Gly Leu Arg Glu Met Ser Ser
            100                 105                 110

Asn Gly Val Thr Ser Arg Thr Lys Lys Ile Phe Gly Gly Leu Ser
        115                 120                 125

Ser Asn Thr Thr Glu Glu Glu Phe Lys Ser Tyr Phe Glu Arg Phe Gly
    130                 135                 140

Arg Thr Thr Asp Val Val Met His Asp Gly Val Thr Asn Arg Pro
145                 150                 155                 160

Arg Gly Phe Gly Phe Val Thr Tyr Asp Ser Glu Asp Ser Val Glu Val
                165                 170                 175

Val Met Gln Ser Asn Phe His Glu Leu Ser Asp Lys Arg Val Glu Val
            180                 185                 190
```

```
Lys Arg Ala Ile Pro Lys Glu Gly Ile Gln Ser Asn Asn Gly Asn Ala
            195                 200                 205
Val Asn Ile Pro Pro Ser Tyr Ser Ser Phe Gln Ala Thr Pro Tyr Val
    210                 215                 220
Pro Glu Gln Asn Gly Tyr Gly Met Val Leu Gln Phe Pro Pro Val
225                 230                 235                 240
Phe Gly Tyr His His Asn Val Gln Ala Val Gln Tyr Pro Tyr Gly Tyr
                245                 250                 255
Gln Phe Thr Ala Gln Val Ala Asn Val Ser Trp Asn Asn Pro Ile Met
            260                 265                 270
Gln Pro Thr Gly Phe Tyr Cys Ala Pro Pro His Pro Thr Pro Pro
        275                 280                 285
Thr Asn Asn Leu Gly Tyr Ile Gln Tyr Met Asn Gly Phe Asp Leu Ser
290                 295                 300
Gly Thr Asn Ile Ser Gly Tyr Asn Pro Leu Ala Trp Pro Val Thr Gly
305                 310                 315                 320
Asp Ala Ala Gly Ala Leu Ile His Gln Phe Val Asp Leu Lys Leu Asp
                325                 330                 335
Val His Ser Gln Ala His Gln Arg Met Asn Gly Gly Asn Met Gly Ile
            340                 345                 350
Pro Leu Gln Asn Gly Thr Tyr Ile
        355                 360

<210> SEQ ID NO 16
<211> LENGTH: 3041
<212> TYPE: DNA
<213> ORGANISM: Arabidopsis thaliana

<400> SEQUENCE: 16
cttcattgag agagagatat agagagagaa aagagagaga ggccatattt tgataagaga      60
agaagaaccc ttatagagaa agagaaagag agagacagag agagtggatg gatgtcttat     120
agaatgaaca aaacatcctc tgtttctctt gtccttgtcc cttttccag atcttaaggt     180
tttccacatt ttatcatctg gtcctctcc ttaatggtga attctccatc tttacaagtt     240
tgatgttttt gttcatcaaa tctggcgttt ttttttctct tctaatatat attgtctctg     300
ctcatttttcc gtttctcttc ccattgattg ttctgtttca tttctgtttt ttttttttca     360
atagttttga ttggatgctt tgatgatcca ttgtcagatt tgaagacact caattcctat     420
ttgatcgggg actagaattt ggattctgtt tcagacaaaa gtagatttcc ctgtctcttt     480
cccgtttgat tttcaataag atgaatccgg aggtaaaaca ttgaacaatt cttcataaat     540
ctcagaactt tgagcttttt tgaatcttaa aacacgatcg aagtaaaaaa tcgaattgtt     600
agatgaaatg ggcaatcgtc attttcgcaa atctgatccg tatttgtgag atcggattca     660
ttggatcgac tttggggttt tgcaggagca aaagatggaa tctgcatcgg atctgggcaa     720
gctcttcatt ggcgggattt catgggacac agatgaagaa cgactgcaag agtattttgg     780
caagtatgga gatttggttg aagctgtgat catgagagac cgtactaccg gacgtgcccg     840
tggctttggg tttatcgttt tgcagatcc ttctgttgcc gagagagtca tcatggacaa     900
acacatcatt gatggccgca cggttagtat tcttggatcc attgcttgac aattcatcta     960
attatcagtc ttgagtaatc gagtgttcta aagtctcgat ctttctgtaa tgattctgtc    1020
ttagaggtct tattggtctc gctgctcgtt aatgagcaac ggattgttct ataatctcga    1080
tctttctgta ttcatgctct cttagagatc tgtttggtgt catccattaa tgagttttaa    1140
gcagcaacgt ttagatcttt ctgtaatcat gctctttcg aaatcttctg ttgtcattag    1200
```

```
cttctggatt tgctgttact gttataactt gtgagaatgt gttgttgctt tgtgttgaag    1260
tggcaatgtt agtgttagat caatgagaaa agaatgaaag atcttttttt atttctttgt    1320
tgcaggtcga ggcgaagaaa gctgtcccgc gggatgatca gcaagtgcta aaacgacacg    1380
ccagtccaat gcaccttatc tcacctagcc atggtggtaa tggtggtgga gcacggacaa    1440
agaagatctt tgttggaggt ttaccgtcta gcattactga ggccgagttc aagaactact    1500
ttgatcagtt tggtacaatt gctgatgttg tggtaatgta tgatcataat acacagaggc    1560
caagaggctt tggcttcatc acttttgatt ccgaagagtc tgttgatatg gttctccaca    1620
agacctttca tgagctaaac ggaaaaatgg ttgaggttaa aagagcagtg ccaaaggagc    1680
tctcctcgac tactcctaac cgaagcccac ttattgggta tggtaacaac tatggagtag    1740
tccctaatag gtcttctgct aatagctact tcaatagttt tcctcctggt tataataata    1800
ataatctagg ctctgctggc cggtttagtc ctattggtag cggtagaaat gctttctcta    1860
gcttcgggct cggattgaat caagaactga atttgaattc aaactttgat ggaaacactc    1920
ttgggtatag ccggatccct ggcaaccaat acttcaacag tgcttcacca aaccgttaca    1980
actctccaat tgggtacaac agaggagact ctgcttacaa cccgagcaac agagacttgt    2040
ggggaaacag aagcgattcc tctggtccag gttggaactt gggagtttcg gttggtaaca    2100
acagaggaaa ctgggacttt cttctgtgg tgagcgataa caatggctat ggaagaagct    2160
atggggctgg ttctggactt tcggggttat cattcgcggg taatacaaac ggttttgatg    2220
gctctatagg ggaattgtat agaggcagct cagtttatag cgactcaaca tggcagcagt    2280
caatgcctca tcatcagtct tctaatgagt tagacggctt gtctcgctct tatggctttg    2340
gtattgacaa tgtaggctca gacccatcag ccaatgcctc agaaggatac tccggaaact    2400
acaatgtcgg aaatagacaa acacatagag gtacactcat cgatgtcaaa cttttttcct    2460
tttgcatctc atctgctaca tttatttttg cctgttgaaa agtaattaga ttgattaacg    2520 tttttcaggta ttgaagcata gaaagaaatc gacgaagaga agtgagaatt gtagatcaag    2580
aagaacagcc atttccgttg cagagtttga agagttgtta tttcgatatc aagtagagaa    2640
agaaaccaac tttcttcatc acagtgagtt tcttgttttg ttttttttcgt cgttagcatc    2700 acaaacacaa aaaagagaag tttattttta ctttaaaaat tcttacataa gataagatca    2760
gattggtagc tgcaaagata caacatggat gataaaaaa gatttggttt cgtctccata    2820
gcaataacca gagatcgttg attctcgatc actattcttt aggtttctct ccttcttctt    2880
ccatgatttc ttgatgttgt gtgctctgtt tgtaactcta attgttaaaa tttttatgt    2940 tacagatttt ttttttcttt tggttttaa actttggatt cgaattgttc atgggaactt    3000 ttggatttt ctattagcgt gagagaaaac acattgtgca a                        3041
```

<210> SEQ ID NO 17
<211> LENGTH: 455
<212> TYPE: PRT
<213> ORGANISM: Arabidopsis thaliana

<400> SEQUENCE: 17

```
Met Asn Pro Glu Glu Gln Lys Met Glu Ser Ala Ser Asp Leu Gly Lys
1               5                   10                  15

Leu Phe Ile Gly Gly Ile Ser Trp Asp Thr Asp Glu Glu Arg Leu Gln
            20                  25                  30

Glu Tyr Phe Gly Lys Tyr Gly Asp Leu Val Glu Ala Val Ile Met Arg
        35                  40                  45
```

Asp Arg Thr Thr Gly Arg Ala Arg Gly Phe Gly Phe Ile Val Phe Ala
50                  55                  60

Asp Pro Ser Val Ala Glu Arg Val Ile Met Asp Lys His Ile Ile Asp
65                  70                  75                  80

Gly Arg Thr Val Glu Ala Lys Lys Ala Val Pro Arg Asp Asp Gln Gln
                85                  90                  95

Val Leu Lys Arg His Ala Ser Pro Met His Leu Ile Ser Pro Ser His
            100                 105                 110

Gly Gly Asn Gly Gly Gly Ala Arg Thr Lys Lys Ile Phe Val Gly Gly
        115                 120                 125

Leu Pro Ser Ser Ile Thr Glu Ala Glu Phe Lys Asn Tyr Phe Asp Gln
    130                 135                 140

Phe Gly Thr Ile Ala Asp Val Val Val Met Tyr Asp His Asn Thr Gln
145                 150                 155                 160

Arg Pro Arg Gly Phe Gly Phe Ile Thr Phe Asp Ser Glu Glu Ser Val
                165                 170                 175

Asp Met Val Leu His Lys Thr Phe His Glu Leu Asn Gly Lys Met Val
            180                 185                 190

Glu Val Lys Arg Ala Val Pro Lys Glu Leu Ser Ser Thr Thr Pro Asn
        195                 200                 205

Arg Ser Pro Leu Ile Gly Tyr Gly Asn Asn Tyr Gly Val Val Pro Asn
    210                 215                 220

Arg Ser Ala Asn Ser Tyr Phe Asn Ser Phe Pro Pro Gly Tyr Asn
225                 230                 235                 240

Asn Asn Asn Leu Gly Ser Ala Gly Arg Phe Ser Pro Ile Gly Ser Gly
                245                 250                 255

Arg Asn Ala Phe Ser Ser Phe Gly Leu Gly Leu Asn Gln Glu Leu Asn
            260                 265                 270

Leu Asn Ser Asn Phe Asp Gly Asn Thr Leu Gly Tyr Ser Arg Ile Pro
        275                 280                 285

Gly Asn Gln Tyr Phe Asn Ser Ala Ser Pro Asn Arg Tyr Asn Ser Pro
    290                 295                 300

Ile Gly Tyr Asn Arg Gly Asp Ser Ala Tyr Asn Pro Ser Asn Arg Asp
305                 310                 315                 320

Leu Trp Gly Asn Arg Ser Asp Ser Ser Gly Pro Gly Trp Asn Leu Gly
                325                 330                 335

Val Ser Val Gly Asn Asn Arg Gly Asn Trp Gly Leu Ser Ser Val Val
            340                 345                 350

Ser Asp Asn Asn Gly Tyr Gly Arg Ser Tyr Gly Ala Gly Ser Gly Leu
        355                 360                 365

Ser Gly Leu Ser Phe Ala Gly Asn Thr Asn Gly Phe Asp Gly Ser Ile
    370                 375                 380

Gly Glu Leu Tyr Arg Gly Ser Ser Val Tyr Ser Asp Ser Thr Trp Gln
385                 390                 395                 400

Gln Ser Met Pro His His Gln Ser Ser Asn Glu Leu Asp Gly Leu Ser
                405                 410                 415

Arg Ser Tyr Gly Phe Gly Ile Asp Asn Val Gly Ser Asp Pro Ser Ala
            420                 425                 430

Asn Ala Ser Glu Gly Tyr Ser Gly Asn Tyr Asn Val Gly Asn Arg Gln
        435                 440                 445

Thr His Arg Gly Ile Glu Ala
    450                 455

<210> SEQ ID NO 18

<211> LENGTH: 2524
<212> TYPE: DNA
<213> ORGANISM: Arabidopsis thaliana

<400> SEQUENCE: 18

| | | | | | |
|---|---|---|---|---|---|
| atatgtgaga | ctaactattg | ttctctgtct | ctttttttct | ttttaattat | caaagaaaga | 60 |
| aactctttct | taatggaaac | catttacaga | taaaaaaaac | attaaaagga | aaggttttta | 120 |
| ataaagcctt | tgagagagaa | gatgttatt | ataggatgaa | caaaaacatc | ctctgtttct | 180 |
| ctcttttcat | atttttctcc | acatttcctc | atctgggtca | tctccaaaaa | tggtgctttt | 240 |
| ttttaataat | tcttcacgtt | tctgggtttt | tggttttgtg | atttgatgat | gcttttttt | 300 |
| tgttttttc | agatttgatg | ataacccaaa | ttcgcaattt | gattaggaca | acaacaacaa | 360 |
| ctttatttat | ctgattccgt | ctttgatttt | cagacaagaa | aagtatgttg | tttctaagtc | 420 |
| ttttgatttt | tttcaatttc | atctccttac | tcgatttttt | tttttttggg | tttctctgaa | 480 |
| ttggagcaga | aaaaaaaaag | atggaatcgg | atctggggaa | gctcttcatt | ggtgggattt | 540 |
| cgtgggatac | agacgaagaa | aggttaagag | actactttag | caactatggt | gatgttgttg | 600 |
| aagctgtgat | catgagagat | cgtgccacag | gtcgtgcacg | tggcttcggc | ttcattgtct | 660 |
| tgcagaccc | ctgtgtctca | gagagagtga | tcatggataa | acacatcatc | gatggccgca | 720 |
| cggtttgtga | tttcaatcat | ttctcaatct | ttcagcagaa | caaacaaagt | tcagatctta | 780 |
| ttgcaacttc | ctcaatttgc | gttttgaat | catctctcaa | tctttgtttc | tcaaagtgta | 840 |
| aagatcaaat | ttatgttttg | caggttgagg | cgaagaaggc | tgtgcctcga | gatgatcagc | 900 |
| aggtgctaaa | gcgacacgct | agtcctatcc | accttatgtc | acctgtccat | ggtggtggtg | 960 |
| gaaggacaaa | gaagatcttc | gttggaggtt | taccgtctag | cattaccgag | gaggagttca | 1020 |
| agaactactt | tgatcagttt | ggtactattg | ctgatgttgt | tgtaatgtat | gatcataaca | 1080 |
| cgcagaggcc | aagaggtttt | ggcttcatca | catttgattc | agatgatgct | gttgatagag | 1140 |
| ttcttcacaa | gaccttccat | gagctcaatg | ggaaactagt | tgaggtcaaa | agagctgtac | 1200 |
| ctaaggagat | ttcccctgtt | tctaatatcc | gaagcccgct | tgctagcggt | gttaactatg | 1260 |
| gaggcgggtc | taataggatg | cctgctaata | gctactttaa | caactttgct | cctggtcctg | 1320 |
| gtttttataa | cagtctaggt | cctgttggtc | gtcggtttag | tcctgttatt | ggtagtggta | 1380 |
| gaaatgcggt | ttctgctttt | ggcctcggtt | tgaatcatga | cttgagtttg | aatttgaatc | 1440 |
| caagctgcga | tgggacaagt | tctacgtttg | gttataaccg | tattccaagc | aacccttact | 1500 |
| tcaacggtgc | ttccccgaac | cgttacacct | ctccaatcgg | gcacaataga | actgagtctc | 1560 |
| cttacaattc | gaacaataga | gacttatggg | gaaacagaac | cgacactgca | ggtcccggtt | 1620 |
| ggaacttgaa | tgtctcgaat | ggaaacaaca | gaggaaattg | gggacttcct | tcttcttctg | 1680 |
| ctgttagtaa | tgataacaat | ggctttggaa | ggaactatgg | gacaagttct | ggactttcct | 1740 |
| cgtccccatt | taatggtttt | gaaggttcta | taggggaact | gtacagaggc | ggctcagtct | 1800 |
| acagcgactc | aacgtggcag | caacagcagc | taccatctca | gtcttctcac | gagctagaca | 1860 |
| atttgtctcg | cgcttacggt | tatgatattg | acaatgtagg | ttcagaccca | tctgcaaatg | 1920 |
| acccagaaac | ttacaatgga | agctacaatg | ttggaaatag | acaaactaat | agaggtaaca | 1980 |
| aaaaaattca | tctcaataaa | acttgtaact | tggatacatt | ttgatcgcaa | tcgaaatgtt | 2040 |
| ctgatctgtg | ttttatttac | ttgttgaggt | attgctgcat | aggttatcaa | aaaccaagaa | 2100 |
| aacaaaaaaa | aaagttgaga | gatttgtaga | ttgaaagcaa | ccaaatttca | gttgcagagt | 2160 |
| ttgaacaggt | tctcatgaca | aagaaaccaa | ctttgttgat | cacagtgcca | aagattatgg | 2220 |

```
tttgctttct cttttgttag accaaaaaaa aaaaaaaaaa agagaaaaac aaagaaccgt    2280
ttttgttttt cttcttctta cataaagatc agatcgtagc agccagacaa ccaaagatac    2340
tacaaggtgg atttagattt gcttctcaaa aaagttttt ttttctttc atagaataac     2400 caaacaaaga tcgtagaatt ttcgatcaaa gattcttcag agttctgtgc tctgttttgt    2460
aattgtactt ttttttttctt gtttacaaaa tgaattgttc atgaaaactt tgttttctta    2520
aaaa                                                                  2524
```

<210> SEQ ID NO 19
<211> LENGTH: 460
<212> TYPE: PRT
<213> ORGANISM: Arabidopsis thaliana

<400> SEQUENCE: 19

```
Met Glu Ser Asp Leu Gly Lys Leu Phe Ile Gly Gly Ile Ser Trp Asp
1               5                   10                  15

Thr Asp Glu Glu Arg Leu Arg Asp Tyr Phe Ser Asn Tyr Gly Asp Val
            20                  25                  30

Val Glu Ala Val Ile Met Arg Asp Arg Ala Thr Gly Arg Ala Arg Gly
        35                  40                  45

Phe Gly Phe Ile Val Phe Ala Asp Pro Cys Val Ser Glu Arg Val Ile
    50                  55                  60

Met Asp Lys His Ile Ile Asp Gly Arg Thr Val Glu Ala Lys Lys Ala
65                  70                  75                  80

Val Pro Arg Asp Asp Gln Gln Val Leu Lys Arg His Ala Ser Pro Ile
                85                  90                  95

His Leu Met Ser Pro Val His Gly Gly Gly Gly Arg Thr Lys Lys Ile
            100                 105                 110

Phe Val Gly Gly Leu Pro Ser Ser Ile Thr Glu Glu Phe Lys Asn
        115                 120                 125

Tyr Phe Asp Gln Phe Gly Thr Ile Ala Asp Val Val Met Tyr Asp
    130                 135                 140

His Asn Thr Gln Arg Pro Arg Gly Phe Gly Phe Ile Thr Phe Asp Ser
145                 150                 155                 160

Asp Asp Ala Val Asp Arg Val Leu His Lys Thr Phe His Glu Leu Asn
                165                 170                 175

Gly Lys Leu Val Glu Val Lys Arg Ala Val Pro Lys Glu Ile Ser Pro
            180                 185                 190

Val Ser Asn Ile Arg Ser Pro Leu Ala Ser Gly Val Asn Tyr Gly Gly
        195                 200                 205

Gly Ser Asn Arg Met Pro Ala Asn Ser Tyr Phe Asn Asn Phe Ala Pro
    210                 215                 220

Gly Pro Gly Phe Tyr Asn Ser Leu Gly Pro Val Gly Arg Arg Phe Ser
225                 230                 235                 240

Pro Val Ile Gly Ser Gly Arg Asn Ala Val Ser Ala Phe Gly Leu Gly
                245                 250                 255

Leu Asn His Asp Leu Ser Leu Asn Leu Asn Pro Ser Cys Asp Gly Thr
            260                 265                 270

Ser Ser Thr Phe Gly Tyr Asn Arg Ile Pro Ser Asn Pro Tyr Phe Asn
        275                 280                 285

Gly Ala Ser Pro Asn Arg Tyr Thr Ser Pro Ile Gly His Asn Arg Thr
    290                 295                 300

Glu Ser Pro Tyr Asn Ser Asn Asn Arg Asp Leu Trp Gly Asn Arg Thr
305                 310                 315                 320
```

```
Asp Thr Ala Gly Pro Gly Trp Asn Leu Asn Val Ser Asn Gly Asn Asn
            325                 330                 335

Arg Gly Asn Trp Gly Leu Pro Ser Ser Ser Ala Val Ser Asn Asp Asn
            340                 345                 350

Asn Gly Phe Gly Arg Asn Tyr Gly Thr Ser Ser Gly Leu Ser Ser
            355                 360                 365

Pro Phe Asn Gly Phe Glu Gly Ser Ile Gly Glu Leu Tyr Arg Gly Gly
            370                 375                 380

Ser Val Tyr Ser Asp Ser Thr Trp Gln Gln Gln Leu Pro Ser Gln
385                 390                 395                 400

Ser Ser His Glu Leu Asp Asn Leu Ser Arg Ala Tyr Gly Tyr Asp Ile
            405                 410                 415

Asp Asn Val Gly Ser Asp Pro Ser Ala Asn Asp Pro Glu Thr Tyr Asn
            420                 425                 430

Gly Ser Tyr Asn Val Gly Asn Arg Gln Thr Asn Arg Gly Asn Lys Lys
            435                 440                 445

Ile His Leu Asn Lys Thr Cys Asn Leu Asp Thr Phe
            450                 455                 460

<210> SEQ ID NO 20
<211> LENGTH: 2607
<212> TYPE: DNA
<213> ORGANISM: Arabidopsis thaliana

<400> SEQUENCE: 20
ctgtaatgtg gagtttggaa ttttcgacaa caaagtgcac atctggcaca gagattgtca      60
cagcacgaaa gattttttg tcgttcttgt aggatttgct ggcacgtgtg aatagaaaa     120 cacacgagtg aaaccatcgt cggtctttgt agcccattat ttatacttct attgggctgg    180
acttaagccc ataagtaagc atctctgtta caagaaaacg ggaaacagat ctgaaccgtt    240
aataatatta gaaggatct agaccgttga tttatttatc tgctgacaga ttcgtacctt     300
cgcgaatatc aataccaaac caatagaaat attcgttcgc tgtcttcttc ctcttcctcc    360
tctcaaatcg gctacagcca ttggaaaagc taaagccttt tcgtaatttc tggaagtttc    420
tgcagtcggt tttcacggtt tcgtagattg aggtggattt gtgattctgg gtcagaagta    480
agatagtgga atataaattc atggattcgg atcaaggaaa gcttttttgtc ggtggtattt    540 catgggaaac tgatgaagat aagctgagag aacatttcac caactatgga gaggtttctc    600
aggctattgt gatgagagac aagctcacag gtcgacctag gggttttggg ttcgttatct    660
tctcggatcc ttctgttctc gatagggttc ttcaagagaa acacagcatt gataccagag    720
aggttattat tgttctctta agctccatt tctctaattg tgttaaagtt ttatcctttt      780
tgcgttttgc tgtgttgatt gagaacgaga gtaaatatag aattttgttt ggttggcaaa    840
ttcgccttag tgtttcttag attctaggat tggttttaac ttgtataaga ggtattatag    900
ggtactcgat atatgttaat cgtacactct atgaagtgat tgagtatagt attagaaaag    960
agagcttggt ttggtttatt aggataagga aaaacagatg tatatatttt ctgttgcgtt   1020
atgttctcga tttgggtaaa gtatgattct tggaagttta ttatgagctt tattgatttt    1080
ggttaatgtt taggttgatg tgaagagagc catgtcaaga gaggagcagc aagtctctgg    1140
aagaactggg aatcttaata catctagaag ttctggaggt gatgcttaca ataaaaccaa    1200
gaagatcttt gttggaggct tgccacctac tttgactgat gaagagtttc gccagtactt    1260
tgaagtttat ggccctgtga ctgatgttgc aatcatgtat gaccaggcta ccaaccgtcc    1320
tcgtgggttt ggatttgttt ccttcgactc tgaagatgcg gtagacagtg ttttgcacaa   1380
```

-continued

```
gactttccat gatttgagcg gtaaacaagt tgaagtaaag cgtgctcttc ctaaagatgc    1440
caatcctgga ggtggtggac gatcaatggg tggtggtggc tctggtggtt accagggtta    1500
tggtggcaat gaaagcagtt atgatggacg tatggattcc aataggtttt tgcagcatca    1560
aagtgttgga aatggtttac catcttatgg ttcttctggt tatggcgctg gctatggaaa    1620
tggtagtaat ggtgccgggt atggtgccta tggaggttac actggttctg ctggaggtta    1680
tggcgctggt gctactgctg gatatggagc aacgaacatt ccaggtgctg gctatggaag    1740
tagtactgga gttgctccga gaaactcatg ggacactcca gcttctagtg gttatgggaa    1800
cccaggctat gggagtggtg ctgctcatag tggatatgga gttcctggtg cagctcctcc    1860
tacgcagtca ccatctggct atagtaacca aggctacggt tatggagggt acagtggaag    1920
tgattctggt tatggaaatc aagctgcata tggtgtggtt ggagggcgtc ctagtggtgg    1980
cggttcaaac aaccctggta gtggtggcta catgggaggt ggttatggtg atggatcttg    2040
gcgatctgac ccgtcacaag gttatggtgg tgggtacaat gatggtcagg gtcgacaagg    2100
ccagtagtga ctgtgtaagg ggattatgac cgccctggtt tctggatcct tgtcaagaag    2160
aatttagctc aaatcaaagg ttccacaact tcctaacggg ttggactgct tgaatctctt    2220
tataagcatg tgctatctat tacaataagt cacttctatt aagttatttt tcggttgagt    2280
gtacttttga gttttggcag agttattata actacaggct ttgctgtttt cgtattatgt    2340
ttgtcttcct agtattcttg ccggattgtt tgttttgatt gtgttatttt gttttggccc    2400
tgatggatat aacttaagca gggaataatg cttcagggta cttgttaaga aagcagatgg    2460
tgagagcaga actcgatgga ggtgagagtc aaattgctga atgtatggtt tgagtagaaa    2520
gtagaggtag ttggtaacgt tagtggtacc attaagaaga aggtgtagaa aatagtgaga    2580
ggtagctttg agaaaaaggc ataatca                                       2607
```

<210> SEQ ID NO 21
<211> LENGTH: 406
<212> TYPE: PRT
<213> ORGANISM: Arabidopsis thaliana

<400> SEQUENCE: 21

```
Met Asp Ser Asp Gln Gly Lys Leu Phe Val Gly Gly Ile Ser Trp Glu
1               5                   10                  15

Thr Asp Glu Asp Lys Leu Arg Glu His Phe Thr Asn Tyr Gly Glu Val
            20                  25                  30

Ser Gln Ala Ile Val Met Arg Asp Lys Leu Thr Gly Arg Pro Arg Gly
        35                  40                  45

Phe Gly Ile Arg Lys Asn Arg Cys Ile Tyr Phe Leu Leu Arg Tyr Val
    50                  55                  60

Leu Asp Leu Gly Lys Val Asp Val Lys Arg Ala Met Ser Arg Glu Glu
65                  70                  75                  80

Gln Gln Val Ser Gly Arg Thr Gly Asn Leu Asn Thr Ser Arg Ser Ser
                85                  90                  95

Gly Gly Asp Ala Tyr Asn Lys Thr Lys Lys Ile Phe Val Gly Gly Leu
            100                 105                 110

Pro Pro Thr Leu Thr Asp Glu Glu Phe Arg Gln Tyr Phe Glu Val Tyr
        115                 120                 125

Gly Pro Val Thr Asp Val Ala Ile Met Tyr Asp Gln Ala Thr Asn Arg
    130                 135                 140

Pro Arg Gly Phe Gly Phe Val Ser Phe Asp Ser Glu Asp Ala Val Asp
145                 150                 155                 160
```

```
Ser Val Leu His Lys Thr Phe His Asp Leu Ser Gly Lys Gln Val Glu
                165                 170                 175

Val Lys Arg Ala Leu Pro Lys Asp Ala Asn Pro Gly Gly Gly Gly Arg
            180                 185                 190

Ser Met Gly Gly Gly Ser Gly Gly Tyr Gln Gly Tyr Gly Gly Asn
        195                 200                 205

Glu Ser Ser Tyr Asp Gly Arg Met Asp Ser Asn Arg Phe Leu Gln His
    210                 215                 220

Gln Ser Val Gly Asn Gly Leu Pro Ser Tyr Gly Ser Gly Tyr Gly
225                 230                 235                 240

Ala Gly Tyr Gly Asn Gly Ser Asn Gly Ala Gly Tyr Gly Ala Tyr Gly
                245                 250                 255

Gly Tyr Thr Gly Ser Ala Gly Gly Tyr Gly Ala Gly Ala Thr Ala Gly
            260                 265                 270

Tyr Gly Ala Thr Asn Ile Pro Gly Ala Gly Tyr Gly Ser Ser Thr Gly
            275                 280                 285

Val Ala Pro Arg Asn Ser Trp Asp Thr Pro Ala Ser Ser Gly Tyr Gly
    290                 295                 300

Asn Pro Gly Tyr Gly Ser Gly Ala Ala His Ser Gly Tyr Gly Val Pro
305                 310                 315                 320

Gly Ala Ala Pro Pro Thr Gln Ser Pro Ser Gly Tyr Ser Asn Gln Gly
                325                 330                 335

Tyr Gly Tyr Gly Gly Tyr Ser Gly Ser Asp Ser Gly Tyr Gly Asn Gln
            340                 345                 350

Ala Ala Tyr Gly Val Val Gly Gly Arg Pro Ser Gly Gly Gly Ser Asn
            355                 360                 365

Asn Pro Gly Ser Gly Gly Tyr Met Gly Gly Tyr Gly Asp Gly Ser
        370                 375                 380

Trp Arg Ser Asp Pro Ser Gln Gly Tyr Gly Gly Tyr Asn Asp Gly
385                 390                 395                 400

Gln Gly Arg Gln Gly Gln
                405

<210> SEQ ID NO 22
<211> LENGTH: 3178
<212> TYPE: DNA
<213> ORGANISM: Arabidopsis thaliana

<400> SEQUENCE: 22
ttgaaattgg gttaaatcgg tttgaatcgg attgaacaaa aactgtatta ataataattc      60
ttcctctact tttctctctg attgattcca atcttctttc attttcttct tcttcttctt     120
ctggggaagg ggcaggttaa aattatgcca tctattcaaa tcgtgcctat cctcagatct     180
taactctttt ctctacgaga ttcggcatct gggttttatt cttcttggtg gttttttttt     240
tattcttctt cttctgatct cagatttccc ctgattggtt ttttttttg ctaaatccgt      300 tttatgtttt cccgatcaaa ctctcctggc agattctcgg atctgttgtt ttctagattc     360
aatctgaatt tgatttacg ttttgtctt tgtaaagatg tttcctttg atcagatttt        420 gataatccat tgacatctct gattcaagca aaagctaatt aactttgatc cgattccttt     480
gtgtgtgtgt gcagagcaaa atgcaatcgg ataatgaaa gcttttcatc ggtgggatat      540
cttgggacac caatgaggaa cgtctcaagg agtatttcag cagttttgga gaagtgatcg     600
aagctgtcat cttgaaagat cgtaccactg gtcgtgctcg tggtttcggt ttgttgtttt    660
ttgctgatcc tgctgttgct gagattgtta tcaccgaaaa acataatatt gatggcagat    720
```

```
tggtatgttc actgttctct gcctttcgtt tttgtacaat gtaacttgtt ttcgaagctt      780
ccttatgcaa tcaagccttc aagagttaca gtttgttctc atttggttcc gattaatcat      840
ttttgtgctt tgattggatt tttgagaaga aatgagtgat ctttagttat atgagcttag      900
tttttcattt ttcaagttgt tgatcttcc gcaggttgaa gccaagaaag ctgttcccag       960
agatgaccaa acatggtaa atagaagcaa cagcagtagc atccaaggtt ctcccgtgg       1020
tccaggtcgc acaaggaaga tatttgttgg aggattacct tcttcggtta cagagagtga    1080
tttcaagacg tattttgagc agtttggtac aactacggat gtggttgtca tgtatgatca    1140
caacacacaa aggcctagag gtttcgggtt tataacctac gattccgagg aggcggttga    1200
aaggtattg ctcaagacat tccatgaact aaatggtaaa atggttgagg ttaagcgagc     1260
tgttccaaag gagttatctc caggtccaag tcgcagtcct cttggtgcag gttacagcta    1320
tggagttaat agggtcaata acctccttaa tgggtatgct caagggttta atcccgctgc    1380
agttggaggc tacggactta ggatggatgg tcggttcagt ccggttggtg ctggaagaag    1440
cgggtttgca aattacagtt ctggatacgg gatgaatgtg aactttgatc agggattgcc    1500
cacagggttc acgggaggta caaattacaa tggaaatgtt gactatgcc gaggaatgag     1560
cccgtactac attggtaaca caaacaggtt tggtcctgcg gttggctatg aaggggggcaa   1620
cggaggagga aactcatcct tcttcagttc ggttacacgg aacttatggg gaaacaatgg    1680
tggtcttaac tataacaaca ataatacaaa ctcaaactcc aatacatata tgggaggatc    1740
atcaagtggg aacaacacac ttagtggtcc atttggaaat tcaggagtca attggggtgc    1800
tcctggagga ggaaacaatg ctgtgagtaa cgagaatgtg aagtttggtt atggaggaaa    1860
cggtgaatct ggttttgggt tgggaacagg tggttatgca gcaagaaacc caggggctaa    1920
caaggcagca ccatcctctt cattctcttc tgcctcagca accaacaaca cgggttatga    1980
tacagcagga cttgcagagt tttacgggaa tggtgcagtt tatagtgacc ctacatggag    2040
atcaccaact cctgagacag aagggcctgc tccttttagc tatgggattg gaggagggt    2100
tccttcttca gatgtttcag ctagaagttc atctccaggt tatgttggca gttacagtgt    2160
gaacaagaga caaccaaaca gaggtaattg agttcagagt aattttctgc tttaacatgt    2220
gattctatga aaagcaaagg actcttgaga aaagaatttt agaaagccta gatagtttcc    2280
aaatttttga ttatcctcgt cttctttctg gaatatacaa accatggttt agggtcttgc    2340
actaatggtg atctagaaca ccttcgtatc actagtgaat tggcttttcc tcagaaacac    2400
gaatatactt gcatgcagaa acagtagcca ttctgcatct ttattgtttt ttagttcatc    2460
agagattatt tagaggaaag tttctttccg tgctttagat ataagctcat ggaactagaa    2520
aactagttga atctttttatg ttgctcacac cagtgtctat gggaagtcta agaaacttgt    2580
gatgaagaaa ctcaattgca tgactggttt cttatcgctc ttctcttctc tgaattatat    2640
ttcccttttt cggttttgtt gcaggaattg ctacttagta caatcgtttt tgttttacca    2700
cgatattgta ggcgagccat cacggtgaac gatctgtgtc ttttggcgaa tcttttagat    2760
tatcttcttt tcccttcata caaagccagt gaggacgaaa cttgatcata tcatcaccta    2820
gagctaacca gagaatcccg cagacttttc tgtcatggtt tggttttcta aattcattgt    2880
tcctcctagg cttttttctg ctttcttttt ttttctattt ttgttttctt ttcttctttc    2940
aatgagggac agaagaaact gtatcagtct ccggcgaggc ggtaatacat aaggagagtt    3000
caaaacaaaa acccaaaaaa aaaaaaaaa agatgatcct tcttcctcag ttttcttctt    3060
cattgtcatg taatggttct tcttcttttc ttcttcttgg gggttatggt taaggtttgt    3120
```
gttttgaggc agattgtact agagttttt ttcatgtttc ttttgtttg tcgttttt    3178

<210> SEQ ID NO 23
<211> LENGTH: 494
<212> TYPE: PRT
<213> ORGANISM: Arabidopsis thaliana

<400> SEQUENCE: 23

Met Gln Ser Asp Asn Gly Lys Leu Phe Ile Gly Gly Ile Ser Trp Asp
1               5                   10                  15

Thr Asn Glu Glu Arg Leu Lys Glu Tyr Phe Ser Ser Phe Gly Glu Val
            20                  25                  30

Ile Glu Ala Val Ile Leu Lys Asp Arg Thr Thr Gly Arg Ala Arg Gly
        35                  40                  45

Phe Gly Phe Val Val Phe Ala Asp Pro Ala Val Ala Glu Ile Val Ile
    50                  55                  60

Thr Glu Lys His Asn Ile Asp Gly Arg Leu Val Glu Ala Lys Lys Ala
65                  70                  75                  80

Val Pro Arg Asp Asp Gln Asn Met Val Asn Arg Ser Asn Ser Ser Ser
                85                  90                  95

Ile Gln Gly Ser Pro Gly Gly Pro Gly Arg Thr Arg Lys Ile Phe Val
            100                 105                 110

Gly Gly Leu Pro Ser Ser Val Thr Glu Ser Asp Phe Lys Thr Tyr Phe
        115                 120                 125

Glu Gln Phe Gly Thr Thr Thr Asp Val Val Met Tyr Asp His Asn
    130                 135                 140

Thr Gln Arg Pro Arg Gly Phe Gly Phe Ile Thr Tyr Asp Ser Glu Glu
145                 150                 155                 160

Ala Val Glu Lys Val Leu Leu Lys Thr Phe His Glu Leu Asn Gly Lys
                165                 170                 175

Met Val Glu Val Lys Arg Ala Val Pro Lys Glu Leu Ser Pro Gly Pro
            180                 185                 190

Ser Arg Ser Pro Leu Gly Ala Gly Tyr Ser Tyr Gly Val Asn Arg Val
        195                 200                 205

Asn Asn Leu Leu Asn Gly Tyr Ala Gln Gly Phe Asn Pro Ala Ala Val
    210                 215                 220

Gly Gly Tyr Gly Leu Arg Met Asp Gly Arg Phe Ser Pro Val Gly Ala
225                 230                 235                 240

Gly Arg Ser Gly Phe Ala Asn Tyr Ser Ser Gly Tyr Gly Met Asn Val
                245                 250                 255

Asn Phe Asp Gln Gly Leu Pro Thr Gly Phe Thr Gly Thr Asn Tyr
            260                 265                 270

Asn Gly Asn Val Asp Tyr Gly Arg Gly Met Ser Pro Tyr Tyr Ile Gly
        275                 280                 285

Asn Thr Asn Arg Phe Gly Pro Ala Val Gly Tyr Glu Gly Gly Asn Gly
    290                 295                 300

Gly Gly Asn Ser Ser Phe Phe Ser Ser Val Thr Arg Asn Leu Trp Gly
305                 310                 315                 320

Asn Asn Gly Gly Leu Asn Tyr Asn Asn Asn Thr Asn Ser Asn Ser
                325                 330                 335

Asn Thr Tyr Met Gly Gly Ser Ser Gly Asn Asn Thr Leu Ser Gly
            340                 345                 350

Pro Phe Gly Asn Ser Gly Val Asn Trp Gly Ala Pro Gly Gly Asn
        355                 360                 365

| | | | | | | | | | | | |
|---|---|---|---|---|---|---|---|---|---|---|---|
| Asn | Ala | Val | Ser | Asn | Glu | Val | Lys | Phe | Gly | Tyr | Gly | Gly | Asn | Gly |
| | | | 370 | | | | 375 | | | | 380 | | | |

Asn Ala Val Ser Asn Glu Val Lys Phe Gly Tyr Gly Gly Asn Gly
            370             375             380

Glu Ser Gly Phe Gly Leu Gly Thr Gly Gly Tyr Ala Ala Arg Asn Pro
385             390             395             400

Gly Ala Asn Lys Ala Ala Pro Ser Ser Ser Phe Ser Ser Ala Ser Ala
            405             410             415

Thr Asn Asn Thr Gly Tyr Asp Thr Ala Gly Leu Ala Glu Phe Tyr Gly
            420             425             430

Asn Gly Ala Val Tyr Ser Asp Pro Thr Trp Arg Ser Pro Thr Pro Glu
            435             440             445

Thr Glu Gly Pro Ala Pro Phe Ser Tyr Gly Ile Gly Gly Val Pro
450             455             460

Ser Ser Asp Val Ser Ala Arg Ser Ser Ser Pro Gly Tyr Val Gly Ser
465             470             475             480

Tyr Ser Val Asn Lys Arg Gln Pro Asn Arg Gly Ile Ala Thr
            485             490

<210> SEQ ID NO 24
<211> LENGTH: 2351
<212> TYPE: DNA
<213> ORGANISM: Arabidopsis thaliana

<400> SEQUENCE: 24

```
atgatctaac attttttctc aaataataag gtcattgatc cttatataac atggaatcac    60
tataacattt ataacctaca ttcttgctca tatatctctc tccttttttt tccaacatat   120
taacgactaa taataaaatt tatcaaccat tttaaatctc taaatggaac ttattattac   180
atgactaaaa aataaaaata aataaataaa taaacgaagc tgatatgaa aagtcttctc    240
tttcttttt ttttttggt aagtcgatct ctctttcact cactttaacc caattggccg     300
ctatttccca aagtctgttt attttttaa tctctctctc ttctctctca cccaatttca    360
caaacccgaa accctaattt tctcgggaca ctgaaatttt tacagcttct ttcctcttct   420
tcaccgggga gatttgtcgg tactaaatct agggttttg ggtatcaccg gagggttgaa     480
gagagagaaa aaaactcaca atggaatcag atcaggaaa gctatttatc ggcgggattt    540
catgggatac cgacgagaat cttctgagag agtacttcag caatttcggc gaggttttgc   600
aggtcactgt tatgcgagag aaagctactg gtcgtcctag aggattcgga ttcgtcgcat   660
tctcggatcc tgctgttatt gatagggttc ttcaggacaa gcaccatatt gataatagag   720
atgtaagcaa aaatcttgtt tctcaaatgg gtctttctaa atttttgaatc tttatagtaa   780
aaattgatac tttgaatctt gttgttgtcg aggtttgatt ttcatctttg atggatttaa   840
gttgtgttaa tttcttaggt tgatgtgaag agagcaatgt ctagagagga gcagagtcct    900
gctgggagat cagggacttt taatgcttct aggaattttg atagtggagc taacgtgagg   960
actaagaaga tattcgtggg aggtttgcct cctgcattaa catcagatga atttcgggct  1020
tactttgaga cttatggtcc tgtgagtgat gcagtcatta tgattgatca gactacacag  1080
cgtcctcgag gatttgggtt tgtttctttt gattctgaag attcggttga ccttgtttta  1140
cataagactt tccacgattt gaatggtaaa caagtcgaag ttaaagagc tcttcctaaa   1200
gatgctaacc ctggaatagc cagtggtggt ggtcgtggca gtggtggagc tggagggttt  1260
ccgggctatg gtggttctgg tggaagtggc tatgagggtc gtgtggattc taatagatac  1320
atgcagccgc aaaacactgg aagtggttat cctccttatg gtggttctgg gtatggtact  1380
ggttatggtt atggaagcaa tggtgtaggt tatgggggtt ttggtgggta tggcaatcca  1440
```

-continued

```
gctggtgcgc cttatgggaa tcctagtgtc cctggagctg ggtttggaag tggtccaaga    1500
agttcatggg gcgctcaagc accatcgggt tatgggaatg tgggatatgg aaatgcagct    1560
ccgtggggtg gttctggtgg tcctggttca gcagtaatgg gtcaagctgg tgcatctgca    1620
ggttatggca gtcaaggtta tggctatggt ggaaatgatt cctcttacgg gactccatct    1680
gcctatggtg cagtaggggg gcgatctggg aatatgccta caaccatgg tggcggtggc    1740 tatgcggatg ctttagatgg ctctggaggc tatgggaatc accaagggaa caacgggcaa    1800
gctggttatg gtggaggtta tggaagtggt aggcaagctc aacaacagtg attgaagaag    1860
aaatactact agaatgtggt tttatcgctg accttgaaac ctcctgcttt ccgccttaac    1920
catgtcacgt ctttggcggt tagaccagga ggtggaccta cgctggatta tctcttttgt    1980
tagtttctca ataagttgtt ttcaggcaat tccggatact atttcctatc aagttgtagt    2040 tttaagttt gcgtgcttat ttatatttgt cgctttggaa tggttttctt tctctgttat    2100
cctctagtgt ttgtgtttaa cgatacatcc tccagattat cattattcat ctccctttg    2160 gttcattcat ttttgttgaa tattccattc acagattctt gcttttgcat ctcctctgtt    2220
taggggaaga tgatttgctc agtgttcaat gtgatctaag aaaagtgttt ggtagagcaa    2280
gagctgcaat aaatcacttt gagattgcgt tgttacatga aggtcgtgtt ggcggaaact    2340
taacagtccc a                                                          2351
```

<210> SEQ ID NO 25
<211> LENGTH: 404
<212> TYPE: PRT
<213> ORGANISM: Arabidopsis thaliana

<400> SEQUENCE: 25

```
Met Glu Ser Asp Gln Gly Lys Leu Phe Ile Gly Gly Ile Ser Trp Asp
1               5                   10                  15

Thr Asp Glu Asn Leu Leu Arg Glu Tyr Phe Ser Asn Phe Gly Glu Val
            20                  25                  30

Leu Gln Val Thr Val Met Arg Glu Lys Ala Thr Gly Arg Pro Arg Gly
        35                  40                  45

Phe Gly Phe Val Ala Phe Ser Asp Pro Ala Val Ile Asp Arg Val Leu
    50                  55                  60

Gln Asp Lys His His Ile Asp Asn Arg Asp Val Asp Val Lys Arg Ala
65                  70                  75                  80

Met Ser Arg Glu Glu Gln Ser Pro Ala Gly Arg Ser Gly Thr Phe Asn
                85                  90                  95

Ala Ser Arg Asn Phe Asp Ser Gly Ala Asn Val Arg Thr Lys Lys Ile
            100                 105                 110

Phe Val Gly Gly Leu Pro Pro Ala Leu Thr Ser Asp Glu Phe Arg Ala
        115                 120                 125

Tyr Phe Glu Thr Tyr Gly Pro Val Ser Asp Ala Val Ile Met Ile Asp
    130                 135                 140

Gln Thr Thr Gln Arg Pro Arg Gly Phe Gly Phe Val Ser Phe Asp Ser
145                 150                 155                 160

Glu Asp Ser Val Asp Leu Val Leu His Lys Thr Phe His Asp Leu Asn
                165                 170                 175

Gly Lys Gln Val Glu Val Lys Arg Ala Leu Pro Lys Asp Ala Asn Pro
            180                 185                 190

Gly Ile Ala Ser Gly Gly Gly Arg Gly Ser Gly Gly Ala Gly Phe
        195                 200                 205

Pro Gly Tyr Gly Gly Ser Gly Gly Ser Gly Tyr Glu Gly Arg Val Asp
```

```
                    210                 215                 220
Ser Asn Arg Tyr Met Gln Pro Gln Asn Thr Gly Ser Gly Tyr Pro Pro
225                 230                 235                 240

Tyr Gly Gly Ser Gly Tyr Gly Thr Gly Tyr Gly Tyr Gly Ser Asn Gly
                245                 250                 255

Val Gly Tyr Gly Gly Phe Gly Gly Tyr Gly Asn Pro Ala Gly Ala Pro
                260                 265                 270

Tyr Gly Asn Pro Ser Val Pro Gly Ala Gly Phe Gly Ser Gly Pro Arg
            275                 280                 285

Ser Ser Trp Gly Ala Gln Ala Pro Ser Gly Tyr Gly Asn Val Gly Tyr
290                 295                 300

Gly Asn Ala Ala Pro Trp Gly Gly Ser Gly Gly Pro Gly Ser Ala Val
305                 310                 315                 320

Met Gly Gln Ala Gly Ala Ser Ala Gly Tyr Gly Ser Gln Gly Tyr Gly
                325                 330                 335

Tyr Gly Gly Asn Asp Ser Ser Tyr Gly Thr Pro Ser Ala Tyr Gly Ala
            340                 345                 350

Val Gly Gly Arg Ser Gly Asn Met Pro Asn Asn His Gly Gly Gly Gly
        355                 360                 365

Tyr Ala Asp Ala Leu Asp Gly Ser Gly Tyr Gly Asn His Gln Gly
370                 375                 380

Asn Asn Gly Gln Ala Gly Tyr Gly Gly Gly Tyr Gly Ser Gly Arg Gln
385                 390                 395                 400

Ala Gln Gln Gln

<210> SEQ ID NO 26
<211> LENGTH: 2731
<212> TYPE: DNA
<213> ORGANISM: Arabidopsis thaliana

<400> SEQUENCE: 26
tgagcattgc ttatttgctt ccatccattt ttgttccttt taattcgatt tggattgcag      60
aaaaagaaaa gaaagaaaaa gactaaaaat ttggacgata agcagaaaag agagaggagg     120
gcctctcgcc ctcttattaa aaccttgcct tctccaaatc tgaagatttc tcaatcctaa     180
aatctttttt ttttcctctt tctccgtttc tttattttcg gtattacaca catacataga     240
ttctctgtct tctgggtttt tcattccttc cttcctccaa gcttacacct ttattgatca     300
tttgtgtttt tttttgtttc tgcaggaatc caagatcgtg ggtcgatcgg tttttacaca     360
atccgatcac gacccatctg ctcttttttca tcctattttg cttcccttga ggtgtttcta    420
tcgattccat tctccttctc acttagatcg atatagaatc tggaaccaaa acaaaacctt     480
tttttgtttg tttggcagaa atggaaatgg aatcatgtaa gctcttcatc ggtggtatat     540
cttgggaaac cagtgaagat cgtcttcgtg actattttca cagttttggt gaggttttag     600
aggctgttat tatgaaggat cgtgccactg gccgtgctcg tggctttggt ttcgttgtct     660
ttgctgatcc taatgttgct gaaagagtcg tcttgcttaa acatatcatt gatggtaaaa     720
ttgtaagttt cctcctgcta tataccaaca tacattgctt ccaatttcaa caatcttcct     780
gcttacttgc ttcattttga ggttgctgct tctcaaagca aagcaaagct actcactttt     840
attccttcct gttttagtta gtagactcta ttgtttacaa tcagctttgc cgctctgata     900
aatgcatatc tttgtcagaa gttgttcatt tcacactcac aaataaaaat gtaaaacttg     960
gatcgtttca tatcctcatg tgaaagaaag tggttcacaa tgaatgaaaa actgctttct    1020
ttgagttgtg tcgtgtgttg attttctcca tgatatacag gttgaggcaa agaaggctgt    1080
```

```
tccaagagat gatcacgtag tatttaataa aagtaacagc agccttcagg gatcacctgg    1140
cccatcaaac tccaagaaga tctttgtggg aggtttggca tcatccgtga cagaggctga    1200
gttcaaaaag tattttgctc agtttgggat gatcactgat gttgtggtga tgtatgacca    1260
cagaacccag cggcctagag gctttgggtt catttcatat gactctgagg aagctgttga    1320
caaagtactg cagaagacat tccacgaact caatggtaag atggtggagg tcaaactggc    1380
tgttcctaag gatatggctc tcaacacaat gcggaaccaa atgaatgtaa atagctttgg    1440
cactagtaga atcagttcat tactgaatga gtacacccag ggattcagcc cgagtccaat    1500
ctctggttat ggagtgaaac ctgaagttag gtacagtcca gcagtaggta ataggggagg    1560
attctcaccg tttggacatg gatacggaat cgagctgaat tttgagccaa accagactca    1620
gaactacggt tctggttcca gtggaggctt tggacgaccc tttagccctg gatatgctgc    1680
gagtctcggc aggttcggta gccaaatgga gtcgggagga gctagtgttg gaacggttc     1740 tgtcctaaat gcagcaccaa agaaccattt atggggaaat ggtggtctag gttacatgtc    1800
aaactctccg atatcaagaa gcagcttcag tggaaactct ggaatgtctt cactaggcag    1860
cattggtgac aactggggaa cagttgcacg tgcacgcagt agctaccacg gtgagagagg    1920
aggtgtagga ttagaagcaa tgagaggagt tcatgttggt ggttacagca gcggctcaag    1980
catcttggag gcagactctc tgtacagcga ctcgatgtgg ctttcgctgc ctgcaaaggc    2040
agaggaagga ttgggaatgg gaccattgga cttcatgtct agaggaccag ctggatacat    2100
caacaggcaa ccaaacggag gtatgaataa tgaatgaatg aacgcctttt ttctatccga    2160
gaattcaagc atttgtagaa aatctgatga tatcatatga aaatggtgtt gttgcaggaa    2220
ttgcagctta gagaagtgac aaatctatac catggagatc agatgattgc agaagagagt    2280
ttttagaaga ggaaaaaagt ttattaaaaa aaaaaaaatt attggtacca aaaagcttaa    2340
agcttttatt tacttttac tattttgatt tgttgttata gctttctttt cacccttttt     2400
tctaatttgg ggttttgttt cttttgtttt tatcgttaaa gaaaaagat gtaaacttga     2460 gtgatataaa aagagacaaa gaaacaatga agtgtatttt gttcttgtct ttctctctct    2520
tttatcatct aaatccatat attgacaaat tcaaacatga aaacgaatta aaaaaagagc    2580
aatttgccta gaatgtaggc aacgtagtgt gaggacgacg tgtggcaaac atgtggatga    2640
tgataagcca caggacaaag aaagcaatcc ctcatccatc gcaataatat ccattaatgt    2700
gaagtggacc aaaagagaga gaagcgagtg t                                   2731
```

<210> SEQ ID NO 27
<211> LENGTH: 431
<212> TYPE: PRT
<213> ORGANISM: Arabidopsis thaliana

<400> SEQUENCE: 27

Met Glu Met Glu Ser Cys Lys Leu Phe Ile Gly Gly Ile Ser Trp Glu
1               5                   10                  15

Thr Ser Glu Asp Arg Leu Arg Asp Tyr Phe His Ser Phe Gly Glu Val
            20                  25                  30

Leu Glu Ala Val Ile Met Lys Asp Arg Ala Thr Gly Arg Ala Arg Gly
        35                  40                  45

Phe Gly Phe Val Val Phe Ala Asp Pro Asn Val Ala Glu Arg Val Val
    50                  55                  60

Leu Leu Lys His Ile Ile Asp Gly Lys Ile Val Glu Ala Lys Lys Ala
65                  70                  75                  80

```
Val Pro Arg Asp Asp His Val Val Phe Asn Lys Ser Asn Ser Ser Leu
                85                  90                  95

Gln Gly Ser Pro Gly Pro Ser Asn Ser Lys Lys Ile Phe Val Gly Gly
            100                 105                 110

Leu Ala Ser Ser Val Thr Glu Ala Glu Phe Lys Lys Tyr Phe Ala Gln
            115                 120                 125

Phe Gly Met Ile Thr Asp Val Val Met Tyr Asp His Arg Thr Gln
            130                 135                 140

Arg Pro Arg Gly Phe Gly Phe Ile Ser Tyr Asp Ser Glu Glu Ala Val
145                 150                 155                 160

Asp Lys Val Leu Gln Lys Thr Phe His Glu Leu Asn Gly Lys Met Val
                165                 170                 175

Glu Val Lys Leu Ala Val Pro Lys Asp Met Ala Leu Asn Thr Met Arg
            180                 185                 190

Asn Gln Met Asn Val Asn Ser Phe Gly Thr Ser Arg Ile Ser Ser Leu
            195                 200                 205

Leu Asn Glu Tyr Thr Gln Gly Phe Ser Pro Ser Pro Ile Ser Gly Tyr
210                 215                 220

Gly Val Lys Pro Glu Val Arg Tyr Ser Pro Ala Val Gly Asn Arg Gly
225                 230                 235                 240

Gly Phe Ser Pro Phe Gly His Gly Tyr Gly Ile Glu Leu Asn Phe Glu
                245                 250                 255

Pro Asn Gln Thr Gln Asn Tyr Gly Ser Gly Ser Gly Gly Phe Gly
            260                 265                 270

Arg Pro Phe Ser Pro Gly Tyr Ala Ala Ser Leu Gly Arg Phe Gly Ser
            275                 280                 285

Gln Met Glu Ser Gly Gly Ala Ser Val Gly Asn Gly Ser Val Leu Asn
290                 295                 300

Ala Ala Pro Lys Asn His Leu Trp Gly Asn Gly Leu Gly Tyr Met
305                 310                 315                 320

Ser Asn Ser Pro Ile Ser Arg Ser Ser Phe Ser Gly Asn Ser Gly Met
            325                 330                 335

Ser Ser Leu Gly Ser Ile Gly Asp Asn Trp Gly Thr Val Ala Arg Ala
            340                 345                 350

Arg Ser Ser Tyr His Gly Glu Arg Gly Gly Val Gly Leu Glu Ala Met
            355                 360                 365

Arg Gly Val His Val Gly Gly Tyr Ser Ser Gly Ser Ser Ile Leu Glu
            370                 375                 380

Ala Asp Ser Leu Tyr Ser Asp Ser Met Trp Leu Ser Leu Pro Ala Lys
385                 390                 395                 400

Ala Glu Glu Gly Leu Gly Met Gly Pro Leu Asp Phe Met Ser Arg Gly
                405                 410                 415

Pro Ala Gly Tyr Ile Asn Arg Gln Pro Asn Gly Gly Ile Ala Ala
            420                 425                 430

<210> SEQ ID NO 28
<211> LENGTH: 1395
<212> TYPE: DNA
<213> ORGANISM: Oryza sativa

<400> SEQUENCE: 28
atggagtcgg atcaggggaa gctgttcatc ggcggcatct cgtgggagac caccgaggag      60
aagctccgcg accacttcgc cgcctacggc gacgtctccc aggccgccgt catgcgcgac     120
aagctcaccg ccgcccccg cggcttcggc ttcgtcgtct tctccgaccc ttcctccgtc     180
```

-continued

```
gacgccgccc tcgtcgaccc ccacaccctc gacggccgca cggttgatgt gaagcgggcg    240
ctctcgcggg aggagcagca ggccgcgaag gcggcgaacc ctagcgcggg ggggaggcac    300
gcctccggtg ggggcggtgg tggggaggcc gccggtggtg gtggtggtgg cggcggtggt    360
gacgccggcg gtgcgcggac gaagaagatc ttcgtcggcg ggctgccctc caacctgacg    420
gaggacgagt tccggcagta cttccagacc tacggggtcg tcaccgacgt cgtcgtcatg    480
tacgaccaga acacgcagcg gccgagggg ttcgggttca tcaccttcga cgcggaggac    540
gccgttgacc gcgtgctgca caagaccttc catgacctga gcgggaagat ggtggaggtg    600
aagcgcgccc tgcccaggga ggccaaccct ggctccggca gtggtggccg ttccatggga    660
ggcggcggtg ggggttacca gagtaacaat gggccgaact ccaattctgg gggctatgat    720
agcagaggtg acgctagcag gtatggtcag gcgcagcagg gtagtggtgg ttatcccggt    780
tatggtgctg gaggatatgg tgctggtacg gttggttatg gatatgggca tgctaaccct    840
ggaactgcgt atgggaatta tggggctgga ggatttggag gtgttcctgc tgggtatggt    900
gggcattatg gcaatccaaa tgcgcctggt tcaggttacc agggtggtcc tccaggagca    960
aacagaggac catggggtgg tcaagctccg tctggttatg gcactgggag ttatggtggc   1020
aatgcaggct atgctgcttg gaacaactct tctgctggag gtaatgcacc cactagtcag   1080
gccgctggtg caggcacagg ctatgggagc cagggctatg gatatggtgg atatggagga   1140
gatgcatcgt atggtaatca tggtggatat gggggttatg gaggaagggg agatggtgct   1200
ggcaatccag ctgctggcgg tggatctggg tatggtgctg gctatggaag cgggaatggc   1260
ggttctggtt atccaaatgc ttgggctgat ccttcacaag gtggagggtt tggggcttca   1320
gtcaatggag tgtctgaagg ccaatcaaat tatggcagtg gttatggtgg tgtgcaacct   1380
agggttgctc agtaa                                                    1395
```

<210> SEQ ID NO 29
<211> LENGTH: 464
<212> TYPE: PRT
<213> ORGANISM: Oryza sativa

<400> SEQUENCE: 29

Met Glu Ser Asp Gln Gly Lys Leu Phe Ile Gly Gly Ile Ser Trp Glu
1               5                   10                  15

Thr Thr Glu Glu Lys Leu Arg Asp His Phe Ala Ala Tyr Gly Asp Val
                20                  25                  30

Ser Gln Ala Ala Val Met Arg Asp Lys Leu Thr Gly Arg Pro Arg Gly
            35                  40                  45

Phe Gly Phe Val Val Phe Ser Asp Pro Ser Ser Val Asp Ala Ala Leu
        50                  55                  60

Val Asp Pro His Thr Leu Asp Gly Arg Thr Val Asp Val Lys Arg Ala
65                  70                  75                  80

Leu Ser Arg Glu Glu Gln Gln Ala Ala Lys Ala Ala Asn Pro Ser Ala
                85                  90                  95

Gly Gly Arg His Ala Ser Gly Gly Gly Gly Gly Gly Gly Gly Ala Gly
                100                 105                 110

Gly Gly Gly Gly Gly Gly Gly Asp Ala Gly Gly Ala Arg Thr Lys
            115                 120                 125

Lys Ile Phe Val Gly Gly Leu Pro Ser Asn Leu Thr Glu Asp Glu Phe
        130                 135                 140

Arg Gln Tyr Phe Gln Thr Tyr Gly Val Val Thr Asp Val Val Val Met
145                 150                 155                 160

-continued

Tyr Asp Gln Asn Thr Gln Arg Pro Arg Gly Phe Gly Phe Ile Thr Phe
                165                 170                 175

Asp Ala Glu Asp Ala Val Asp Arg Val Leu His Lys Thr Phe His Asp
            180                 185                 190

Leu Ser Gly Lys Met Val Glu Val Lys Arg Ala Leu Pro Arg Glu Ala
        195                 200                 205

Asn Pro Gly Ser Gly Ser Gly Arg Ser Met Gly Gly Gly Gly
    210                 215                 220

Gly Tyr Gln Ser Asn Asn Gly Pro Asn Ser Asn Ser Gly Gly Tyr Asp
225                 230                 235                 240

Ser Arg Gly Asp Ala Ser Arg Tyr Gly Gln Ala Gln Gln Gly Ser Gly
                245                 250                 255

Gly Tyr Pro Gly Tyr Gly Ala Gly Tyr Gly Ala Gly Thr Val Gly
            260                 265                 270

Tyr Gly Tyr Gly His Ala Asn Pro Gly Thr Ala Tyr Gly Asn Tyr Gly
        275                 280                 285

Ala Gly Gly Phe Gly Gly Val Pro Ala Gly Tyr Gly Gly His Tyr Gly
    290                 295                 300

Asn Pro Asn Ala Pro Gly Ser Gly Tyr Gln Gly Gly Pro Pro Gly Ala
305                 310                 315                 320

Asn Arg Gly Pro Trp Gly Gly Gln Ala Pro Ser Gly Tyr Gly Thr Gly
                325                 330                 335

Ser Tyr Gly Gly Asn Ala Gly Tyr Ala Ala Trp Asn Asn Ser Ser Ala
            340                 345                 350

Gly Gly Asn Ala Pro Thr Ser Gln Ala Ala Gly Ala Gly Thr Gly Tyr
        355                 360                 365

Gly Ser Gln Gly Tyr Gly Tyr Gly Gly Tyr Gly Gly Asp Ala Ser Tyr
    370                 375                 380

Gly Asn His Gly Gly Tyr Gly Gly Tyr Gly Gly Arg Gly Asp Gly Ala
385                 390                 395                 400

Gly Asn Pro Ala Ala Gly Gly Gly Ser Gly Tyr Gly Ala Gly Tyr Gly
                405                 410                 415

Ser Gly Asn Gly Gly Ser Gly Tyr Pro Asn Ala Trp Ala Asp Pro Ser
            420                 425                 430

Gln Gly Gly Gly Phe Gly Ala Ser Val Asn Gly Val Ser Glu Gly Gln
        435                 440                 445

Ser Asn Tyr Gly Ser Gly Tyr Gly Gly Val Gln Pro Arg Val Ala Gln
    450                 455                 460

<210> SEQ ID NO 30
<211> LENGTH: 2469
<212> TYPE: DNA
<213> ORGANISM: Oryza sativa

<400> SEQUENCE: 30
ggtccattat ttataccatt tccgcgtccc cccaccctcc tccccgctt tcccaatcga      60 ggcgagcacc gcaattgcag ggttccggag gccgaataaa aagtttggc ctctccccgc     120 aaaaaagtaa aaacccaaa acaaccatcc accagcgcat cgcggcaccg cgagcgagcg     180
agcggaggga gggaggtgga gagcaaaagt tcgataaaag gagaggagga gacgaagcgt     240
cgaagcccaa gtaacatccc cccaacctcc gcctcctcct cctcccctc ctcccatgcc     300 cgcatcgaga tcttagccgc gccggagatc gagagggagg agcggcgacg cgggcgcccc     360
cgatccctcc tcctcgccgc cgccgccgcc ggcggcgccg gagcagcagc agccgacgac     420
gacgacgacc gccgcagcag ccgatcgggg gaggagggga ggggaggacg cgatggaggc     480

```
ggactccggg aagctcttcg tcggcggcat ctcgtgggag acggacgagg accgcctccg      540
cgagtacttc agccggttcg ggaggtcac cgaggccgtc atcatgcggg accgcaacac       600
cggccgcgcc cgtgggttcg gcttcgtggt cttcaccgac gcaggcgtcg ccgagcgggt      660
caccatggat aagcacatga tcgacgggcg catggtggaa gcgaagaaag ctgttcccag      720
ggacgaccag agcatcacca gcaagaacaa tggcagcagc atagggtcac ctggaccagg     780
ccgtactaga aagatctttg ttggaggctt ggcctctaat gttactgagg ttgaatttag     840
aaggtatttt gagcaatttg gtgtgattac ggatgtggtt gtcatgtacg accacaacac    900
gcagaggcct aggggctttg gattcatcac ctatgactca aagatgcgg tggacaaggc     960 actgcacaag aacttccatg agctgaatgg taagatggtt gaggtcaaga gagctgttcc   1020
aaaggagcaa tcacctggac ctgctgcacg ttcacctgcg ggagggcaga actatgctat   1080
gagcagggtc catagcttct tgaatggttt caaccagggt tataacccaa accctattgg   1140
aggttatggc atgagggttg atggaaggta tggtctgctt acaggcgcac ggaatggatt   1200
ctcttcattt ggccctggtt atggaatggg catgaattct gaatctggga tgaatgcgaa   1260
ttttggcgcc aattctagtt ttgtcaataa ctccaatggg cggcagatag gttcattcta   1320
caatggtagt tcaaacagat taggtagtcc tattggttat gttggtctta atgatgattc   1380
aggatcacta ttgagttcaa tgtcaaggaa tgtttgggt aatgaaaatc tgaactaccc    1440
aaacaacccc acaaacatga gttcttttgc accatctgga actggaggtc aaatgggtat   1500
taccagtgac ggtattaatt ggggagggcc tactcctggc catggaatgg gcaacatttc   1560
aagccttggg ctggctaacc ttggccgtgg agctggagac agttttggct gccttctgg    1620 cagctatgga aggagcaatg caactggtac cattggtgaa cccttctctg caccaccaa    1680 tgcatatgaa gtgaacaatg cagatacata tggcagcagc tccatttatg gagactcaac   1740
ttggaggttc acgtcatctg agattgatat gcctcctttt ggtaatgacc ttggaaatgt   1800
tgatccagat atcaaatcaa acataccagc aagttacatg gcaactata ctgttaataa    1860 taatcagaca agcagaggta tcacttccta gcgagagtac tattatattc atatatgact   1920
tgggatagat gaaagaagca ttatatcagg tattcaggtg catgactatg aattggtgat   1980
atcaggttaa tatacgggtt agttaattgt ttctagctaa ccagaggtgt ggtttatgga   2040
caccaccatg ctagaggagc gaatacaaac gttttgtgaa ggtttcagat tttagtttaa   2100
ttcctacatg tattaggtct tggttttga atgagatgtg cagtggtgat tgcggcacat    2160
acttagagtg ttccaacata agctggaatc ctgtcatatg gacaaacttg tataccaaag   2220
gaatgcttta ttatcttgcc catttatggc tacattagct cgcttgtttt cattccttt    2280 ttaaccaatt ccatttgtat actagagatc tgcttgactt actagtgaaa ctattcgggg   2340
acgccgatcc tatctttgca gttggctccc agaaataaag ccaccaaaag tgcatactta   2400
tttgttctac cttgatttgc catatgtata tgcttctgtt cgttttaaaa tagaactttg   2460
ggtttgatt                                                             2469
```

<210> SEQ ID NO 31
<211> LENGTH: 472
<212> TYPE: PRT
<213> ORGANISM: Oryza sativa

<400> SEQUENCE: 31

```
Met Glu Ala Asp Ser Gly Lys Leu Phe Val Gly Gly Ile Ser Trp Glu
1               5                   10                  15
```

-continued

```
Thr Asp Glu Asp Arg Leu Arg Glu Tyr Phe Ser Arg Phe Gly Val
             20                  25                  30

Thr Glu Ala Val Ile Met Arg Asp Arg Asn Thr Gly Arg Ala Arg Gly
         35                  40                  45

Phe Gly Phe Val Val Phe Thr Asp Ala Gly Val Ala Glu Arg Val Thr
 50                  55                  60

Met Asp Lys His Met Ile Asp Gly Arg Met Val Glu Ala Lys Lys Ala
 65                  70                  75                  80

Val Pro Arg Asp Asp Gln Ser Ile Thr Ser Lys Asn Asn Gly Ser Ser
             85                  90                  95

Ile Gly Ser Pro Gly Pro Gly Arg Thr Arg Lys Ile Phe Val Gly Gly
             100                 105                 110

Leu Ala Ser Asn Val Thr Glu Val Glu Phe Arg Arg Tyr Phe Glu Gln
             115                 120                 125

Phe Gly Val Ile Thr Asp Val Val Met Tyr Asp His Asn Thr Gln
 130                 135                 140

Arg Pro Arg Gly Phe Gly Phe Ile Thr Tyr Asp Ser Glu Asp Ala Val
145                 150                 155                 160

Asp Lys Ala Leu His Lys Asn Phe His Glu Leu Asn Gly Lys Met Val
             165                 170                 175

Glu Val Lys Arg Ala Val Pro Lys Glu Gln Ser Pro Gly Pro Ala Ala
             180                 185                 190

Arg Ser Pro Ala Gly Gly Gln Asn Tyr Ala Met Ser Arg Val His Ser
     195                 200                 205

Phe Leu Asn Gly Phe Asn Gln Gly Tyr Asn Pro Asn Pro Ile Gly Gly
 210                 215                 220

Tyr Gly Met Arg Val Asp Gly Arg Tyr Gly Leu Leu Thr Gly Ala Arg
225                 230                 235                 240

Asn Gly Phe Ser Ser Phe Gly Pro Gly Tyr Gly Met Gly Met Asn Ser
             245                 250                 255

Glu Ser Gly Met Asn Ala Asn Phe Gly Ala Asn Ser Ser Phe Val Asn
             260                 265                 270

Asn Ser Asn Gly Arg Gln Ile Gly Ser Phe Tyr Asn Gly Ser Ser Asn
             275                 280                 285

Arg Leu Gly Ser Pro Ile Gly Tyr Val Gly Leu Asn Asp Asp Ser Gly
 290                 295                 300

Ser Leu Leu Ser Ser Met Ser Arg Asn Val Trp Gly Asn Glu Asn Leu
305                 310                 315                 320

Asn Tyr Pro Asn Asn Pro Thr Asn Met Ser Ser Phe Ala Pro Ser Gly
             325                 330                 335

Thr Gly Gly Gln Met Gly Ile Thr Ser Asp Gly Ile Asn Trp Gly Gly
             340                 345                 350

Pro Thr Pro Gly His Gly Met Gly Asn Ile Ser Ser Leu Gly Leu Ala
             355                 360                 365

Asn Leu Gly Arg Gly Ala Gly Asp Ser Phe Gly Leu Pro Ser Gly Ser
 370                 375                 380

Tyr Gly Arg Ser Asn Ala Thr Gly Thr Ile Gly Glu Pro Phe Ser Ala
385                 390                 395                 400

Pro Pro Asn Ala Tyr Glu Val Asn Asn Ala Asp Thr Tyr Gly Ser Ser
             405                 410                 415

Ser Ile Tyr Gly Asp Ser Thr Trp Arg Phe Thr Ser Ser Glu Ile Asp
             420                 425                 430

Met Pro Pro Phe Gly Asn Asp Leu Gly Asn Val Asp Pro Asp Ile Lys
             435                 440                 445
```

```
Ser Asn Ile Pro Ala Ser Tyr Met Gly Asn Tyr Thr Val Asn Asn Asn
    450                 455                 460

Gln Thr Ser Arg Gly Ile Thr Ser
465                 470

<210> SEQ ID NO 32
<211> LENGTH: 2315
<212> TYPE: DNA
<213> ORGANISM: Oryza sativa

<400> SEQUENCE: 32
ttggagatag aatagagaga gacacacaaa cacctacaac accaacaaca acaagagaaa      60
gagagaaaga agagaaggaa aggagaggaa gaagaggtgg tggtggtggt ggtggtggtg     120
tgtggcctcc ttccctccc tcctctcgcg aggttgccat gcctccccca agatcgatcc      180
aacccgatca tcaatcgggg cggggaagga ggaggagggg atggaggcgg acgccgggaa    240
gctgttcatc ggcggcatct cgtgggacac caacgaggac cgcctccgcg agtacttcga    300
caagtacggc gaggtggtgg aggccgtcat catgcgcgac cgcgccaccg gccgcgcccg    360
gggattcggc ttcatcgtct tcgctgaccc tgccgtcgcc gagcgggtca ttatggagaa    420
gcacatgatc gatggccgca tggtggaggc gaagaaagct gttcccaggg acgatcagca    480
cgctcttagc aagagcggcg ggagcgctca tggatcgccg gggcccagcc gcaccaagaa    540
gatattcgtt gggggctag cgtccaccgt gacggaggcg gacttcagga agtactttga    600
gcagttcggg acgatcaccg atgtcgtggt gatgtatgat cacaacacgc agcgtcccag    660
aggttttggg ttcattacgt acgattcgga ggatgctgtg gacaaggcat tgttcaagac    720
cttccatgaa ctgaacggta agatggttga ggtcaagcgc gcggttccta aggaactatc    780
acctgggcct agcatgcgtt ctcctgtcgg tggattcaac tatgccgtga acagagccaa    840
taacttcctc aatggataca cccagggtta taatccgagc ccagtcggtg gctatggaat    900
gaggatggat gcaaggtttg ggcttctatc gggtggccgt agtagttatc cttcttttgg    960
tggtggttat ggagtcggta tgaattttga tccagggatg aaccctgcta ttgggggaag   1020
ctcaagcttc aacaacagtc tccagtatgg aaggcagctt aatccatact acagtggaaa   1080
ttctggtaga tacaatagca atgttagcta tggtggagtc aatgacagta ctgggtcagt   1140
gttcaactcg ctggctcgta atttatgggg taattcaggt cttagttact cttccaactc   1200
tgcaagctct aattccttca tgtcatctgc caatggggc cttggtggaa ttgggaacaa    1260
caatgtgaat tggggaaacc ctcctgtgcc tgcacaaggt gctaatgctg cccaggcta    1320 tggcagtggg aacttcggtt atggatccag tgaaaccaac tttggtctcg gtaccaatgc    1380
ttatggaagg aatgctggat ctggtgttgt taatacattc aatcaatcaa ccaatgggta    1440
tggaaggaac tttggagatt catcaggagg aggtggcggt ggtggcggtg gctccatcta    1500
tggagacaca acttggagat ccggatcttc tgagcttgat ggaaccagcc catttggcta    1560
tgggcttggg aatgcagctt cagatgttac agcaaagaac tcagcaggtt acatggggca    1620
ttaacaaata gagcaatgtc gccgcctagg aatcttttc acatcaaca tttgtcaaaa     1680 taggttgagg agagaaccac aggtgcatca ggtgcaaatt ttgaacctca catgatttac    1740
agaaatgggt tagttaatag agctaaccac cagggatttg gtcaatgaga tcagatatat    1800
atcctcagag aaccatttaa acgtatttcc attttatgta aggtttgaga ttgtggtttc    1860
ggatttctac agcgagttta ggttttggca accttgtgtt ttttcttggt tgagatgtga    1920
agtaagattg cgggatatat atatctgaag agtgttcagt tgtacggcgg cgctgccccc    1980
```

-continued

```
atataggccc ccctttttgg gtttttgttc ttatagtaga aactgctcta gcgttttgca    2040
aattgtgtgc tagctgttgt tatcaggatg ataattttt tccccttctt ggtttttatc     2100
ttactgaagt gtatgtacca gagatcttgc tggtctgtgt ttttcctagt ggaacttttg    2160
agggatgccc cttctgggtc tcaaagaata ataatgctac attatattct aattcatttt    2220
gaggctttct aaggctatat attatttgta tgtaccctgc tggaacatct gtacattctg    2280
atgctctttg caatttgcct ttgtgctgct tttgc                               2315

<210> SEQ ID NO 33
<211> LENGTH: 467
<212> TYPE: PRT
<213> ORGANISM: Oryza sativa

<400> SEQUENCE: 33

Met Glu Ala Asp Ala Gly Lys Leu Phe Ile Gly Gly Ile Ser Trp Asp
1               5                   10                  15

Thr Asn Glu Asp Arg Leu Arg Glu Tyr Phe Asp Lys Tyr Gly Glu Val
                20                  25                  30

Val Glu Ala Val Ile Met Arg Asp Arg Ala Thr Gly Arg Ala Arg Gly
            35                  40                  45

Phe Gly Phe Ile Val Phe Ala Asp Pro Ala Val Ala Glu Arg Val Ile
        50                  55                  60

Met Glu Lys His Met Ile Asp Gly Arg Met Val Glu Ala Lys Lys Ala
65                  70                  75                  80

Val Pro Arg Asp Asp Gln His Ala Leu Ser Lys Ser Gly Gly Ser Ala
                85                  90                  95

His Gly Ser Pro Gly Pro Ser Arg Thr Lys Lys Ile Phe Val Gly Gly
                100                 105                 110

Leu Ala Ser Thr Val Thr Glu Ala Asp Phe Arg Lys Tyr Phe Glu Gln
            115                 120                 125

Phe Gly Thr Ile Thr Asp Val Val Val Met Tyr Asp His Asn Thr Gln
        130                 135                 140

Arg Pro Arg Gly Phe Gly Phe Ile Thr Tyr Asp Ser Glu Asp Ala Val
145                 150                 155                 160

Asp Lys Ala Leu Phe Lys Thr Phe His Glu Leu Asn Gly Lys Met Val
                165                 170                 175

Glu Val Lys Arg Ala Val Pro Lys Glu Leu Ser Pro Gly Pro Ser Met
            180                 185                 190

Arg Ser Pro Val Gly Gly Phe Asn Tyr Ala Val Asn Arg Ala Asn Asn
        195                 200                 205

Phe Leu Asn Gly Tyr Thr Gln Gly Tyr Asn Pro Ser Pro Val Gly Gly
    210                 215                 220

Tyr Gly Met Arg Met Asp Ala Arg Phe Gly Leu Leu Ser Gly Gly Arg
225                 230                 235                 240

Ser Ser Tyr Pro Ser Phe Gly Gly Tyr Gly Val Gly Met Asn Phe
                245                 250                 255

Asp Pro Gly Met Asn Pro Ala Ile Gly Gly Ser Ser Phe Asn Asn
                260                 265                 270

Ser Leu Gln Tyr Gly Arg Gln Leu Asn Pro Tyr Tyr Ser Gly Asn Ser
            275                 280                 285

Gly Arg Tyr Asn Ser Asn Val Ser Tyr Gly Val Asn Asp Ser Thr
        290                 295                 300

Gly Ser Val Phe Asn Ser Leu Ala Arg Asn Leu Trp Gly Asn Ser Gly
305                 310                 315                 320
```

```
Leu Ser Tyr Ser Ser Asn Ser Ala Ser Ser Asn Ser Phe Met Ser Ser
            325                 330                 335

Ala Asn Gly Gly Leu Gly Gly Ile Gly Asn Asn Asn Val Asn Trp Gly
        340                 345                 350

Asn Pro Pro Val Pro Ala Gln Gly Ala Asn Ala Gly Pro Gly Tyr Gly
            355                 360                 365

Ser Gly Asn Phe Gly Tyr Gly Ser Ser Glu Thr Asn Phe Gly Leu Gly
    370                 375                 380

Thr Asn Ala Tyr Gly Arg Asn Ala Gly Ser Gly Val Val Asn Thr Phe
385                 390                 395                 400

Asn Gln Ser Thr Asn Gly Tyr Gly Arg Asn Phe Gly Asp Ser Ser Gly
                405                 410                 415

Gly Gly Gly Gly Gly Gly Gly Ser Ile Tyr Gly Asp Thr Thr Trp
            420                 425                 430

Arg Ser Gly Ser Ser Glu Leu Asp Gly Thr Ser Pro Phe Gly Tyr Gly
    435                 440                 445

Leu Gly Asn Ala Ala Ser Asp Val Thr Ala Lys Asn Ser Ala Gly Tyr
    450                 455                 460

Met Gly His
465

<210> SEQ ID NO 34
<211> LENGTH: 1146
<212> TYPE: DNA
<213> ORGANISM: Triticum aestivum

<400> SEQUENCE: 34
aaaaagcagg tgggaccggc ccggaattct cgggatatcg tcgacccacg cgtccgcgca      60
cccgagcgcg agagaatccg aggagaggag cggcgcaagg aggcggtgat ggagtcggat     120
cagggcaagc tcttcatcgg cggcatctcc tgggagacga cggaggagaa gctgcaggag     180
cacttctcca acttcggcga ggtctcccag gccgccgtca tgcgcgacaa gctcactggc     240
cgcccgcggg gcttcggctt cgtagtctac gccgaccccg ccgccgtcga cgccgccctc     300
caggagcccc acaccctcga cggccgcacg gtcgatgtga agcgggcgct ctcgcgggag     360
gagcagcagg ctaccaaggc ggtgaaccct agcgcaggaa ggaacgctgg aggtggtggc     420
ggcggcggcg gcggcggcgg cgatgccggt ggtgctagga caaagaagat ttttgtgggc     480
ggactgccct ccagtctgac agatgaggag ttccggcagt acttccagac cttcggggct     540
gtcaccgatg ttgtggtgat gtatgaccag acaacacagc gtccccgggg cttcggcttc     600
attaccttg actcggagga tgcggttgac cgtgtgctgc acaaaacctt ccacgatctt     660
ggagggaaga tggtagaggt gaagcgtgct ctgccccgag aggcgaatcc tggctctggc     720
ggcggcggcc gttccatggg aggtgggggg tttcatagta acaatggacc ccactccaat     780
gctagcagct atgatggcag aggcgatgct agcagatatg gcaggcgca gcaaggcatg     840
ggtggctacc caggttatgg tgctggagct tatggcagtg ctccaactgg gtttggatat     900
gggccaccca atccgggaac tacttatgga aatattgggt ctgcagggtt aggagctttt     960
ccttggtgcg tatgcggggg gcttatgggc aacccaggtg gctgcgggtt tcgggttacc    1020
cgggggggcc cctccggggc cctaaataag ggacctgggg gcagccaaa cctccgccct    1080
ggtttatggc acctgggggc tttatcctgg gcacgtgcgg ggctattggg tgcgtggaaa    1140
taaccc                                                              1146
```

<210> SEQ ID NO 35
<211> LENGTH: 344
<212> TYPE: PRT
<213> ORGANISM: Triticum aestivum

<400> SEQUENCE: 35

Met Glu Ser Asp Gln Gly Lys Leu Phe Ile Gly Gly Ile Ser Trp Glu
1               5                   10                  15

Thr Thr Glu Glu Lys Leu Gln Glu His Phe Ser Asn Phe Gly Glu Val
            20                  25                  30

Ser Gln Ala Ala Val Met Arg Asp Lys Leu Thr Gly Arg Pro Arg Gly
        35                  40                  45

Phe Gly Phe Val Val Tyr Ala Asp Pro Ala Ala Val Asp Ala Ala Leu
    50                  55                  60

Gln Glu Pro His Thr Leu Asp Gly Arg Thr Val Asp Val Lys Arg Ala
65                  70                  75                  80

Leu Ser Arg Glu Glu Gln Gln Ala Thr Lys Ala Val Asn Pro Ser Ala
                85                  90                  95

Gly Arg Asn Ala Gly Gly Gly Gly Gly Gly Gly Gly Gly Gly Gly Asp
            100                 105                 110

Ala Gly Gly Ala Arg Thr Lys Lys Ile Phe Val Gly Gly Leu Pro Ser
        115                 120                 125

Ser Leu Thr Asp Glu Glu Phe Arg Gln Tyr Phe Gln Thr Phe Gly Ala
    130                 135                 140

Val Thr Asp Val Val Val Met Tyr Asp Gln Thr Thr Gln Arg Pro Arg
145                 150                 155                 160

Gly Phe Gly Phe Ile Thr Phe Asp Ser Glu Asp Ala Val Asp Arg Val
                165                 170                 175

Leu His Lys Thr Phe His Asp Leu Gly Gly Lys Met Val Glu Val Lys
            180                 185                 190

Arg Ala Leu Pro Arg Glu Ala Asn Pro Gly Ser Gly Gly Gly Gly Arg
        195                 200                 205

Ser Met Gly Gly Gly Gly Phe His Ser Asn Asn Gly Pro His Ser Asn
    210                 215                 220

Ala Ser Ser Tyr Asp Gly Arg Gly Asp Ala Ser Arg Tyr Gly Gln Ala
225                 230                 235                 240

Gln Gln Gly Met Gly Gly Tyr Pro Gly Tyr Gly Ala Gly Ala Tyr Gly
                245                 250                 255

Ser Ala Pro Thr Gly Phe Gly Tyr Gly Pro Asn Pro Gly Thr Thr
            260                 265                 270

Tyr Gly Asn Ile Gly Ser Ala Gly Leu Gly Ala Phe Pro Trp Cys Val
        275                 280                 285

Cys Gly Gly Leu Met Gly Asn Pro Gly Gly Cys Gly Phe Arg Val Thr
    290                 295                 300

Arg Gly Gly Pro Ser Gly Ala Leu Asn Lys Gly Pro Trp Gly Gln Pro
305                 310                 315                 320

Asn Leu Arg Pro Gly Leu Trp His Leu Gly Ala Leu Ser Trp Ala Arg
                325                 330                 335

Ala Gly Leu Leu Gly Ala Trp Lys
            340

<210> SEQ ID NO 36
<211> LENGTH: 800
<212> TYPE: DNA
<213> ORGANISM: Saccharum officinarum
<220> FEATURE:
<221> NAME/KEY: misc_feature

```
<222> LOCATION: (8)..(8)
<223> OTHER INFORMATION: n is a, c, g, or t
<220> FEATURE:
<221> NAME/KEY: misc_feature
<222> LOCATION: (381)..(381)
<223> OTHER INFORMATION: n is a, c, g, or t
<220> FEATURE:
<221> NAME/KEY: misc_feature
<222> LOCATION: (425)..(425)
<223> OTHER INFORMATION: n is a, c, g, or t
<220> FEATURE:
<221> NAME/KEY: misc_feature
<222> LOCATION: (428)..(428)
<223> OTHER INFORMATION: n is a, c, g, or t
<220> FEATURE:
<221> NAME/KEY: misc_feature
<222> LOCATION: (481)..(481)
<223> OTHER INFORMATION: n is a, c, g, or t
<220> FEATURE:
<221> NAME/KEY: misc_feature
<222> LOCATION: (514)..(514)
<223> OTHER INFORMATION: n is a, c, g, or t

<400> SEQUENCE: 36
agaattcncg gttcgaccta cgcgtccgcc cggaatcccc aattccgctc tcttcctctc      60
tccctctctc ccccaccgca gcatcaggcg agcgcgaggc ggaggtggag gagagatgga     120
gttggaccag ggcaagctct tcatcggcgg catctcctgg agacgacgg aggagaagct      180 gagcgagcac ttctccgcct acggcgaggt tacgcaggcc gccgtcatgc gggacaagat     240
caccggccgc ccccgtggct tcgggttcgt cgtcttcgcc gaccccgccg tcgtcgaccg     300
agcgctgcag gacccccaca ccctcgacgg ccgcacggtc gatgtgaagc gggcactctc     360
gcgggaggag cagcaggcct ncaaggccgc gaaccctagc ggtgggagga acactggcgg     420
tggangangc ggcgggtggc ggggcggcga tgcaagtggt gctcggaccc aggaagatct     480 ntgggggcc ggcttgcctt ctactctgac tganggatgg gtttcggcag tactttccgg      540
accttcggag gggtcactga tggttggtgg ccatggttga accggaacaa gcaattgccc     600
gcgttggttt tggaatcaat acttttgaac tttaagattc cggtgaaccg ctgctggcca     660
agaactttca tgacctggtg ggaagatggt ttaaggtgaa ccagcattgc gcccttgagg     720
cgaaccctgg gggttctgga acgggccgtt ctggggggaaa tgggggcttt ctagcaacca    780
tggccttacc cccgttttgg                                                 800

<210> SEQ ID NO 37
<211> LENGTH: 154
<212> TYPE: PRT
<213> ORGANISM: Saccharum officinarum
<220> FEATURE:
<221> NAME/KEY: misc_feature
<222> LOCATION: (89)..(89)
<223> OTHER INFORMATION: Xaa can be any naturally occurring amino acid
<220> FEATURE:
<221> NAME/KEY: misc_feature
<222> LOCATION: (104)..(105)
<223> OTHER INFORMATION: Xaa can be any naturally occurring amino acid
<220> FEATURE:
<221> NAME/KEY: misc_feature
<222> LOCATION: (133)..(133)
<223> OTHER INFORMATION: Xaa can be any naturally occurring amino acid

<400> SEQUENCE: 37

Met Glu Leu Asp Gln Gly Lys Leu Phe Ile Gly Gly Ile Ser Trp Glu
1               5                   10                  15

Thr Thr Glu Glu Lys Leu Ser Glu His Phe Ser Ala Tyr Gly Glu Val
            20                  25                  30

Thr Gln Ala Ala Val Met Arg Asp Lys Ile Thr Gly Arg Pro Arg Gly
```

```
                    35                  40                  45
Phe Gly Phe Val Val Phe Ala Asp Pro Ala Val Asp Arg Ala Leu
 50                  55                  60

Gln Asp Pro His Thr Leu Asp Gly Arg Thr Val Asp Val Lys Arg Ala
 65                  70                  75                  80

Leu Ser Arg Glu Glu Gln Ala Xaa Lys Ala Ala Asn Pro Ser Gly
                 85                  90                  95

Gly Arg Asn Thr Gly Gly Xaa Xaa Gly Gly Trp Arg Gly Asp
                100                 105                 110

Ala Ser Gly Ala Arg Thr Gln Glu Asp Leu Trp Gly Ala Gly Leu Pro
            115                 120                 125

Ser Thr Leu Thr Xaa Gly Trp Val Ser Ala Val Leu Ser Gly Pro Ser
            130                 135                 140

Glu Gly Ser Leu Met Val Gly Gly His Gly
145                 150
```

<210> SEQ ID NO 38
<211> LENGTH: 1243
<212> TYPE: DNA
<213> ORGANISM: Oryza sativa

<400> SEQUENCE: 38

```
aaaaccaccg agggacctga tctgcaccgg ttttgatagt tgagggaccc gttgtgtctg    60
gttttccgat cgagggacga aaatcggatt cggtgtaaag ttaagggacc tcagatgaac   120
ttattccgga gcatgattgg gaagggagga cataaggccc atgtcgcatg tgtttggacg   180
gtccagatct ccagatcact cagcaggatc ggccgcgttc gcgtagcacc cgcggtttga   240
ttcggcttcc cgcaaggcgg cggccggtgg ccgtgccgcc gtagcttccg ccggaagcga   300
gcacgccgcc gccgccgacc cggctctgcg tttgcaccgc cttgcacgcg atacatcggg   360
atagatagct actactctct ccgtttcaca atgtaaatca ttctactatt ttccacattc   420
atattgatgt taatgaatat agacatatat atctatttag attcattaac atcaatatga   480
atgtaggaaa tgctagaatg acttacattg tgaattgtga atggacgaa gtacctacga   540
tggatggatg caggatcatg aaagaattaa tgcaagatcg tatctgccgc atgcaaaatc   600
ttactaattg cgctgcatat atgcatgaca gcctgcatgc gggcgtgtaa gcgtgttcat   660
ccattaggaa gtaaccttgt cattacttat accagtacta catactatat agtattgatt   720
tcatgagcaa atctacaaaa ctggaaagca ataagaaata cgggactgga aaagactcaa   780
cattaatcac caaatatttc gccttctcca gcagaatata tatctctcca tcttgatcac   840
tgtacacact gacagtgtac gcataaacgc agcagccagc ttaactgtcg tctcaccgtc   900
gcacactggc cttccatctc aggctagctt tctcagccac ccatcgtaca tgtcaactcg   960
gcgcgcgcac aggcacaaat tacgtacaaa acgcatgacc aaatcaaaac caccggagaa  1020
gaatcgctcc cgcgcgcggc ggcgacgcgc acgtacgaac gcacgcacgc acgcccaacc  1080
ccacgacacg atcgcgcgcg acgccggcga caccggccgt ccaccgcgc cctcacctcg  1140
ccgactataa atacgtaggc atctgcttga tcttgtcatc catctcacca ccaaaaaaaa  1200
aaggaaaaaa aaacaaaaca caccaagcca ataaaagcg aca                     1243
```

<210> SEQ ID NO 39
<211> LENGTH: 59
<212> TYPE: DNA
<213> ORGANISM: Artificial sequence
<220> FEATURE:
<223> OTHER INFORMATION: primer: prm00405

-continued

<400> SEQUENCE: 39
ggggacaagt ttgtacaaaa aagcaggctt cacaatggat tatgatcggt acaagttat    59

<210> SEQ ID NO 40
<211> LENGTH: 54
<212> TYPE: DNA
<213> ORGANISM: Artificial sequence
<220> FEATURE:
<223> OTHER INFORMATION: primer: prm00406

<400> SEQUENCE: 40
ggggaccact ttgtacaaga aagctgggtt taaaagagtc caaagaattt cact    54

<210> SEQ ID NO 41
<211> LENGTH: 7
<212> TYPE: PRT
<213> ORGANISM: Artificial sequence
<220> FEATURE:
<223> OTHER INFORMATION: Motif (i)

<400> SEQUENCE: 41

Lys Ile Phe Val Gly Gly Leu
1               5

<210> SEQ ID NO 42
<211> LENGTH: 7
<212> TYPE: PRT
<213> ORGANISM: Artificial sequence
<220> FEATURE:
<223> OTHER INFORMATION: Motif (ii)

<400> SEQUENCE: 42

Arg Pro Arg Gly Phe Gly Phe
1               5

<210> SEQ ID NO 43
<211> LENGTH: 411
<212> TYPE: PRT
<213> ORGANISM: Arabidopsis thaliana

<400> SEQUENCE: 43

Met Asp Ser Asp Gln Gly Lys Leu Phe Val Gly Gly Ile Ser Trp Glu
1               5                   10                  15

Thr Asp Glu Asp Lys Leu Arg Glu His Phe Thr Asn Tyr Gly Glu Val
            20                  25                  30

Ser Gln Ala Ile Val Met Arg Asp Lys Leu Thr Gly Arg Pro Arg Gly
        35                  40                  45

Phe Gly Phe Val Ile Phe Ser Asp Pro Ser Val Leu Asp Arg Val Leu
    50                  55                  60

Gln Glu Lys His Ser Ile Asp Thr Arg Glu Val Asp Val Lys Arg Ala
65                  70                  75                  80

Met Ser Arg Glu Glu Gln Gln Val Ser Gly Arg Thr Gly Asn Leu Asn
                85                  90                  95

Thr Ser Arg Ser Ser Gly Gly Asp Ala Tyr Asn Lys Thr Lys Lys Ile
            100                 105                 110

Phe Val Gly Gly Leu Pro Pro Thr Leu Thr Asp Glu Glu Phe Arg Gln
        115                 120                 125

Tyr Phe Glu Val Tyr Gly Pro Val Thr Asp Val Ala Ile Met Tyr Asp
    130                 135                 140

Gln Ala Thr Asn Arg Pro Arg Gly Phe Gly Phe Val Ser Phe Asp Ser
145                 150                 155                 160

Glu Asp Ala Val Asp Ser Val Leu His Lys Thr Phe His Asp Leu Ser
                165                 170                 175

Gly Lys Gln Val Glu Val Lys Arg Ala Leu Pro Lys Asp Ala Asn Pro
            180                 185                 190

Gly Gly Gly Gly Arg Ser Met Gly Gly Gly Ser Gly Gly Tyr Gln
        195                 200                 205

Gly Tyr Gly Gly Asn Glu Ser Ser Tyr Asp Gly Arg Met Asp Ser Asn
    210                 215                 220

Arg Phe Leu Gln His Gln Ser Val Gly Asn Gly Leu Pro Ser Tyr Gly
225                 230                 235                 240

Ser Ser Gly Tyr Gly Ala Gly Tyr Gly Asn Gly Ser Asn Gly Ala Gly
                245                 250                 255

Tyr Gly Ala Tyr Gly Gly Tyr Thr Gly Ser Ala Gly Gly Tyr Gly Ala
            260                 265                 270

Gly Ala Thr Ala Gly Tyr Gly Ala Thr Asn Ile Pro Gly Ala Gly Tyr
        275                 280                 285

Gly Ser Ser Thr Gly Val Ala Pro Arg Asn Ser Trp Asp Thr Pro Ala
    290                 295                 300

Ser Ser Gly Tyr Gly Asn Pro Gly Tyr Gly Ser Gly Ala Ala His Ser
305                 310                 315                 320

Gly Tyr Gly Val Pro Gly Ala Ala Pro Pro Thr Gln Ser Pro Ser Gly
                325                 330                 335

Tyr Ser Asn Gln Gly Tyr Gly Tyr Gly Gly Tyr Ser Gly Ser Asp Ser
            340                 345                 350

Gly Tyr Gly Asn Gln Ala Ala Tyr Gly Val Val Gly Gly Arg Pro Ser
        355                 360                 365

Gly Gly Gly Ser Asn Asn Pro Gly Ser Gly Gly Tyr Met Gly Gly Gly
    370                 375                 380

Tyr Gly Asp Gly Ser Trp Arg Ser Asp Pro Ser Gln Gly Tyr Gly Gly
385                 390                 395                 400

Gly Tyr Asn Asp Gly Gln Gly Arg Gln Gly Gln
                405                 410

<210> SEQ ID NO 44
<211> LENGTH: 495
<212> TYPE: PRT
<213> ORGANISM: Arabidopsis thaliana

<400> SEQUENCE: 44

Met Gln Ser Asp Asn Gly Lys Leu Phe Ile Gly Ile Ser Trp Asp
1               5                   10                  15

Thr Asn Glu Glu Arg Leu Lys Glu Tyr Phe Ser Ser Phe Gly Glu Val
            20                  25                  30

Ile Glu Ala Val Ile Leu Lys Asp Arg Thr Thr Gly Arg Ala Arg Gly
        35                  40                  45

Phe Gly Phe Val Val Phe Ala Asp Pro Ala Val Ala Glu Ile Val Ile
    50                  55                  60

Thr Glu Lys His Asn Ile Asp Gly Arg Leu Val Glu Ala Lys Lys Ala
65                  70                  75                  80

Val Pro Arg Asp Asp Gln Asn Met Val Asn Arg Ser Asn Ser Ser Ser
                85                  90                  95

Ile Gln Gly Ser Pro Gly Gly Pro Gly Arg Thr Arg Lys Ile Phe Val
            100                 105                 110

Gly Gly Leu Pro Ser Ser Val Thr Glu Ser Asp Phe Lys Thr Tyr Phe
        115                 120                 125

Glu Gln Phe Gly Thr Thr Thr Asp Val Val Met Tyr Asp His Asn
    130                 135                 140

Thr Gln Arg Pro Arg Gly Phe Gly Phe Ile Thr Tyr Asp Ser Glu Glu
145                 150                 155                 160

Ala Val Glu Lys Val Leu Leu Lys Thr Phe His Glu Leu Asn Gly Lys
                165                 170                 175

Met Val Glu Val Lys Arg Ala Val Pro Lys Glu Leu Ser Pro Gly Pro
            180                 185                 190

Ser Arg Ser Pro Leu Gly Ala Gly Tyr Ser Tyr Gly Val Asn Arg Val
        195                 200                 205

Asn Asn Leu Leu Asn Gly Tyr Ala Gln Gly Phe Asn Pro Ala Ala Val
    210                 215                 220

Gly Gly Tyr Gly Leu Arg Met Asp Gly Arg Phe Ser Pro Val Gly Ala
225                 230                 235                 240

Gly Arg Ser Gly Phe Ala Asn Tyr Ser Ser Gly Tyr Gly Met Asn Val
                245                 250                 255

Asn Phe Asp Gln Gly Leu Pro Thr Gly Phe Thr Gly Gly Thr Asn Tyr
            260                 265                 270

Asn Gly Asn Val Asp Tyr Gly Arg Gly Met Ser Pro Tyr Tyr Ile Gly
        275                 280                 285

Asn Thr Asn Arg Phe Gly Pro Ala Val Gly Tyr Glu Gly Gly Asn Gly
    290                 295                 300

Gly Gly Asn Ser Ser Phe Phe Ser Ser Val Thr Arg Asn Leu Trp Gly
305                 310                 315                 320

Asn Asn Gly Gly Leu Asn Tyr Asn Asn Asn Thr Asn Ser Asn Ser
                325                 330                 335

Asn Thr Tyr Met Gly Gly Ser Ser Gly Asn Asn Thr Leu Ser Gly
            340                 345                 350

Pro Phe Gly Asn Ser Gly Val Asn Trp Gly Ala Pro Gly Gly Gly Asn
        355                 360                 365

Asn Ala Val Ser Asn Glu Asn Val Lys Phe Gly Tyr Gly Gly Asn Gly
    370                 375                 380

Glu Ser Gly Phe Gly Leu Gly Thr Gly Gly Tyr Ala Ala Arg Asn Pro
385                 390                 395                 400

Gly Ala Asn Lys Ala Ala Pro Ser Ser Ser Phe Ser Ser Ala Ser Ala
                405                 410                 415

Thr Asn Asn Thr Gly Tyr Asp Thr Ala Gly Leu Ala Glu Phe Tyr Gly
            420                 425                 430

Asn Gly Ala Val Tyr Ser Asp Pro Thr Trp Arg Ser Pro Thr Pro Glu
        435                 440                 445

Thr Glu Gly Pro Ala Pro Phe Ser Tyr Gly Ile Gly Gly Gly Val Pro
    450                 455                 460

Ser Ser Asp Val Ser Ala Arg Ser Ser Ser Pro Gly Tyr Val Gly Ser
465                 470                 475                 480

Tyr Ser Val Asn Lys Arg Gln Pro Asn Arg Gly Glu Pro Ser Arg
                485                 490                 495

<210> SEQ ID NO 45
<211> LENGTH: 358
<212> TYPE: PRT
<213> ORGANISM: Arabidopsis thaliana

<400> SEQUENCE: 45

Met Val Glu Ala Lys Lys Ala Val Pro Arg Asp Asp His Val Val Phe
1               5                   10                  15

-continued

```
Asn Lys Ser Asn Ser Ser Leu Gln Gly Ser Pro Gly Pro Ser Asn Ser
         20                  25                  30
Lys Lys Ile Phe Val Gly Gly Leu Ala Ser Ser Val Thr Glu Ala Glu
         35                  40                  45
Phe Lys Lys Tyr Phe Ala Gln Phe Gly Met Ile Thr Asp Val Val Val
 50                      55                  60
Met Tyr Asp His Arg Thr Gln Arg Pro Arg Gly Phe Gly Phe Ile Ser
 65                  70                  75                  80
Tyr Asp Ser Glu Glu Ala Val Asp Lys Val Leu Gln Lys Thr Phe His
             85                  90                  95
Glu Leu Asn Gly Lys Met Val Glu Val Lys Leu Ala Val Pro Lys Asp
             100                 105                 110
Met Ala Leu Asn Thr Met Arg Asn Gln Met Asn Val Asn Ser Phe Gly
             115                 120                 125
Thr Ser Arg Ile Ser Ser Leu Leu Asn Glu Tyr Thr Gln Gly Phe Ser
130                 135                 140
Pro Ser Pro Ile Ser Gly Tyr Gly Val Lys Pro Glu Val Arg Tyr Ser
145                 150                 155                 160
Pro Ala Val Gly Asn Arg Gly Gly Phe Ser Pro Phe Gly His Gly Tyr
                 165                 170                 175
Gly Ile Glu Leu Asn Phe Glu Pro Asn Gln Thr Gln Asn Tyr Gly Ser
             180                 185                 190
Gly Ser Ser Gly Gly Phe Gly Arg Pro Phe Ser Pro Gly Tyr Ala Ala
             195                 200                 205
Ser Leu Gly Arg Phe Gly Ser Gln Met Glu Ser Gly Gly Ala Ser Val
     210                 215                 220
Gly Asn Gly Ser Val Leu Asn Ala Ala Pro Lys Asn His Leu Trp Gly
225                 230                 235                 240
Asn Gly Gly Leu Gly Tyr Met Ser Asn Ser Pro Ile Ser Arg Ser Ser
                 245                 250                 255
Phe Ser Gly Asn Ser Gly Met Ser Ser Leu Gly Ser Ile Gly Asp Asn
                 260                 265                 270
Trp Gly Thr Val Ala Arg Ala Arg Ser Ser Tyr His Gly Glu Arg Gly
         275                 280                 285
Gly Val Gly Leu Glu Ala Met Arg Gly Val His Val Gly Gly Tyr Ser
         290                 295                 300
Ser Gly Ser Ser Ile Leu Glu Ala Asp Ser Leu Tyr Ser Asp Ser Met
305                 310                 315                 320
Trp Leu Ser Leu Pro Ala Lys Ala Glu Glu Gly Leu Gly Met Gly Pro
                 325                 330                 335
Leu Asp Phe Met Ser Arg Gly Pro Ala Gly Tyr Ile Asn Arg Gln Pro
             340                 345                 350
Asn Gly Gly Ile Ala Ala
             355
```

METHOD FOR INCREASING SEED YIELD OR BIOMASS BY EXPRESSING RNA BINDING PROTEINS IN TRANSGENIC PLANTS

RELATED APPLICATIONS

This application is a national stage application (under 35 U.S.C. 371) of PCT/EP2005/054034 filed Aug. 16, 2005, which claims benefit of European application 04103926.4 filed Aug. 16, 2004 and US Provisional application 60/602,680 filed Aug. 19, 2004.

SUBMISSION OF SEQUENCE LISTING

The Sequence Listing associated with this application is filed in electronic format via EFS-Web and hereby incorporated by reference into the specification in its entirety. The name of the text file containing the Sequence Listing is Sequence_Listing_32279_00027. The size of the text file is 127 KB, and the text file was created on Oct. 10, 2011.

The present invention relates generally to the field of molecular biology and concerns a method for improving plant growth characteristics. More specifically, the present invention concerns a method for improving plant growth characteristics, in particular yield, by increasing activity in a plant of an RNA-binding protein or a homologue thereof. The present invention also concerns plants having increased activity of an RNA-binding protein or a homologue thereof, which plants have improved growth characteristics relative to corresponding wild type plants. The RNA-binding protein or homologue thereof useful in the methods of the invention is one having RNA binding activity and having either 2 or 3 RNA recognition motifs (RRMs) and which comprises a motif having at least 75% sequence identity to motif I: PYEAAVVALPVVVKERLVRILRLGIATRYD (SEQ ID NO: 12) and/or a motif having at least 50% sequence identity to motif II: RFDPFTGEPYKFDP (SEQ ID NO: 13). The RNA-Zone binding protein or homologue thereof useful in the methods of the invention may also be an RBP1 or homologue thereof having the following: (a) RNA-binding activity; (b) two RRM domains, (c) the following two motifs: (i) KIFVGGL (SEQ ID NO: 41); and (ii) RPRGFGF (SEQ ID NO: 42), allowing for up to three amino acid substitutions and any conservative change in the motifs; and (d) having, in increasing order of preference, at least 20%, 25%, 30%, 35%, 40%, 45%, 50%, 55%, 60%, 65%, 70%, 75%, 80%, 85%, 90%, 95% sequence identity to the amino acid represented by SEQ ID NO: 15. The invention also provides constructs useful in the methods of the invention.

The ever-increasing world population and the dwindling supply of arable land available for agriculture fuel agricultural research towards improving the efficiency of agriculture. Conventional means for crop and horticultural improvements utilise selective breeding techniques to identify plants having desirable characteristics. However, such selective breeding techniques have several drawbacks, namely that these techniques are typically labour intensive and result in plants that often contain heterogeneous genetic components that may not always result in the desirable trait being passed on from parent plants. Advances in molecular biology have allowed mankind to modify the germplasm of animals and plants. Genetic engineering of plants entails the isolation and manipulation of genetic material (typically in the form of DNA or RNA) and the subsequent introduction of that genetic material into a plant. Such technology has the capacity to deliver crops or plants having various improved economic, agronomic or horticultural traits. A trait of particular economic interest is yield. Yield is normally defined as the measurable produce of economic value from a crop. This may be defined in terms of quantity and/or quality. Yield is directly dependent on several factors, for example, the number and size of the organs, plant architecture (for example, the number of branches), seed production and more. Root development, nutrient uptake and stress tolerance may also be important factors in determining yield. Crop yield may therefore be increased by optimizing one of the abovementioned factors.

The ability to improve various growth characteristics of a plant would have many applications in areas such as crop enhancement, plant breeding, in the production of ornamental plants, aboriculture, horticulture and forestry. Improving growth characteristics, such as yield may also find use in the production of algae for use in bioreactors (for the biotechnological production of substances such as pharmaceuticals, antibodies, or vaccines, or for the bioconversion of organic waste) and other such areas.

It has now been found that increasing activity in a plant of an RNA-binding protein or a homologue thereof gives plants having improved growth characteristics relative to corresponding wild type plants, which RNA-binding protein or homologue thereof has RNA binding activity and either 2 or 3 RNA recognition motifs (RRMs) and which comprises a motif having at least 75% sequence identity to motif I: PYEAAVVALPVVVKERLVRILRLGIATRYD (SEQ ID NO: 12) and/or a motif having at least 50% sequence identity to motif II: RFDPFTGEPYKFDP (SEQ ID NO: 13). It has also now been found that increasing activity in a plant of an RBP1 polypeptide or homologue thereof gives plants having improved growth characteristics relative to corresponding wild type plants. The RBP1 or homologue thereof refers to a polypeptide having the following: (a) RNA-binding activity; (b) two RRM domains, (c) the following two motifs: (i) KIFVGGL (SEQ ID NO: 41); and (ii) RPRGFGF (SEQ ID NO: 42), allowing for up to three amino acid substitutions and any conservative change in the motifs; and (d) having, in increasing order of preference, at least 20%, 25%, 30%, 35%, 40%, 45%, 50%, 55%, 60%, 65%, 70%, 75%, 80%, 85%, 90%, 95% sequence identity to the amino acid represented by SEQ ID NO: 15.

RNA-binding proteins have an important role to play in the regulation of gene expression both at a transcriptional and posttranscriptional level. The level of regulation extends over all steps in the synthesis, processing and turnover of RNA molecules, including pre-mRNA splicing, polyadenylation, mRNA transport, translation and stability/decay. Regulation is mainly achieved either directly by RNA-binding proteins or indirectly, whereby RNA-binding proteins modulate the function of other regulatory factors. RNA-protein interactions are central to many aspects of cellular metabolism, cell differentiation and development, as well as to the replication of infectious pathogens. RNA recognition motifs or RRMs are typically present in a large variety of RNA-binding proteins and are involved in all post-transcriptional processes, whereby the number of RRMs per protein varies from one to four copies. The RRM is a region of around eighty amino acids containing several well conserved residues, some of which cluster into two short submotifs, RNP-1 (octamer) and RNP-2 (hexamer) (Birney et al., Nucleic Acids Research, 1993, Vol. 21, No. 25, 5803-5816).

The *Arabidopsis* genome encodes 196 RRM-containing proteins, an example of which is RBP1 (Lorkovic et al., Nucleic Acids Research, 2002, Vol. 30, No. 3, 623-635). They report that the RRMs of AtRBP1 are most similar to those of the metazoan Musashi proteins. In addition to AtRBP1, Lorkovic et al. describe three proteins having similarity to AtRBP1 and Musashi proteins. RBP1 from *Arabidopsis thaliana* was first isolated by Suzuki et al. (Plant Cell Physiol. 41(3): 282-288 (2000)) and was found to be expressed in rapidly dividing tissue. RBP1, an RNA-binding protein (as shown by Suzuki et al. 2000) comprises two RRMs.

According to one embodiment of the present invention, there is provided a method for improving the growth characteristics of a plant, comprising increasing activity in a plant of an RNA-binding protein or a homologue thereof, which RNA-binding protein or homologue thereof has RNA binding activity and either 2 or 3 RNA recognition motifs (RRMs) and which comprises a motif having at least 75% sequence identity to motif I: PYEAAVVALPVVVKERLVRILRLGIATRYD (SEQ ID NO: 12) and/or a motif having at least 50% sequence identity to motif II: RFDPFTGEPYKFDP (SEQ ID NO: 13).

According to another embodiment of the present invention, there is provided a method for improving the growth characteristics of a plant, comprising increasing activity in a plant of an RBP1 polypeptide or a homologue thereof having the following: (a) RNA-binding activity; (b) two RRM domains, (c) the following two motifs: (i) KIFVGGL (SEQ ID NO: 41); and (ii) RPRGFGF (SEQ ID NO: 42), allowing for up to three amino acid substitutions and any conservative change in the motifs; and (d) having, in increasing order of preference, at least 20%, 25%, 30%, 35%, 40%, 45%, 50%, 55%, 60%, 65%, 70%, 75%, 80%, 85%, 90%, 95% sequence identity to the amino acid represented by SEQ ID NO: 15.

According to another embodiment of the present invention, there is provided a method for improving the growth characteristics of a plant, comprising increasing activity in a plant of an RBP1 polypeptide or a homologue thereof having the following: (a) RNA-binding activity; (b) two RRM domains, (c) the following two motifs: (i) KIFVGGL; and (ii) RPRGFGF, allowing for up to three amino acid substitutions and any conservative change in the motifs; and (d) having, in increasing order of preference, at least 20%, 25%, 30%, 35%, 40%, 45%, 50%, 55%, 60%, 65%, 70%, 75%, 80%, 85%, 90%, 95% sequence identity to the amino acid represented by SEQ ID NO: 15.

Advantageously, performance of the methods according to the present invention result in plants having a variety of improved growth characteristics, especially increased yield, particularly seed yield.

The term "increased yield" as defined herein is taken to mean an increase in any one or more of the following, each relative to corresponding wild type plants: (i) increased biomass (weight) of one or more parts of a plant, particularly aboveground (harvestable) parts, increased root biomass or increased biomass of any other harvestable part; (ii) increased seed yield, which includes an increase in seed biomass (seed weight) and which may be an increase in the seed weight per plant or on an individual seed basis; (iii) increased number of (filled) seeds; (iv) increased seed size, which may also influence the composition of seeds; (v) increased seed volume, which may also influence the composition of seeds; (vi) increased harvest index, which is expressed as a ratio of the yield of harvestable parts, such as seeds, over the total biomass; and (vii) increased thousand kernel weight (TKW), which is extrapolated from the total weight of the number of filled seeds. An increased TKW may result from an increased seed size and/or seed weight.

Taking corn as an example, a yield increase may be manifested as one or more of the following: increase in the number of plants per hectare or acre, an increase in the number of ears per plant, an increase in the number of rows, number of kernels per row, kernel weight, thousand kernel weight, ear length/diameter, among others. Taking rice as an example, a yield increase may be manifested by an increase in one or more of the following: number of plants per hectare or acre, number of panicles per plant, number of spikelets per panicle, number of flowers per panicle, increase in the seed filling rate, increase in thousand kernel weight, among others. An increase in yield may also result in modified architecture, or may occur as a result of modified architecture.

According to a preferred feature, performance of the methods of the invention result in plants having increased yield. Therefore, according to the present invention, there is provided a method for increasing plant yield, which method comprises increasing activity in a plant of an RNA-binding protein or a homologue thereof, which RNA-binding protein or homologue thereof has RNA binding activity and either 2 or 3 RNA recognition motifs (RRMs) and which comprises a motif having at least 75% sequence identity to motif I: PYEAAVVALPVVVKERLVRILRLGIATRYD (SEQ ID NO: 12) and/or a motif having at least 50% sequence identity to motif II: RFDPFTGEPYKFDP (SEQ ID NO: 13). According to another preferred feature of the present invention, there is provided a method for increasing plant yield, which method comprises increasing activity in a plant of an RBP1 polypeptide or a homologue thereof having the following: (a) RNA-binding activity; (b) two RRM domains, (c) the following two motifs: (i) KIFVGGL (SEQ ID NO: 41); and (ii) RPRGFGF (SEQ ID NO: 42), allowing for up to three amino acid substitutions and any conservative change in the motifs; and (d) having, in increasing order of preference, at least 20%, 25%, 30%, 35%, 40%, 45%, 50%, 55%, 60%, 65%, 70%, 75%, 80%, 85%, 90%, 95% sequence identity to the amino acid represented by SEQ ID NO: 15.

Since the transgenic plants according to the present invention have increased yield, it is likely that these plants exhibit an increased growth rate (during at least part of their life cycle), relative to the growth rate of corresponding wild type plants at a corresponding stage in their life cycle. The increased growth rate may be specific to one or more parts of a plant (including seeds), or may be throughout substantially the whole plant. A plant having an increased growth rate may even exhibit early flowering. The increase in growth rate may take place at one or more stages in the life cycle of a plant or during substantially the whole plant life cycle. Increased growth rate during the early stages in the life cycle of a plant may reflect enhanced vigour. The increase in growth rate may alter the harvest cycle of a plant allowing plants to be sown later and/or harvested sooner than would otherwise be possible. If the growth rate is sufficiently increased, it may allow for the sowing of further seeds of the same plant species (for example sowing and harvesting of rice plants followed by sowing and harvesting of further rice plants all within one conventional growing period). Similarly, if the growth rate is sufficiently increased, it may allow for the sowing of further seeds of different plants species (for example the sowing and harvesting of rice plants followed by, for example, the sowing and optional harvesting of soy bean, potato or any other suitable plant). Harvesting additional times from the same rootstock in the case of some plants may also be possible. Altering the harvest cycle of a plant may lead to an increase in annual biomass production per acre (due to an increase in the number of times (say in a year) that any particular plant may be grown and harvested). An increase in growth rate may also allow for the cultivation of transgenic plants in a wider geographical area than their wild-type counterparts, since the territorial limitations for growing a crop are often determined by adverse environmental conditions either at the time of planting (early season) or at the time of harvesting (late season). Such adverse conditions may be avoided if the harvest cycle is shortened. The growth rate may be determined by deriving various parameters from growth curves plotting growth experiments, such parameters may be: T-Mid (the time taken for plants to reach 50% of their maximal size) and T-90 (time taken for plants to reach 90% of their maximal size), amongst others.

Performance of the methods of the invention gives plants having an increased growth rate. Therefore, according to the present invention, there is provided a method for increasing the growth rate of plants, which method comprises increasing activity in a plant of an RNA-binding protein or a homologue thereof, which RNA-binding protein or homologue thereof has RNA binding activity and either 2 or 3 RNA recognition motifs (RRMs) and which comprises a motif having at least 75% sequence identity to motif I: PYEAAVVALPVVVKERLVRILRLGIATRYD (SEQ ID NO: 12) and/or a motif having at least 50% sequence identity to motif II: RFDPFTGEPYKFDP (SEQ ID NO: 13). There is also provided a further method for increasing the growth rate of plants, which method comprises increasing activity in a plant of an RBP1 polypeptide or a homologue thereof having the following: (a) RNA-binding activity; (b) two RRM domains, (c) the following two motifs: (i) KIFVGGL (SEQ ID NO: 41); and (ii) RPRGFGF (SEQ ID NO: 42), allowing for up to three amino acid substitutions and any conservative change in the motifs; and (d) having, in increasing order of preference, at least 20%, 25%, 30%, 35%, 40%, 45%, 50%, 55%, 60%, 65%, 70%, 75%, 80%, 85%, 90%, 95% sequence identity to the amino acid represented by SEQ ID NO: 15.

An increase in yield and/or growth rate occurs whether the plant is under non-stress conditions or whether the plant is exposed to various mild stresses compared to control plants. Plants typically respond to exposure to stress by growing more slowly. In conditions of severe stress, the plant may even stop growing altogether. Mild stress on the other hand is defined herein as being any stress to which a plant is exposed which does not result in the plant ceasing to grow altogether without the capacity to resume growth. Due to advances in agricultural practices (irrigation, fertilization, pesticide treatments) severe stresses are not often encountered in cultivated crop plants. As a consequence, the compromised growth induced by mild stress is often an undesirable feature in agriculture. Mild stresses are the typical stresses to which a plant may be exposed. These stresses may be the everyday biotic and/or abiotic (environmental) stresses to which a plant is exposed. Typical abiotc or environmental stresses include temperature stresses caused by atypical hot or cold/freezing temperatures; salt stress; water stress (drought or excess water). Abiotic stresses may also be caused by chemicals. Biotic stresses are typically those stresses caused by pathogens, such as bacteria, viruses, fungi and insects.

The abovementioned growth characteristics may advantageously be modified in any plant.

The term "plant" as used herein encompasses whole plants, ancestors and progeny of plants and plant parts, including seeds, shoots, stems, leaves, roots, flowers (including tubers), and tissues and organs, wherein each of the aforementioned comprise the gene/nucleic acid of interest. The term "plant" also encompasses suspension cultures, callus tissue, embryos, meristematic regions, gametophytes, sporophytes, pollen, and microspores, again wherein each of the aforementioned comprise the gene/nucleic acid of interest.

Plants that are particularly useful in the methods of the invention include all plants which belong to the superfamily Viridiplantae, in particular monocotyledonous and dicotyledonous plants including fodder or forage legumes, ornamental plants, food crops, trees or shrubs selected from the list comprising *Acacia* spp., *Acer* spp., *Actinidia* spp., *Aesculus* spp., *Agathis australis*, *Albizia amara*, *Alsophila tricolor*, *Andropogon* spp., *Arachis* spp, *Areca catechu*, *Astelia fragrans*, *Astragalus cicer*, *Baikiaea plurijuga*, *Betula* spp., *Brassica* spp., *Bruguiera gymnorrhiza*, *Burkea africana*, *Butea frondosa*, *Cadaba farinosa*, *Calliandra* spp, *Camellia sinensis*, *Canna indica*, *Capsicum* spp., *Cassia* spp., *Centroema pubescens*, *Chaenomeles* spp., *Cinnamomum cassia*, *Coffea arabica*, *Colophospermum mopane*, *Coronillia varia*, *Cotoneaster serotina*, *Crataegus* spp., *Cucumis* spp., *Cupressus* spp., *Cyathea dealbata*, *Cydonia oblonga*, *Cryptomeria japonica*, *Cymbopogon* spp., *Cynthea dealbata*, *Cydonia oblonga*, *Dalbergia monetaria*, *Davallia divaricata*, *Desmodium* spp., *Dicksonia squarosa*, *Diheteropogon amplectens*, *Dioclea* spp, *Dolichos* spp., *Dorycnium rectum*, *Echinochloa pyramidalis*, *Ehrartia* spp., *Eleusine coracana*, *Eragrestis* spp., *Erythrina* spp., *Eucalyptus* spp., *Euclea schimperi*, *Eulalia villosa*, *Fagopyrum* spp., *Feijoa sellowiana*, *Fragaria* spp., *Flemingia* spp, *Freycinetia banksii*, *Geranium thunbergii*, *Ginkgo biloba*, *Glycine javanica*, *Gliricidia* spp, *Gossypium hirsutum*, *Grevillea* spp., *Guibourtia coleosperma*, *Hedysarum* spp., *Hemarthia altissima*, *Heteropogon contortus*, *Hordeum vulgare*, *Hyparrhenia rufa*, *Hypericum erectum*, *Hyperthelia dissoluta*, *Indigo incamata*, *Iris* spp., *Leptarrhena pyrolifolia*, *Lespediza* spp., *Lettuca* spp., *Leucaena leucocephala*, *Loudetia simplex*, *Lotonus bainesii*, *Lotus* spp., *Macrotyloma axillare*, *Malus* spp., *Manihot esculenta*, *Medicago sativa*, *Metasequoia glyptostroboides*, *Musa sapientum*, *Nicotianum* spp., *Onobrychis* spp., *Ornithopus* spp., *Oryza* spp., *Peltophorum africanum*, *Pennisetum* spp., *Persea gratissima*, *Petunia* spp., *Phaseolus* spp., *Phoenix canariensis*, *Phormium cookianum*, *Photinia* spp., *Picea glauca*, *Pinus* spp., *Pisum sativum*, *Podocarpus totara*, *Pogonarthria fleckii*, *Pogonarthria squarrosa*, *Populus* spp., *Prosopis cineraria*, *Pseudotsuga menziesii*, *Pterolobium stellatum*, *Pyrus communis*, *Quercus* spp., *Rhaphiolepsis umbellata*, *Rhopalostylis sapida*, *Rhus natalensis*, *Ribes grossularia*, *Ribes* spp., *Robinia pseudoacacia*, *Rosa* spp., *Rubus* spp., *Salix* spp., *Schyzachyrium sanguineum*, *Sciadopitys verticillata*, *Sequoia sempervirens*, *Sequoiadendron giganteum*, *Sorghum bicolor*, *Spinacia* spp., *Sporobolus fimbriatus*, *Stiburus alopecuroides*, *Stylosanthos humilis*, *Tadehagi* spp, *Taxodium distichum*, *Themeda triandra*, *Trifolium* spp., *Triticum* spp., *Tsuga heterophylla*, *Vaccinium* spp., *Vicia* spp., *Vitis vinifera*, *Watsonia pyramidata*, *Zantedeschia aethiopica*, *Zea mays*, amaranth, artichoke, asparagus, broccoli, Brussels sprouts, cabbage, canola, carrot, cauliflower, celery, collard greens, flax, kale, lentil, oilseed rape, okra, onion, potato, rice, soybean, strawberry, sugar beet, sugarcane, sunflower, tomato, squash, tea and algae, amongst others. According to a preferred embodiment of the present invention, the plant is a crop plant such as soybean, sunflower, canola, alfalfa, rapeseed, cotton, tomato, potato or tobacco. Further preferably, the plant is a monocotyledonous plant, such as sugar cane. More preferably the plant is a cereal, such as rice, maize, wheat, barley, millet, rye, sorghum or oats.

The activity of an RNA-binding protein, or of a homologue thereof, may be increased by increasing levels of the RNA-binding protein. Alternatively, activity may also be increased without increase in levels of an RNA-binding protein, or even when there is a reduction in levels of an RNA-binding protein. This may occur when the intrinsic properties of the polypeptide are altered, for example, by making a mutant form that is more active that the wild type. Similarly, the activity of an RBP1 polypeptide or homologue thereof may be increased by increasing levels of the RBP1 polypeptide protein. Alternatively, activity may also be increased when there is no change in levels of an RBP1, or even when there is a reduction in levels of an RBP1 polypeptide. This may occur when the intrinsic properties of the polypeptide are altered, for example, by making mutant that is more active that the wild type.

The term "RNA-binding protein or homologue thereof" as defined herein refers to a polypeptide with RNA binding activity and having either 2 or 3 RNA recognition motifs (RRMs) and which comprises a motif having at least 75%, 80%, 85%, 90% or 95% sequence identity to motif I: PYEAAVVALPVVVKERLVRILRLGIATRYD (SEQ ID NO: 12) and/or a motif having at least 50%, 55%, 60%, 65%, 70%, 75%, 80%, 85%, 90% or 95% sequence identity to motif II: RFDPFTGEPYKFDP (SEQ ID NO: 13). The term also refers to an amino acid sequence having in increasing order of preference at least 13%, 15%, 17%, 19%, 21%, 23%, 25%, 30%, 35%, 40%, 45%, 50%, 55%, 60%, 65%, 70%, 75%, 80%, 85%, 90% or 95% sequence identity to the amino acid sequence represented by SEQ ID NO: 2.

An "RNA-binding protein or a homologue thereof" falling within the above definition may readily be identified using routine techniques well known to persons skilled in the art. For example, RNA-binding activity may readily be determined in vitro or in vivo using techniques well known in the art. Examples of in vitro assays include: nucleic acid binding assays using North-Western and/or South-Western analysis (Suzuki et al. Plant Cell Physiol. 41(3): 282-288 (2000)); RNA binding assays using UV cross linking; Electrophoretic Mobility Shift Assay for RNA Binding Proteins (Smith, RNA-Protein Interactions—A Practical Approach 1998, University of Cambridge). Examples of in vivo assays include: TRAP (translational repression assay procedure) (Paraskeva E, Atzberger A, Hentze M W: A translational repression assay procedure (TRAP) for RNA-protein interactions in vivo. PNAS Feb. 3, 1998; 95(3): 951-6).

Whether a polypeptide has at least 13% identity to the amino acid represented by SEQ ID NO: 2 may readily be established by sequence alignment. Methods for the alignment of sequences for comparison are well known in the art, such methods include GAP, BESTFIT, BLAST, FASTA and TFASTA. GAP uses the algorithm of Needleman and Wunsch (J. Mol. Biol. 48: 443-453, 1970) to find the alignment of two complete sequences that maximises the number of matches and minimises the number of gaps. The BLAST algorithm calculates percent sequence identity and performs a statistical analysis of the similarity between the two sequences. The software for performing BLAST analysis is publicly available through the National Centre for Biotechnology Information. An RNA-binding protein or a homologue thereof having at least 13% identity to the amino acid represented by SEQ ID NO: 2 may readily be identified by aligning a query sequence (preferably a protein sequence) with known RNA-binding protein sequences (see for example the alignment shown in FIG. 1) using, for example, the VNTI AlignX multiple alignment program, based on a modified clustal W algorithm (InforMax, Bethesda, MD, informaxinc.com), with default settings for gap opening penalty of 10 and a gap extension of 0.05.

A person skilled in the art will also readily be able to identify motifs having at least 75%, 80%, 85%, 90% or 95% sequence identity to motif I: PYEAAVVALPVVVKERLVRILRLGIATRYD (SEQ ID NO: 12) and/or motifs having at least 50%, 55%, 60%, 65%, 70%, 75%, 80%, 85% or 90% sequence identity to motif II: RFDPFTGEPYKFDP (SEQ ID NO: 13). This may easily be achieved by making an alignment and searching for homologous regions.

Table 1 below shows motif I and 11 as found in the sequence of SEQ ID NO: 2 and the percentage sequence identity with corresponding motifs in homologous RNA-binding proteins. RNA-binding proteins useful in the methods of the invention may contain motif I or II, or motifs I and II.

TABLE 1

Motifs found in RNA binding proteins and homologues thereof

| | Gene name and Accession number | Conserved Motif | % Sequence identity with the motifs SEQ ID NO: 2 |
|---|---|---|---|
| Motif I | Tobacco CDS701 (SEQ ID NO: 2) | PYEAAVVALPVVVKERLVRILRLGIATRYD | |
| | Rice CDS701 homologue (AL731884) SEQ ID NO: 4 | PYEAAVVSLPSAVKELLLRILRLRIGTRYD | Identity: 23/30 (76.7%) # Similarity: 25/30 (83.3%) |
| | Rice predicted fragment AK059444 SEQ ID NO: 6 | PYEAAVVSLPSAVKELLLRILRLRIGTRYD | Identity: 23/30 (76.7%) # Similarity: 25/30 (83.3%) |
| | Corn predicted fragment AY105295 SEQ ID NO: 8 | PYESAVNSLPSAVKEVLLRILRLRIGTRYD | Identity: 21/30 (70.0%) # Similarity: 24/30 (80.0%) |
| | Consensus Motif I | PYE A/S AV V/N A/S LP V/S V/A VKE L/R/V L V/L RILRL G/R I A/G TRYD | 30,9 substitutions |
| Motif II | Tobacco CDS701 (SEQ ID NO: 2) | RFDPFTGEPYKFDP | |
| | Rice CDS701 homologue | RFDPFTGEPYKFDP | Identity: 14/14 (100.0%) |

TABLE 1-continued

Motifs found in RNA binding proteins and homologues thereof

| Gene name and Accession number | Conserved Motif | % Sequence identity with the motifs SEQ ID NO: 2 |
|---|---|---|
| (AL731884) SEQ ID NO: 4 | | # Similarity: 14/14 (100.0%) |
| Rice predicted fragment AK059444 SEQ ID NO: 6 | RFDPFTGEPYKFDP | Identity: 14/14 (100.0%) # Similarity: 14/14 (100.0%) |
| Corn predicted fragment AY105295 SEQ ID NO: 8 | RFDPFTGEPYKFXP | Identity: 13/14 (92.9%) # Similarity: 13/14 (92.9%) |
| Rice BAC83046 SEQ ID NO: 10 | RYPPHLGEAIKFSP | Identity: 7/14 (50.0%) # Similarity: 8/14 (57.1%) |
| Consensus M2 | R F/Y D/P P F/H T/L GE P/A Y/I KF D/X/S | 14,7 substitutions |

Examples of polypeptides falling under the definition of an "RNA-binding protein or a homologue thereof" include the following sequences: SEQ ID NO: 2 from tobacco; SEQ ID NO: 4 is a protein prediction of a BAC clone from rice (NCBI Accession number AL731884); SEQ ID NO: 6 is a rice protein prediction (fragment) from cDNA (NCBI Accession number AK059444); SEQ ID NO: 8 is a corn protein prediction (fragment) from CDNA (NCBI Accession number AY105295); and SEQ ID NO: 10 is a full length rice sequence (NCBI Accession number BAC83046).

It is to be understood that the term RNA-binding protein or a homologue thereof is not to be limited to the sequences represented by SEQ ID NO: 2, SEQ ID NO: 4, SEQ ID NO: 6, SEQ ID NO: 8 and SEQ ID NO: 10, but that any polypeptide meeting the criteria of having RNAbinding activity and having either 2 or 3 RNA recognition motifs (RRMs) and which comprises a motif having at least 75% sequence identity to motif I: PYEAAVVALPVVVKERLVRILRLGIA-TRYD (SEQ ID NO: 12) and/or a motif having at least 50% sequence identity to motif II: RFDPFTGEPYKFDP (SEQ ID NO: 13) may also be useful in performing the methods of the invention.

The term "RBP1 or homologue thereof" as defined herein refers to a polypeptide having the following: (a) RNA-binding activity; (b) two RRM domains, (c) the following two motifs: (i) KIFVGGL (SEQ ID NO: 41); and (ii) RPRGFGF (SEQ ID NO: 42), allowing for up to three amino acid substitutions and any conservative change in the motifs; and (d) having, in increasing order of preference, at least 20%, 25%, 30%, 35%, 40%, 45%, 50%, 55%, 60%, 65%, 70%, 75%, 80%, 85%, 90%, 95% sequence identity to the amino acid represented by SEQ ID NO: 15. Conservative substitution tables are well known in the art (see for example Creighton (1984) Proteins. W.H. Freeman and Company and see Table 4 below).

An "RBP1 polypeptide or a homologue thereof" falling within the above definition may readily be identified using routine techniques well known to persons skilled in the art. For example, RNA-binding activity may readily be determined as described above.

Furthermore, RRM domains are well known in the art and consist of around 80-90 amino acids; they have a structure consisting of four strands and two helices arranged in an alpha/beta sandwich, with a third helix sometimes being present during RNA binding. RRM domain-containing proteins have a modular structure. RRM domains may be identified using SMART (a Simple Modular Architecture Research Tool: Identification of signaling domains, Schultz et al. PNAS, 95, 5857-5864 (1998)) smart.embl-heidelberg.de/). See also Letunic et al., Recent improvements to the SMART domain-based sequence annotation resource (Nucleic Acids Res. 30(1), 242-244).

Whether a polypeptide has at least 20% identity to the amino acid represented by SEQ ID NO: 2 may readily be established by sequence alignment using the methods for alignment as described above.

Since RBP1 polypeptides comprise highly conserved regions, a person skilled in the art would readily be able to identify other RBP1 sequences by comparing any conserved regions of the query sequence against those of the known RBP1 sequences. Examples of these conserved regions include the following two motifs: (i) KIFVGGL (SEQ ID NO: 41); and (ii) RPRGFGF (SEQ ID NO: 42), allowing for up to three amino acid substitutions and any conservative change in the motifs.

Examples of polypeptides falling under the definition of an "RBP1 or a homologue thereof" include: At1g58470 (SEQ ID NO: 15), At4g26650 (SEQ ID NO: 17), At5g55550 (SEQ ID NO: 19), At4g14300 (SEQ ID NO: 21), At3g07810 (SEQ ID NO: 23), At2g33410 (SEQ ID NO: 25) and At5g47620 (SEQ ID NO: 27) all from *Arabidopsis thaliana*; NP_921939.1 (SEQ ID NO: 29) from rice; AK067725 (SEQ ID NO: 31) and AK070544 (SEQ ID NO: 33) which correspond to rice mRNAs encoding RBP1 polypeptides; CK210974 (SEQ ID NO: 35) from wheat and CA124210 (SEQ ID NO: 37) from sugarcane are partial protein predictions from ESTs (expressed sequence tags).

Despite what may appear to be a relatively low sequence homology (as low as approximately 25%), RPB1 proteins are highly conserved in structure with all full-length proteins having 2 RRM domains. rbp1 genes in other plant species may therefore easily be found (see the above examples from rice, sugarcane and wheat which have herein been identified for the first time as RBP1 proteins). Table 2 below shows the percentage identities for some of the sequences shown in the alignment of FIG. 3.

TABLE 2

Homology of RBP1 protein sequences with SEQ ID NO: 2 based on overall global sequence alignment

| MIPs Accession Number Identifier (mips.gsf.de/) | SEQ ID NO | RRM domains | Global homology VNTI align program (informax) |
|---|---|---|---|
| At4g26650 | SEQ ID NO: 17 | 2X RRM | 28.4% |
| At5g55550 | SEQ ID NO: 19 | 2X RRM | 28.9% |
| At4g14300 | SEQ ID NO: 21 | 2X RRM | 31.9% |
| At3g07810 | SEQ ID NO: 23 | 2X RRM | 24.9% |
| At2g33410 | SEQ ID NO: 25 | 2X RRM | 29.2% |
| At5g47620 | SEQ ID NO: 27 | 2X RRM | 26.7% |
| | | 2X RRM | |
| AK070544-Os (DNA sequence corresponding to mRNA). Chromosomic location: BAC AC125782.2 (138541-142744) | SEQ ID NO: 33 | 2X RRM | 26.8% |
| AK067725-OS (DNA sequence corresponding to mRNA). Chromosomic location: BAC AP003747 (103016-107790) | SEQ ID NO: 31 | 2X RRM | 26.3% |

It is to be understood that the term RBP1 polypeptide or a homologue thereof is not to be limited to the sequences represented by SEQ ID NO: 15, SEQ ID NO: 17, SEQ ID NO: 19, SEQ ID NO: 21, SEQ ID NO: 23, SEQ ID NO: 25 or SEQ ID NO: 27, SEQ ID NO: 29, SEQ ID NO: 31, SEQ ID NO: 33, SEQ ID NO: 35 and SEQ ID NO: 37, but that any polypeptide meeting the criteria of having: (a) RNA-binding activity; (b) two RRM domains, (c) the following two motifs: (i) KIFVGGL (SEQ ID NO: 41); and (ii) RPRGFGF (SEQ ID NO: 42), allowing for up to three amino acid substitutions and any conservative change in the motifs; and (d) having, in increasing order of preference, at least 20%, 25%, 30%, 35%, 40%, 45%, 50%, 55%, 60%, 65%, 70%, 75%, 80%, 85%, 90%, 95% sequence identity to the amino acid represented by SEQ ID NO: 15 may be useful in performing the methods of the invention.

A nucleic acid encoding an RNA-binding protein or a homologue thereof may be any natural or synthetic nucleic acid. An RNA-binding protein or a homologue thereof as defined hereinabove is encoded by an RNA-binding protein-encoding nucleic acid/gene. Therefore the term "RNA-binding protein-encoding nucleic acid/gene" as defined herein is any nucleic acid/gene encoding an RNA-binding protein or a homologue thereof, as defined hereinabove. Examples of RNA-binding protein-encoding nucleic acids include those represented by any one of SEQ ID NO: 1, SEQ ID NO: 3, SEQ ID NO: 5, SEQ ID NO: 7 and SEQ ID NO: 9. RNA-binding protein-encoding nucleic acids/genes and functional variants thereof may be suitable in practising the methods of the invention. Functional variant RNA-binding protein-encoding nucleic acid/genes include portions of an RNA-binding protein-encoding nucleic acid/gene and/or nucleic acids capable of hybridising with an RNA-binding protein-encoding nucleic acid/gene. The term "functional" in the context of a functional variant refers to a variant (i.e. a portion or a hybridising sequence) which encodes a polypeptide having RNA-binding activity and preferably and additionally at least one RRM, preferably either 2 or 3 RRMs and further preferably at least one of the following motifs: a motif having at least 75% sequence identity to motif I: PYEAAVVALPVVVKER-LVRILRLGIATRYD (SEQ ID NO: 12) and/or a motif having at least 50% sequence identity to motif II: RFDPFTGEPYK-FDP (SEQ ID NO: 13). The term "functional may also refer to a nucleic acid encoding an RNA-binding protein or homologue thereof, as defined hereinabove, which when introduced and expressed in a plant gives plants having improved growth characteristics.

The nucleic acid encoding an RBP1 polypeptide or a homologue thereof may be any natural or synthetic nucleic acid. An RBP1 polypeptide or a homologue thereof as defined hereinabove is encoded by an rbp1 nucleic acid/gene. Therefore the term "rbp1 nucleic acid/gene" as defined herein is any nucleic acid/gene encoding an RBP1 polypeptide or a homologue thereof as defined hereinabove. Examples of rbp 1 nucleic acids include those represented by any one of SEQ ID NO: 14, SEQ ID NO: 16, SEQ ID NO: 18, SEQ ID NO: 20, SEQ ID NO: 22, SEQ ID NO: 24, SEQ ID NO: 26, SEQ ID NO: 28, SEQ ID NO: 30, SEQ ID NO: 32, SEQ ID NO: 34 and SEQ ID NO: 36. rbp1 nucleic acids/genes and functional variants thereof may be suitable in practising the methods of the invention. Functional variant rbp1 nucleic acid/genes include portions of an rbp1 nucleic acid/gene and/or nucleic acids capable of hybridising with an rbp1 nucleic acid/gene. The term "functional" in the context of a functional variant refers to a variant (i.e. a portion or a hybridising sequence) which encodes a polypeptide having RNA-binding activity and at least one RRM domain, preferably two RRM domains and further preferably the following two motifs: (i) KIFVGGL (SEQ ID NO: 41) and (ii) RPRGFGF (SEQ ID NO: 42), allowing for up to three amino acid substitutions and any conservative change in the motifs. The term "functional may also refer to a nucleic acid encoding an RBP1 polypeptide or homologue thereof, as defined hereinabove, which when introduced and expressed in a plant gives plants having improved growth characteristics.

The term portion as defined herein refers to an RNA binding protein-encoding piece of DNA of, in increasing order of preference, at least 180, 300, 500 or 700 nucleotides in length and which portion encodes a polypeptide having RNA binding activity and at least 1 RRM, preferably two or three RRMs and at least one, preferably both, of motifs I or II. A portion may be prepared, for example, by making one or more deletions to an RNA-binding protein-encoding nucleic acid. The portions may be used in isolated form or they may be fused to other coding (or non coding) sequences in order to, for example, produce a protein that combines several activities, one of them being RNA binding activity. When fused to other coding sequences, the resulting polypeptide produced upon translation may be larger than that predicted for the RNA-binding protein portion. Preferably, the functional portion is a portion of a nucleic acid as represented by any one of SEQ ID NO: 1, SEQ ID NO: 3, SEQ ID NO: 5, SEQ ID NO: 7 and SEQ ID NO: 9.

The term portion with reference to an rbpl nucleic acid refers to a piece of DNA comprising at least 80 nucleotides and which portion encodes a polypeptide having RNA binding activity and having at least one RRM domain, preferably two RRM domains and further preferably the following two motifs: (i) KIFVGGL (SEQ ID NO: 41) and (ii) RPRGFGF (SEQ ID NO: 42). A portion may be prepared, for example, by making one or more deletions to an rbpl nucleic acid. The portions may be used in isolated form or they may be fused to other coding (or non coding) sequences in order to, for example, produce a protein that combines several activities, one of them being RNA binding activity. When fused to other coding sequences, the resulting polypeptide produced upon translation could be bigger than that predicted for the rbp1 fragment. Preferably, the functional portion is a portion of a nucleic acid as represented by any one of SEQ ID NO: 14, SEQ ID NO: 16, SEQ ID NO: 18, SEQ ID NO: 20, SEQ ID NO: 22 SEQ ID NO: 24, SEQ ID NO: 26, SEQ ID NO: 28, SEQ ID NO: 30, SEQ ID NO: 32, SEQ ID NO: 34 and SEQ ID NO: 36.

Another type of variant RNA-binding protein is a nucleic acid capable of hybridising under reduced stringency conditions, preferably under stringent conditions, with an RNA-binding protein-encoding nucleic acid/gene as hereinbefore defined, which hybridising sequence encodes a polypeptide having RNA binding activity and having at least 1 RRM, preferably two or three RRMs, and at least one, preferably two, of motifs I or II. The hybridising sequence is, in increasing order of preference, at least 180, 300, 500 or 700 nucleotides in length. Preferably, the hybridising sequence is capable of hybridising to a nucleic acid as represented by any one of SEQ ID NO: 1, SEQ ID NO: 3, SEQ ID NO: 5, SEQ ID NO: 7 and SEQ ID NO: 9.

Similarly, another type of variant rbpl is a nucleic acid capable of hybridising under reduced stringency conditions, preferably under stringent conditions, with an rbpl nucleic acid/gene as hereinbefore defined, which hybridising sequence encodes a polypeptide having RNA binding activity and at least one RRM domain, preferably two RRM domains and further preferably the following two motifs: (i) KIFVGGL (SEQ ID NO: 41) and (ii) RPRGFGF (SEQ ID NO: 42). The hybridising sequence is preferably at least 80 nucleotides in length. Preferably, the hybridising sequence is capable of hybridising to a nucleic acid as represented by any one of SEQ ID NO: 14, SEQ ID NO: 16, SEQ ID NO: 18, SEQ ID NO: 20, SEQ ID NO: 22, SEQ ID NO: 24, SEQ ID NO: 26, SEQ ID NO: 28, SEQ ID NO: 30, SEQ ID NO: 32, SEQ ID NO: 34 and SEQ ID NO: 36.

The term "hybridisation" as defined herein is a process wherein substantially homologous complementary nucleotide sequences anneal to each other. The hybridisation process can occur entirely in solution, i.e. where both complementary nucleic acids are in solution. The hybridisation process can also occur with one of the complementary nucleic acids immobilised to a matrix such as magnetic beads, Sepharose beads or any other resin. The hybridisation process can furthermore occur with one of the complementary nucleic acids immobilised to a solid support such as a nitro-cellulose or nylon membrane or immobilised by e.g. photolithography to, for example, a siliceous glass support (the latter known as nucleic acid arrays or microarrays or as nucleic acid chips). In order to allow hybridisation to occur, the nucleic acid molecules are generally thermally or chemically denatured to melt a double strand into two single strands and/or to remove hairpins or other secondary structures from single stranded nucleic acids. The stringency of hybridisation is influenced by conditions such as temperature, salt concentration, ionic strength and hybridisation buffer composition. Hybridisation occurs under reduced stringency conditions, preferably under stringent conditions. Examples of stringency conditions are shown in Table 3 below. Stringent conditions are those that are at least as stringent as, for example, conditions A-L; and reduced stringency conditions are at least as stringent as, for example, conditions M-R.

TABLE 3

Examples of stringency conditions

| Stringency Condition | Polynucleotide Hybrid± | Hybrid Length (bp)‡ | Hybridization Temperature and Buffer† | Wash Temperature and Buffer† |
|---|---|---|---|---|
| A | DNA:DNA | > or equal to 50 | 65° C.; 1 ×SSC-or −42° C.; 1 ×SSC, 50% formamide | 65° C.; 0.3 ×SSC |
| B | DNA:DNA | <50 | Tb*; 1 ×SSC | Tb*; 1 ×SSC |
| C | DNA:RNA | > or equal to 50 | 67° C.; 1 ×SSC-or −45° C.; 1 ×SSC, 50% formamide | 67° C.; 0.3 ×SSC |
| D | DNA:RNA | <50 | Td*; 1 ×SSC | Td*; 1 ×SSC |
| E | RNA:RNA | > or equal to 50 | 70° C.; 1 ×SSC-or −50° C.; 1 ×SSC, 50% formamide | 70° C.; 0.3 ×SSC |
| F | RNA:RNA | <50 | Tf*; 1 ×SSC | Tf*; 1 ×SSC |
| G | DNA:DNA | > or equal to 50 | 65° C.; 4 ×SSC-or −45° C.; 4 ×SSC, 50% formamide | 65° C.; 1 ×SSC |

TABLE 3-continued

Examples of stringency conditions

| Stringency Condition | Polynucleotide Hybrid± | Hybrid Length (bp)‡ | Hybridization Temperature and Buffer† | Wash Temperature and Buffer† |
|---|---|---|---|---|
| H | DNA:DNA | <50 | Th*; 4° SSC | Th*; 4 ×SSC |
| I | DNA:RNA | > or equal to 50 | 67° C.; 4 ×SSC- or −45° C.; 4 ×SSC, 50% formamide | 67° C.; 1 ×SSC |
| J | DNA:RNA | <50 | Tj*; 4 ×SSC | Tj*; 4 ×SSC |
| K | RNA:RNA | > or equal to 50 | 70° C.; 4 ×SSC- or −40° C.; 6 ×SSC, 50% formamide | 67° C.; 1 ×SSC |
| L | RNA:RNA | <50 | Tl*; 2 ×SSC | Tl*; 2 ×SSC |
| M | DNA:DNA | > or equal to 50 | 50° C.; 4 ×SSC- or −40° C.; 6 ×SSC, 50% formamide | 50° C.; 2 ×SSC |
| N | DNA:DNA | <50 | Tn*; 6 ×SSC | Tn*; 6 ×SSC |
| O | DNA:RNA | > or equal to 50 | 55° C.; 4 ×SSC- or −42° C.; 6 ×SSC, 50% formamide | 55 ×C.; 2 ×SSC |
| P | DNA:RNA | <50 | Tp*; 6 ×SSC | Tp*; 6 ×SSC |
| Q | RNA:RNA | > or equal to 50 | 60° C.; 4 ×SSC- or −45° C.; 6 ×SSC, 50% formamide | 60° C.; 2 ×SSC |
| R | RNA:RNA | <50 | Tr*; 4 ×SSC | Tr*; 4 ×SSC |

‡The "hybrid length" is the anticipated length for the hybridising nucleic acid. When nucleic acids of known sequence are hybridised, the hybrid length may be determined by aligning the sequences and identifying the conserved regions described herein.
†SSPE (1 ×SSPE is 0.15 M NaCl, 10 mM NaH2PO4, and 1.25 mM EDTA, pH 7.4) may be substituted for SSC (1 ×SSC is 0.15 M NaCl anmd 15 mM sodium citrate) in the hybridisation and wash buffers; washes are performed for 15 minutes after hybridisation is complete. The hybridisations and washes may additionally include 5 × Denhardt's reagent, .5-1.0% SDS, 100 ug/ml denatured, fragmented salmon # sperm DNA, 0.5% sodium pyrophosphate, and up to 50% formamide.
*Tb-Tr: The hybridization temperature for hybrids anticipated to be less than 50 base pairs in length should be 5-10° C. less than the melting temperature Tm of the hybrids there Tm is determined according to the following equations. For hybrids less than 18 base pairs in length, Tm (° C.) = 2 (# of A + T bases) + 4 (# of G + C bases). For hybrids between 18 # and 49 base pairs in length, Tm (° C.) = 81.5 + 16.6 (log.sub.10[Na+]) + 0.41 (% G + C) − (600/N), where N is the number of bases in the hybrid, and [Na+] is the concentration of sodium ions in the hybridization buffer ([NA+] for 1 ×SSC = .165 M).
±The present invention encompasses the substitution of any one or more DNA or RNA hybrid partners with either a peptide nucleic acid (PNA) or a modified nucleic acid.

The RNA-binding protein-encoding nucleic acid or variant thereof may be derived from any natural or artificial source. The nucleic acid/gene or variant thereof may be isolated from a microbial source, such as bacteria, yeast or fungi, or from a plant, algae or animal (including human) source. This nucleic acid may be modified from its native form in composition and/or genomic environment through deliberate human manipulation. The nucleic acid is preferably of plant origin, whether from the same plant species (for example to the one in which it is to be introduced) or whether from a different plant species. The nucleic acid may be isolated from a dicotyledonous species, preferably from the family Nicotianae, further preferably from tobacco. More preferably, the RNA-binding protein-encoding nucleic acid isolated from tobacco is represented by SEQ ID NO: 1 and the RNA-binding protein amino acid sequence is as represented by SEQ ID NO: 2.

The rbp1 nucleic acid or variant thereof may be derived from any natural or artificial source. The nucleic acid/gene or variant thereof may be isolated from a microbial source, such as bacteria, yeast or fungi, or from a plant, algae or animal (including human) source. This nucleic acid may be modified from its native form in composition and/or genomic environment through deliberate human manipulation. The nucleic acid is preferably of plant origin, whether from the same plant species (for example to the one in which it is to be introduced) or whether from a different plant species. The nucleic acid may be isolated from a dicotyledonous species, preferably from the family Brassicaceae, further preferably from *Arabidopsis thaliana*. More preferably, the rbp1 isolated from *Arabidopsis thaliana* is represented by SEQ ID NO: 14 and the RBP1 amino acid sequence is as represented by SEQ ID NO: 15.

The activity of an RNA-binding protein or a homologue thereof may be increased by introducing a genetic modification (preferably in the locus of an RNA-binding protein-encoding gene). Similarly, the activity of an RBP1 polypeptide or a homologue thereof may be increased by introducing a genetic modification (preferably in the locus of an rbp1 gene). The locus of a gene as defined herein is taken to mean a genomic region which includes the gene of interest and 10KB up- or downstream of the coding region.

The genetic modification may be introduced, for example, by any one (or more) of the following methods: TDNA activation, TILLING, site-directed mutagenesis, homologous recombination or by introducing and expressing in a plant a nucleic acid encoding an RNA-binding protein or a homologue thereof or by introducing and expressing in a plant a nucleic acid encoding an RBP1 polypeptide or a homologue thereof. Following introduction of the genetic modification there follows a step of selecting for increased activity of an RNA-binding protein or selecting for increased activity of an RBP1 polypeptide, which increase in activity gives plants having improved growth characteristics.

T-DNA activation tagging (Hayashi et al. Science (1992) 1350-1353) involves insertion of T-DNA usually containing a promoter (may also be a translation enhancer or an intron), in the genomic region of the gene of interest or 10KB up- or down stream of the coding region of a gene in a configuration such that the promoter directs expression of the targeted gene. Typically, regulation of expression of the targeted gene by its natural promoter is disrupted and the gene falls under the control of the newly introduced promoter. The promoter is typically embedded in a T-DNA. This T-DNA is randomly inserted into the plant genome, for example, through *Agrobacterium* infection and leads to overexpression of genes near to the inserted T-DNA. The resulting transgenic plants show dominant phenotypes due to overexpression of genes close to the introduced promoter. The promoter to be introduced may be any promoter capable of directing expression of a gene in the desired organism, in this case a plant. For example, constitutive, tissue-preferred, cell type-preferred and inducible promoters are all suitable for use in T-DNA activation.

A genetic modification may also be introduced in the locus of an RNA-binding protein-encoding gene using the technique of TILLING (Targeted Induced Local Lesions IN Genomes). This is a mutagenesis technology useful to generate and/or identify, and to eventually isolate mutagenised variants of an RNA-binding protein-encoding nucleic acid (or rbp1-encoding nucleic acid) having RNA-binding protein activity. TILLING also allows selection of plants carrying such mutant variants. These mutant variants may even exhibit higher RNA-binding protein activity than that exhibited by the gene in its natural form. TILLING combines high-density mutagenesis with high-throughput screening methods. The steps typically followed in TILLING are: (a) EMS mutagenesis (Redei and Koncz, 1992; Feldmann et al., 1994; Lightner and Caspar, 1998); (b) DNA preparation and pooling of individuals; (c) PCR amplification of a region of interest; (d) denaturation and annealing to allow formation of heteroduplexes; (e) DHPLC, where the presence of a heteroduplex in a pool is detected as an extra peak in the chromatogram; (f) identification of the mutant individual; and (g) sequencing of the mutant PCR product. Methods for TILLING are well known in the art (McCallum Nat Biotechnol. April 2000; 18(4):455-7, reviewed by Stemple 2004 (TILLING-a high-throughput harvest for functional genomics. Nat Rev Genet. February 2004;5(2):145-50.)).

Site directed mutagenesis may be used to generate variants of RNA-binding protein-encoding nucleic acids or portions thereof that retain activity, namely, RNA binding activity. Several methods are available to achieve site directed mutagenesis, the most common being PCR based methods (Current Protocols in Molecular Biology. Wiley Eds. ). Site directed mutagenesis may be used to generate variants of RNA-binding protein-encoding nucleic acids or portions thereof that retain activity, namely, RNA binding activity. Similarly, site directed mutagenesis may be used to generate variants of RBP 1-encoding nucleic acids or portions thereof that retain activity, namely, RNA binding activity. Site directed mutagenesis may also be used to generate variants of RBP1-encoding nucleic acids or portions thereof that retain activity, namely, RNA binding activity.

TDNA activation, TILLING and site-directed mutagenesis are examples of technologies that enable the generation of novel alleles and RNA-binding protein variants that retain RNA-binding protein function or that enable the generation novel alleles and rbp1 variants that retain RBP1 function and which are therefore useful in the methods of the invention.

Homologous recombination allows introduction in a genome of a selected nucleic acid at a defined selected position. Homologous recombination is a standard technology used routinely in biological sciences for lower organisms such as yeast or moss (e.g. physcomitrella). Methods for performing homologous recombination in plants have been described not only for model plants (Offringa et al. Extrachromosomal homologous recombination and gene targeting in plant cells after *Agrobacterium*-mediated transformation. 1990 EMBO J. October 1990; 9(10):3077-84) but also for crop plants, for example rice (Terada R, Urawa H, Inagaki Y, Tsugane K, Iida S. Efficient gene targeting by homologous recombination in rice. Nat Biotechnol. 2002. Iida and Terada: A tale of two integrations, transgene and T-DNA: gene targeting by homologous recombination in rice. Curr Opin Biotechnol. April 2004; 15(2):132-3). The nucleic acid to be targeted (which may be an RNA-binding protein-encoding nucleic acid or variant thereof as hereinbefore defined or which may be an rbp1 nucleic acid or variant thereof as hereinbefore defined) need not be targeted to the locus of an RNA-binding protein gene or targeted to the locus of an rbp1 gene, but may be introduced in, for example, regions of high expression. The nucleic acid to be targeted may be an improved allele used to replace the endogenous gene or may be introduced in addition to the endogenous gene.

According to a preferred embodiment of the invention, plant growth characteristics may be improved by introducing and expressing in a plant a nucleic acid encoding an RNA-binding polypeptide or a homologue thereof, which has RNA binding activity and either 2 or 3 RNA recognition motifs (RRMs) and which comprises a motif having at least 75% sequence identity to motif I: PYEAAVVALPVVVKER-LVRILRLGIATRYD (SEQ ID NO: 12) and/or a motif having at least 50% sequence identity to motif II: RFDPFTGEPYK-FDP (SEQ ID NO: 13).

A preferred method for introducing a genetic modification (which in this case need not be in the locus of an RNA-binding protein gene) is to introduce and express in a plant a nucleic acid encoding an RNA-binding protein or a homologue thereof, as defined hereinabove.

According to a further preferred embodiment of the invention, plant growth characteristics may be improved by introducing and expressing in a plant a nucleic acid encoding an RBP1 polypeptide or a homologue thereof.

One preferred method for introducing a genetic modification (which in this case need not be in the locus of an rbp1 gene) is to introduce and express in a plant a nucleic acid encoding an RBP1 polypeptide or a homologue thereof. An RBP1 polypeptide or a homologue thereof as mentioned above is one having: (a) RNA-binding activity; (b) two RRM domains, (c) the following two motifs: (i) KIFVGGL (SEQ ID NO: 41); and (ii) RPRGFGF (SEQ ID NO: 42), allowing for up to three amino acid substitutions and any conservative change in the motifs; and (d) having, in increasing order of preference, at least 20%, 25%, 30%, 35%, 40%, 45%, 50%, 55%, 60%, 65%, 70%, 75%, 80%, 85%, 90%, 95% sequence identity to the amino acid represented by SEQ ID NO: 15.

"Homologues" of a protein encompass peptides, oligopeptides, polypeptides, proteins and enzymes having amino acid substitutions, deletions and/or insertions relative to the unmodified protein in question and having similar biological and functional activity as the unmodified protein from which they are derived. To produce such homologues, amino acids of the protein may be replaced by other amino acids having similar properties (such as similar hydrophobicity, hydrophilicity, antigenicity, propensity to form or break α-helical structures or β-sheet structures). Conservative substitution tables are well known in the art (see for example Creighton (1984) Proteins. W. H. Freeman and Company). The table below gives examples of conserved amino acid substitutions.

TABLE 4

Examples of conserved amino acid substitutions

| Residue | Conservative Substitutions |
|---|---|
| Ala | Ser |
| Arg | Lys |
| Asn | Gln; His |
| Asp | Glu |
| Gln | Asn |
| Cys | Ser |
| Glu | Asp |
| Gly | Pro |
| His | Asn; Gln |
| Ile | Leu, Val |
| Leu | Ile; Val |
| Lys | Arg; Gln |
| Met | Leu; Ile |
| Phe | Met; Leu; Tyr |
| Ser | Thr; Gly |
| Thr | Ser; Val |
| Trp | Tyr |
| Tyr | Trp; Phe |
| Val | Ile; Leu |

Also encompassed by the term "homologues" are two special forms of homology, which include orthologous sequences and paralogous sequences, which encompass evolutionary concepts used to describe ancestral relationships of genes. The term "paralogous" relates to gene-duplications within the genome of a species leading to paralogous genes. The term "orthologous" relates to homologous genes in different organisms due to speciation.

Othologues in, for example, monocot plant species may easily be found by performing a so-called reciprocal blast search. This may be done by a first blast involving blasting the sequence in question (for example, SEQ ID NO: 1 or 2 or SEQ ID NO: 14 or 15) against any sequence database, such as the publicly available NCBI database which may be found at: ncbi.nlm.nih.gov. If orthologues in rice were sought, the sequence in question would be blasted against, for example, the 28,469 full-length cDNA clones from Oryza sativa Nipponbare available at NCBI. BLASTn or tBLASTX may be used when starting from nucleotides or BLASTP or TBLASTN when starting from the protein, with standard default values. The blast results may be filtered. The full-length sequences of either the filtered results or the non-filtered results are then blasted back (second blast) against the sequences of the organism from which the sequence in question is derived. The results of the first and second blasts are then compared. An orthologue is found when the results of the second blast give as hits with the highest similarity an RNA-binding protein-encoding nucleic acid or RNA-binding protein polypeptide, for example, if one of the organisms is tobacco then a paralogue is found. For RBP1, an orthologue is found when the results of the second blast give as hits with the highest similarity an rbpl nucleic acid or RBP1 polypeptide, for example, if one of the organisms is *Arabidopsis thaliana* then a paralogue is found. In the case of large families, ClustalW may be used, followed by a neighbour joining tree, to help visualize the clustering.

A homologue may be in the form of a "substitutional variant" of a protein, i.e. where at least one residue in an amino acid sequence has been removed and a different residue inserted in its place. Amino acid substitutions are typically of single residues, but may be clustered depending upon functional constraints placed upon the polypeptide; insertions will usually be of the order of about 1 to 10 amino acid residues. Preferably, amino acid substitutions comprise conservative amino acid substitutions.

A homologue may also be in the form of an "insertional variant" of a protein, i.e. where one or more amino acid residues are introduced into a predetermined site in a protein. Insertions may comprise amino-terminal and/or carboxy-terminal fusions as well as intra-sequence insertions of single or multiple amino acids. Generally, insertions within the amino acid sequence will be smaller than amino- or carboxy-terminal fusions, of the order of about 1 to 10 residues. Examples of amino- or carboxy-terminal fusion proteins or peptides include the binding domain or activation domain of a transcriptional activator as used in the yeast two-hybrid system, phage coat proteins, (histidine)6-tag, glutathione S-transferase-tag, protein A, maltose-binding protein, dihydrofolate reductase, Tag•100 epitope, c-myc epitope, FLAG®-epitope, lacZ, CMP (calmodulin-binding peptide), HA epitope, protein C epitope and VSV epitope.

Homologues in the form of "deletion variants" of a protein are characterised by the removal of one or more amino acids from a protein.

Amino acid variants of a protein may readily be made using peptide synthetic techniques well known in the art, such as solid phase peptide synthesis and the like, or by recombinant DNA manipulations. Methods for the manipulation of DNA sequences to produce substitution, insertion or deletion variants of a protein are well known in the art. For example, techniques for making substitution mutations at predetermined sites in DNA are well known to those skilled in the art and include M13 mutagenesis, T7-Gen in vitro mutagenesis (USB, Cleveland, Ohio), QuickChange Site Directed mutagenesis (Stratagene, San Diego, Calif.), PCR-mediated site-directed mutagenesis or other site-directed mutagenesis protocols.

The RNA-binding protein or homologue thereof may be a derivative or the RBP1 polypeptide or homologue thereof may be a derivative. "Derivatives" include peptides, oligopeptides, polypeptides, proteins and enzymes which may comprise substitutions, deletions or additions of naturally and non-naturally occurring amino acid residues compared to the amino acid sequence of a naturally-occurring form of the protein, for example, as presented in SEQ ID NO: 2, or SEQ ID NO: 15 in the case of RBP1. "Derivatives" of a protein encompass peptides, oligopeptides, polypeptides, proteins and enzymes which may comprise naturally occurring altered, glycosylated, acylated or non-naturally occurring amino acid residues compared to the amino acid sequence of a naturally-occurring form of the polypeptide. A derivative may also comprise one or more non-amino acid substituents compared to the amino acid sequence from which it is derived, for example a reporter molecule or other ligand, covalently or non-covalently bound to the amino acid sequence, such as a reporter molecule which is bound to facilitate its detection, and non-naturally occurring amino acid residues relative to the amino acid sequence of a naturally-occurring protein.

The RNA-binding protein or homologue thereof may be encoded by an alternative splice variant of an RNA-binding protein nucleic acid/gene. The RBP 1 polypeptide or homologue thereof may be encoded by an alternative splice variant of an rbp 1 nucleic acid/gene. The term "alternative splice variant" as used herein encompasses variants of a nucleic acid sequence in which selected introns and/or exons have been excised, replaced or added. Such variants will be ones in which the biological activity of the protein is retained, which may be achieved by selectively retaining functional segments of the protein. Such splice variants may be found in nature or may be manmade. Methods for making such splice variants are well known in the art. Preferred splice variants are splice variants of the nucleic acid represented by SEQ ID NO: 1, SEQ ID NO: 3, SEQ ID NO: 5, SEQ ID NO: 7 and SEQ ID NO: 9. Further preferred are splice variants encoding a polypeptide retaining RNA-binding activity and having at least 1 RRM, preferably two or three RRMs and at least one, preferably both, of motifs I or II. Preferred splice variants of RBP1 are splice variants of the nucleic acid represented by SEQ ID NO: 15, SEQ ID NO: 17, SEQ ID NO: 19, SEQ ID NO: 21, SEQ ID NO: 23, SEQ ID NO: 25 or SEQ ID NO: 27, SEQ ID NO: 29, SEQ ID NO: 31, SEQ ID NO: 33, SEQ ID NO: 35 and SEQ ID NO: 37. Further preferred are splice variants encoding a polypeptide retaining RNA-binding activity and having one, preferably two RRM domains and further preferably the following two motifs: (i) KIFVGGL (SEQ ID NO: 41); and (ii) RPRGFGF (SEQ ID NO: 42), allowing for up to three amino acid substitutions and any conservative change in the motifs.

The homologue may also be encoded by an allelic variant of a nucleic acid encoding an RNA-binding protein or a homologue thereof, preferably an allelic variant of the nucleic acid represented by any one of SEQ ID NO: 1, SEQ ID NO: 3, SEQ ID NO: 5, SEQ ID NO: 7 and SEQ ID NO: 9. Further preferably, the polypeptide encoded by the allelic variant has RNAbinding activity and at least 1 RRM, preferably two or three RRMs and at least one, preferably both, of motifs I or II. The homologue may also be encoded by an allelic variant of a nucleic acid encoding an RBP1 polypeptide or a homologue thereof, preferably an allelic variant of the nucleic acid represented by SEQ ID NO: SEQ ID NO: 15, SEQ ID NO: 17, SEQ ID NO: 19, SEQ ID NO: 21, SEQ ID NO: 23, SEQ ID NO: 25 or SEQ ID NO: 27, SEQ ID NO: 29, SEQ ID NO: 31, SEQ ID NO: 33, SEQ ID NO: 35 and SEQ ID NO: 37. Further preferably, the polypeptide encoded by the allelic variant has RNA-binding activity and one, preferably two RRM domains and the following two motifs: (i) KIFVGGL (SEQ ID NO: 41); and (ii) RPRGFGF (SEQ ID NO: 42), allowing for up to three amino acid substitutions and any conservative change in the motifs. Allelic variants exist in nature and encompassed within the methods of the present invention is the use of these natural alleles. Allelic variants encompass Single Nucleotide Polymorphisms (SNPs), as well as Small Insertion/Deletion Polymorphisms (INDELs). The size of INDELs is usually less than 100 bp. SNPs and INDELs form the largest set of sequence variants in naturally occurring polymorphic strains of most organisms.

According to a preferred aspect of the present invention, enhanced or increased expression of the RNA-binding protein encoding nucleic acid or variant thereof is envisaged. According to a preferred aspect of the present invention, enhanced or increased expression of the rbp1 nucleic acid or variant thereof is envisaged. Methods for obtaining enhanced or increased expression of genes or gene products are well documented in the art and include, for example, overexpression driven by appropriate promoters, the use of transcription enhancers or translation enhancers. Isolated nucleic acids which serve as promoter or enhancer elements may be introduced in an appropriate position (typically upstream) of a non-heterologous form of a polynucleotide so as to upregulate expression of an RNA-binding protein-encoding nucleic acid or variant thereof. For example, endogenous promoters may be altered in vivo by mutation, deletion, and/or substitution (see, Kmiec, U.S. Pat. No. 5,565,350; Zarling et al., PCT/US93/03868), or isolated promoters may be introduced into a plant cell in the proper orientation and distance from a gene of the present invention so as to control the expression of the gene.

If polypeptide expression is desired, it is generally desirable to include a polyadenylation region at the 3'-end of a polynucleotide coding region. The polyadenylation region can be derived from the natural gene, from a variety of other plant genes, or from T-DNA. The 3' end sequence to be added may be derived from, for example, the nopaline synthase or octopine synthase genes, or alternatively from another plant gene, or less preferably from any other eukaryotic gene.

An intron sequence may also be added to the 5' untranslated region or the coding sequence of the partial coding sequence to increase the amount of the mature message that accumulates in the cytosol. Inclusion of a spliceable intron in the transcription unit in both plant and animal expression constructs has been shown to increase gene expression at both the mRNA and protein levels up to 1000-fold, Buchman and Berg, Mol. Cell biol. 8:4395-4405 (1988); Callis et al., Genes Dev. 1:1183-1200 (1987). Such intron enhancement of gene expression is typically greatest when placed near the 5' end of the transcription unit. Use of the maize introns Adh1-S intron 1, 2, and 6, the Bronze-1 intron are known in the art. See generally, The Maize Handbook, Chapter 116, Freeling and Walbot, Eds., Springer, N.Y. (1994).

The invention also provides genetic constructs and vectors to facilitate introduction and/or expression of the nucleotide sequences useful in the methods according to the invention.

Therefore, there is provided a gene construct comprising:
  (i) An RNA-binding protein-encoding nucleic acid or variant thereof;
  (ii) one or more control sequences capable of driving expression of the nucleic acid sequence of (i); and optionally
  (iii) a transcription termination sequence.

There is also provided, a gene construct comprising:
  (i) An rbp1 nucleic acid or variant thereof;
  (ii) one or more control sequences capable of driving expression of the nucleic acid sequence of (i); and optionally
  (iii) a transcription termination sequence.

Constructs useful in the methods according to the present invention may be constructed using recombinant DNA technology well known to persons skilled in the art. The gene constructs may be inserted into (commercially available) vectors suitable for transforming into plants cells and suitable for expression of the gene of interest in the transformed cells.

Plants are transformed with a vector comprising the sequence of interest (i.e., an RNA-binding protein-encoding nucleic acid or variant thereof or an rbp1 nucleic acid or variant thereof). The sequence of interest is operably linked to one or more control sequences (at least to a promoter). The terms "regulatory element", "control sequence" and "promoter" are all used interchangeably herein and are to be taken in a broad context to refer to regulatory nucleic acid sequences capable of effecting expression of the sequences to which they are ligated. Encompassed by the aforementioned terms are transcriptional regulatory sequences derived from a classical eukaryotic genomic gene (including the TATA box which is required for accurate transcription initiation, with or without a CCAAT box sequence) and additional regulatory elements (i.e. upstream activating sequences, enhancers and silencers) which alter gene expression in response to developmental and/or external stimuli, or in a tissue-specific manner. Also included within the term is a transcriptional regulatory sequence of a classical prokaryotic gene, in which case it may include a −35 box sequence and/or −10 box transcriptional regulatory sequences. The term "regulatory element" also encompasses a synthetic fusion molecule or derivative which confers, activates or enhances expression of a nucleic acid molecule in a cell, tissue or organ. The term "operably linked" as used herein refers to a functional linkage between the promoter sequence and the gene of interest, such that the promoter sequence is able to initiate transcription of the gene of interest.

Advantageously, any type of promoter may be used to drive expression of the nucleic acid sequence. The promoter may be an inducible promoter, i.e. having induced or increased transcription initiation in response to a developmental, chemical, environmental or physical stimulus. An example of an inducible promoter being a stress-inducible promoter, i.e. a promoter activated when a plant is exposed to various stress conditions. Additionally or alternatively, the promoter may be a tissue-preferred promoter, i.e. one that is capable of predominantly initiating transcription in certain tissues, such as the leaves, roots, seed tissue etc.

Preferably, the RNA-binding protein-encoding nucleic acid or variant thereof is operably linked to a seed-preferred promoter. A seed-preferred promoter is one that preferentially, but not necessarily exclusively, drives expression in seed-tissue. Preferably, the seed-tissue is the endosperm. Preferably, the promoter is a prolamin promoter, such as the prolamin promoter from rice (SEQ ID NO: 11). It should be clear that the applicability of the present invention is not restricted to the RNA-binding protein-encoding nucleic acid represented by SEQ ID NO: 1, nor is the applicability of the invention restricted to expression of an RNA-binding protein-encoding nucleic acid when driven by a prolamin promoter.

Preferably, the rbp1 nucleic acid or variant thereof is operably linked to a promoter capable of preferentially expressing the nucleic acid in shoots. Preferably, the promoter capable of preferentially expressing the nucleic acid in shoots has a comparable expression profile to a beta-expansin promoter, for example as shown in FIG. 5. Most preferably, the promoter capable of preferentially expressing the nucleic acid in shoots is the beta-expansin promoter from rice (SEQ ID NO: 38). It should be clear that the applicability of the present invention is not restricted to the rbp1 nucleic acid represented by SEQ ID NO: 14, nor is the applicability of the invention restricted to expression of an rbp1 nucleic acid when driven by a beta expansin promoter.

Optionally, one or more terminator sequences may also be used in the construct introduced into a plant. The term "terminator" encompasses a control sequence which is a DNA sequence at the end of a transcriptional unit which signals 3' processing and polyadenylation of a primary transcript and termination of transcription. Additional regulatory elements may include transcriptional as well as translational enhancers. Those skilled in the art will be aware of terminator and enhancer sequences which may be suitable for use in performing the invention The genetic constructs of the invention may further include an origin of replication sequence which is required for maintenance and/or replication in a specific cell type. One example is when a genetic construct is required to be maintained in a bacterial cell as an episomal genetic element (e.g. plasmid or cosmid molecule). Preferred origins of replication include, but are not limited to, the f1-ori and colE1.

The genetic construct may optionally comprise a selectable marker gene. As used herein, the term "selectable marker gene" includes any gene that confers a phenotype on a cell in which it is expressed to facilitate the identification and/or selection of cells that are transfected or transformed with a nucleic acid construct of the invention. Suitable markers may be selected from markers that confer antibiotic or herbicide resistance, that introduce a new metabolic trait or that allow visual selection. Examples of selectable marker genes include genes conferring resistance to antibiotics (such as nptII that phosphorylates neomycin and kanamycin, or hpt, phosphorylating hygromycin), to herbicides (for example bar which provides resistance to Basta; aroA or gox providing resistance against glyphosate), or genes that provide a metabolic trait (such as manA that allows plants to use mannose as sole carbon source). Visual marker genes result in the formation of colour (for example β-glucuronidase, GUS), luminescence (such as luciferase) or fluorescence (Green Fluorescent Protein, GFP, and derivatives thereof).

The present invention also encompasses plants obtainable by the methods according to the present invention. The present invention therefore provides plants obtainable by the method according to the present invention, which plants have introduced therein an RNA-binding protein-encoding nucleic acid or variant thereof or an rbp1 nucleic acid or variant thereof.

The invention also provides a method for the production of transgenic plants having improved growth characteristics, comprising introduction and expression in a plant of an RNA-binding protein-encoding nucleic acid or a variant thereof.

More specifically, the present invention provides a method for the production of transgenic plants having improved growth characteristics, which method comprises:
(i) introducing into a plant or plant cell an RNA-binding protein-encoding nucleic acid or variant thereof; and
(ii) cultivating the plant cell under conditions promoting plant growth and development.

The invention also provides a method for the production of transgenic plants having improved growth characteristics, comprising introduction and expression in a plant of an rbp1 nucleic acid or a variant thereof.

More specifically, the present invention provides a method for the production of transgenic plants having improved growth characteristics, which method comprises:
(iii) introducing into a plant or plant cell an rbp1 nucleic acid or variant thereof; and
(iv) cultivating the plant cell under conditions promoting plant growth and development.

The nucleic acid may be introduced directly into a plant cell or into the plant itself (including introduction into a tissue, organ or any other part of a plant). According to a preferred feature of the present invention, the nucleic acid is preferably introduced into a plant by transformation.

The term "transformation" as referred to herein encompasses the transfer of an exogenous polynucleotide into a host cell, irrespective of the method used for transfer. Plant tissue capable of subsequent clonal propagation, whether by organogenesis or embryogenesis, may be transformed with a genetic construct of the present invention and a whole plant regenerated therefrom. The particular tissue chosen will vary depending on the clonal propagation systems available for, and best suited to, the particular species being transformed. Exemplary tissue targets include leaf disks, pollen, embryos, cotyledons, hypocotyls, megagametophytes, callus tissue, existing meristematic tissue (e.g., apical meristem, axillary buds, and root meristems), and induced meristem tissue (e.g., cotyledon meristem and hypocotyl meristem). The polynucleotide may be transiently or stably introduced into a host cell and may be maintained non-integrated, for example, as a plasmid. Alternatively, it may be integrated into the host genome. The resulting transformed plant cell may then be used to regenerate a transformed plant in a manner known to persons skilled in the art.

Transformation of plant species is now a fairly routine technique. Advantageously, any of several transformation methods may be used to introduce the gene of interest into a suitable ancestor cell. Transformation methods include the use of liposomes, electroporation, chemicals that increase free DNA uptake, injection of the DNA directly into the plant, particle gun bombardment, transformation using viruses or pollen and microprojection. Methods may be selected from the calcium/polyethylene glycol method for protoplasts (Krens, F. A. et al., 1882, Nature 296, 72-74; Negrutiu I. et al., June 1987, Plant Mol. Biol. 8, 363-373); electroporation of protoplasts (Shillito R. D. et al., 1985 Bio/Technol 3, 1099-1102); microinjection into plant material (Crossway A. et al., 1986, Mol. Gen Genet 202, 179-185); DNA or RNA-coated particle bombardment (Klein T. M. et al., 1987, Nature 327, 70) infection with (non-integrative) viruses and the like. Transgenic rice plants expressing an RNA-binding protein are preferably produced via Agrobacterium-mediated transformation using any of the well known methods for rice transformation, such as described in any of the following: published European patent application EP 1198985 A1, Aldemita and Hodges (Planta, 199, 612-617, 1996); Chan et al. (Plant Mol. Biol. 22 (3) 491-506, 1993), Hiei et al. (Plant J. 6 (2) 271-282, 1994), which disclosures are incorporated by reference herein as if fully set forth. In the case of corn transformation, the preferred method is as described in either Ishida et al. (Nat. Biotechnol. June 1996; 14(6): 745-50) or Frame et al. (Plant Physiol. May 2002; 129(1): 13-22), which disclosures are incorporated by reference herein as if fully set forth.

Generally after transformation, plant cells or cell groupings are selected for the presence of one or more markers which are encoded by plant-expressible genes co-transferred with the gene of interest, following which the transformed material is regenerated into a whole plant.

Following DNA transfer and regeneration, putatively transformed plants may be evaluated, for instance using Southern analysis, for the presence of the gene of interest, copy number and/or genomic organisation. Alternatively or additionally, expression levels of the newly introduced DNA may be monitored using Northern and/or Western analysis, both techniques being well known to persons having ordinary skill in the art.

The generated transformed plants may be propagated by a variety of means, such as by clonal propagation or classical breeding techniques. For example, a first generation (or T1) transformed plant may be selfed to give homozygous second generation (or T2) transformants, and the T2 plants further propagated through classical breeding techniques.

The generated transformed organisms may take a variety of forms. For example, they may be chimeras of transformed cells and non-transformed cells; clonal transformants (e.g., all cells transformed to contain the expression cassette); grafts of transformed and untransformed tissues (e.g., in plants, a transformed rootstock grafted to an untransformed scion).

The present invention clearly extends to any plant cell or plant produced by any of the methods described herein, and to all plant parts and propagules thereof. The present invention extends further to encompass the progeny of a primary transformed or transfected cell, tissue, organ or whole plant that has been produced by any of the aforementioned methods, the only requirement being that progeny exhibit the same genotypic and/or phenotypic characteristic(s) as those produced in the parent by the methods according to the invention. The invention also includes host cells containing an isolated RNA-binding protein nucleic add or variant thereof. Preferred host cells according to the invention are plant cells. The invention also extends to harvestable parts of a plant, such as but not limited to seeds, leaves, fruits, flowers, stem cultures, rhizomes, tubers and bulbs.

The present invention also encompasses the use of RNA-binding protein nucleic acids or variants thereof and to the use of RNA-binding proteins or homologues thereof.

One such use relates to improving the growth characteristics of plants, in particular in improving yield, especially seed yield. The seed yield may include one or more of the following: increased number of (filled) seeds, increased seed weight, increased harvest index, among others.

RNA-binding protein-encoding nucleic acids or variants thereof or RNA-binding proteins or homologues thereof may find use in breeding programmes in which a DNA marker is identified which may be genetically linked to an RNA-binding protein-encoding gene or variant thereof. The RNA-binding protein or variants thereof or RNA-binding proteins or homologues thereof may be used to define a molecular marker. This DNA or protein marker may then be used in breeding programs to select plants having altered growth characteristics. The RNA-binding protein-encoding gene or variant thereof may, for example, be a nucleic acid as represented by any one of SEQ ID NO: 1, SEQ ID NO: 3, SEQ ID NO: 5, SEQ ID NO: 7 and SEQ ID NO: 9.

Allelic variants of an RNA-binding protein-encoding gene/nucleic acid may also find use in marker-assisted breeding programmes. Such breeding programmes sometimes require introduction of allelic variation by mutagenic treatment of the plants, using for example EMS mutagenesis; alternatively, the programme may start with a collection of allelic variants of so called "natural" origin caused unintentionally. Identification of allelic variants then takes place by, for example, PCR. This is followed by a selection step for selection of superior allelic variants of the sequence in question and which give improved growth characteristics in a plant. Selection is typically carried out by monitoring growth performance of plants containing different allelic variants of the sequence in question, for example, different allelic variants of any one of SEQ ID NO: 1, SEQ ID NO: 3, SEQ ID NO: 5, SEQ ID NO: 7 and SEQ ID NO: 9. Growth performance may be monitored in a greenhouse or in the field. Further optional steps include crossing plants, in which the superior allelic variant was identified, with another plant. This could be used, for example, to make a combination of interesting phenotypic features.

RNA-binding protein-encoding nucleic acids or variants thereof may also be used as probes for genetically and physically mapping the genes that they are a part of, and as markers for traits linked to those genes. Such information may be useful in plant breeding in order to develop lines with desired phenotypes. Such use of RNA-binding protein-encoding nucleic acids or variants thereof requires only a nucleic acid sequence of at least 15 nucleotides in length. The RNA-binding protein-encoding nucleic acids or variants thereof may be used as restriction fragment length polymorphism (RFLP) markers. Southern blots (Maniatis) of restriction-digested plant genomic DNA may be probed with the RNA-binding protein-encoding nucleic acids or variants thereof. The resulting banding patterns may then be subjected to genetic analyses using computer programs such as Map-Maker (Lander et al. (1987) Genomics 1:174-181) in order to construct a genetic map. In addition, the nucleic acids may be used to probe Southern blots containing restriction endonuclease-treated genomic DNAs of a set of individuals representing parent and progeny of a defined genetic cross. Segregation of the DNA polymorphisms is noted and used to calculate the position of the RNA-binding protein encoding nucleic acid or variant thereof in the genetic map previously obtained using this population (Botstein et al. (1980) Am. J. Hum. Genet. 32:314-331).

The production and use of plant gene-derived probes for use in genetic mapping is described in Bematzky and Tanksley (1986) Plant Mol. Biol. Reporter 4:37-41. Numerous publications describe genetic mapping of specific cDNA clones using the methodology outlined above or variations thereof. For example, F2 intercross populations, backcross populations, randomly mated populations, near isogenic lines, and other sets of individuals may be used for mapping. Such methodologies are well known to those skilled in the art.

The nucleic acid probes may also be used for physical mapping (i.e., placement of sequences on physical maps; see Hoheisel et al. In: Non-mammalian Genomic Analysis: A Practical Guide, Academic press 1996, pp. 319-346, and references cited therein).

In another embodiment, the nucleic acid probes may be used in direct fluorescence in situ hybridization (FISH) mapping (Trask (1991) Trends Genet. 7:149-154). Although current methods of FISH mapping favor use of large clones (several to several hundred KB; see Laan et al. (1995) Genome Res. 5:13-20), improvements in sensitivity may allow performance of FISH mapping using shorter probes.

A variety of nucleic acid amplification-based methods of genetic and physical mapping may be carried out using the nucleic acids. Examples include allele-specific amplification (Kazazian (1989) J. Lab. Clin. Med 11:95-96), polymorphism of PCR-amplified fragments (CAPS; Sheffield et al. (1993) Genomics 16:325-332), allele-specific ligation (Landegren et al. (1988) Science 241:1077-1080), nucleotide extension reactions (Sokolov (1990) Nucleic Acid Res. 18:3671), Radiation Hybrid Mapping (Walter et al. (1997) Nat. Genet. 7:22-28) and Happy Mapping (Dear and Cook (1989) Nucleic Acid Res. 17:6795-6807). For these methods, the sequence of a nucleic acid is used to design and produce primer pairs for use in the amplification reaction or in primer extension reactions. The design of such primers is well known to those skilled in the art. In methods employing PCR-based genetic mapping, it may be necessary to identify DNA sequence differences between the parents of the mapping cross in the region corresponding to the instant nucleic acid sequence. This, however, is generally not necessary for mapping methods.

RNA-binding protein-encoding nucleic acids or variants thereof or RNA-binding proteins or homologues thereof may also find use as growth regulators. Since these molecules have been shown to be useful in improving the growth characteristics of plants, they would also be useful growth regulators, such as herbicides or growth stimulators. The present invention therefore provides a composition comprising an RNA-binding protein-encoding nucleic acid/gene or variant thereof or an RNA-binding protein or homologue thereof, together with a suitable carrier, diluent or excipient, for use as a growth regulator.

The present invention also encompasses the use of rbp1 nucleic acids or variants thereof and to the use of RBP1 polypeptides or homologues thereof.

One such use relates to improving the growth characteristics of plants, in particular in improving yield, especially seed yield. The seed yield may include one or more of the following: increased number of (filled) seeds, increased seed weight, among others.

Rbp1 nucleic acids or variants thereof or RPB1 polypeptides or homologues thereof may find use in breeding programmes in which a DNA marker is identified which may be genetically linked to an rbp1 gene or variant thereof. The rbp1 or variants thereof or RBP1 or homologues thereof may be used to define a molecular marker. This DNA or protein marker may then be used in breeding programs to select plants having altered growth characteristics. The rbp1 gene or variant thereof may, for example, be a nucleic acid as represented by any one of SEQ ID NO: 14, SEQ ID NO: 16, SEQ ID NO: 18, SEQ ID NO: 20, SEQ ID NO: 22, SEQ ID NO: 24, SEQ ID NO: 26, SEQ ID NO: 28, SEQ ID NO: 30, SEQ ID NO: 32, SEQ ID NO: 34 and SEQ ID NO: 36.

Allelic variants of an rbp1 may also find use in marker-assisted breeding programmes. Such breeding programmes sometimes require introduction of allelic variation by mutagenic treatment of the plants, using for example EMS mutagenesis; alternatively, the programme may start with a collection of allelic variants of so called "natural" origin caused unintentionally. Identification of allelic variants then takes place by, for example, PCR. This is followed by a selection step for selection of superior allelic variants of the sequence in question and which give rise improved growth characteristics in a plant. Selection is typically carried out by monitoring growth performance of plants containing different allelic variants of the sequence in question, for example, different allelic variants of any one of SEQ ID NO: 14, SEQ ID NO: 16, SEQ ID NO: 18, SEQ ID NO: 20, SEQ ID NO: 22, SEQ ID NO: 24, SEQ ID NO: 26, SEQ ID NO: 28, SEQ ID NO: 30, SEQ ID NO: 32, SEQ ID NO: 34 and SEQ ID NO: 36. Growth performance may be monitored in a greenhouse or in the field. Further optional steps include crossing plants, in which the superior allelic variant was identified, with another plant. This could be used, for example, to make a combination of interesting phenotypic features.

An rbp1 nucleic acid or variant thereof may also be used as probes for genetically and physically mapping the genes that they are a part of, and as markers for traits linked to those genes. Such information may be useful in plant breeding in order to develop lines with desired phenotypes. Such use of rbp1 nucleic acids or variants thereof requires only a nucleic acid sequence of at least 15 nucleotides in length. The rbp1 nucleic acids or variants thereof may be used as restriction fragment length polymorphism (RFLP) markers. Southern blots (Maniatis) of restriction-digested plant genomic DNA may be probed with the rbp1 nucleic acids or variants thereof. The resulting banding patterns may then be subjected to genetic analyses using computer programs such as MapMaker (Lander et al. (1987) Genomics 1:174-181) in order to construct a genetic map. In addition, the nucleic acids may be used to probe Southern blots containing restriction endonuclease-treated genomic DNAs of a set of individuals representing parent and progeny of a defined genetic cross. Segregation of the DNA polymorphisms is noted and used to calculate the position of the rbp1 nucleic acid or variant thereof in the genetic map previously obtained using this population (Botstein et al. (1980) Am. J. Hum. Genet. 32:314-331).

The production and use of plant gene-derived probes for use in genetic mapping is described in Bematzky and Tanksley (1986) Plant Mol. Biol. Reporter 4:37-41. Numerous publications describe genetic mapping of specific cDNA clones using the methodology outlined above or variations thereof. For example, F2 intercross populations, backcross populations, randomly mated populations, near isogenic lines, and other sets of individuals may be used for mapping. Such methodologies are well known to those skilled in the art.

The nucleic acid probes may also be used for physical mapping (i.e., placement of sequences on physical maps; see Hoheisel et al. In: Nonmammalian Genomic Analysis: A Practical Guide, Academic press 1996, pp. 319-346, and references cited therein).

In another embodiment, the nucleic acid probes may be used in direct fluorescence in situ hybridization (FISH) mapping (Trask (1991) Trends Genet. 7:149-154). Although current methods of FISH mapping favor use of large clones (several to several hundred KB; see Laan et al. (1995) Genome Res. 5:13-20), improvements in sensitivity may allow performance of FISH mapping using shorter probes.

A variety of nucleic acid amplification-based methods of genetic and physical mapping may be carried out using the nucleic acids. Examples include allele-specific amplification (Kazazian (1989) J. Lab. Clin. Med 11:95-96), polymorphism of PCR-amplified fragments (CAPS; Sheffield et al. (1993) Genomics 16:325-332), allele-specific ligation (Landegren et al. (1988) Science 241:1077-1080), nucleotide extension reactions (Sokolov (1990) Nucleic Acid Res. 18:3671), Radiation Hybrid Mapping (Walter et al. (1997) Nat. Genet. 7:22-28) and Happy Mapping (Dear and Cook (1989) Nucleic Acid Res. 17:6795-6807). For these methods, the sequence of a nucleic acid is used to design and produce primer pairs for use in the amplification reaction or in primer extension reactions. The design of such primers is well known to those skilled in the art. In methods employing PCR-based genetic mapping, it may be necessary to identify DNA sequence differences between the parents of the mapping cross in the region corresponding to the instant nucleic acid sequence. This, however, is generally not necessary for mapping methods.

rbp1 nucleic acids or variants thereof or RBP1 polypeptides or homologues thereof may also find use as growth regulators. Since these molecules have been shown to be useful in improving the growth characteristics of plants, they would also be useful growth regulators, such as herbicides or growth stimulators. The present invention therefore provides a composition comprising an rbp1 or variant thereof or an RBP1 polypeptide or homologue thereof, together with a suitable carrier, diluent or excipient, for use as a growth regulator.

The methods according to the present invention result in plants having improved growth characteristics, as described hereinabove. These advantageous growth characteristics may also be combined with other economically advantageous traits, such as further yield-enhancing traits, tolerance to various stresses, traits modifying various architectural features and/or biochemical and/or physiological features.

DESCRIPTION OF FIGURES

The present invention will now be described with reference to the following figures in which:

FIG. 1 shows a CLUSTAL multiple alignment of plant RNA-binding proteins. Motifs I and II are boxed (M2 is absent from BAC83046) and RRM domains are underlined. The sequences are: "newriceCDS701homologue": SEQ ID NO: 4; "rice" SEQ ID NO: 8; "maize": SEQ ID NO: 6; "CDS701Proteinprediction": SEQ ID NO: 2; and "BAC83046.1": SEQ ID NO: 10.

FIG. 3 shows a multiple alignment of plant RBP1 polypeptides. Genebank protein or their encoding nucleic acids are indicated. At denotes *Arabidopsis thaliana* and Os denotes *Oryza sativa*. The sequences are: "Translation of AK067725-Os-RBP1": 31; "Translation of AK070544-Os-RBP1": SEQ ID NO: 33; "Translation of NM 196957-Os-RBP1": SEQ ID NO: 29; "NP 176143-At-RBP1": SEQ ID NO 15; "NP 567753-At-RBP1": SEQ ID NO: 17; "NP 974937-At-RBP1": SEQ ID NO 19; "NP193166-At-RBP1": SEQ ID NO: 43; "NP 850539-At-RBP1": SEQ ID NO: 44; "NP 180899-At-RBP1": SEQ ID NO: 25; and "NP 974899-At-RBP1": SEQ ID NO: 45.

FIG. 6 details examples of sequences useful in performing the methods according to the present invention. From SEQ ID NO: 14 onwards, the At number given refers to the MIPs Accession number (mips.gsf.de/); other identifiers refer to Genbank accession numbers. Capital letters represent the coding sequence and small letters refer to non-translated regions, including 5' leader sequences, 3' untranslated regions and introns. Chromosomic location of the gene is indicated by the contig number and coordinates of the ORF in the contig.

EXAMPLES

Figure 2:
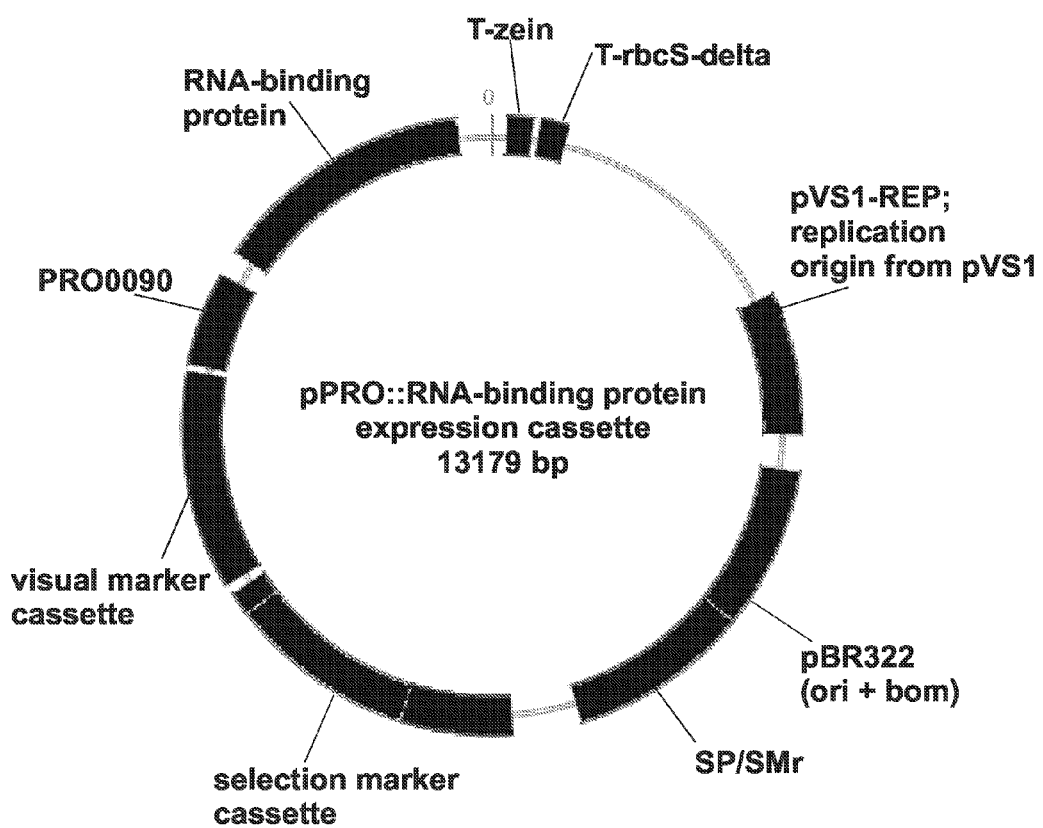
FIG. 2 shows a binary vector for expression in *Oryza sativa* of a tobacco RNA-binding protein under the control of a prolamin promoter.
Figure 4:
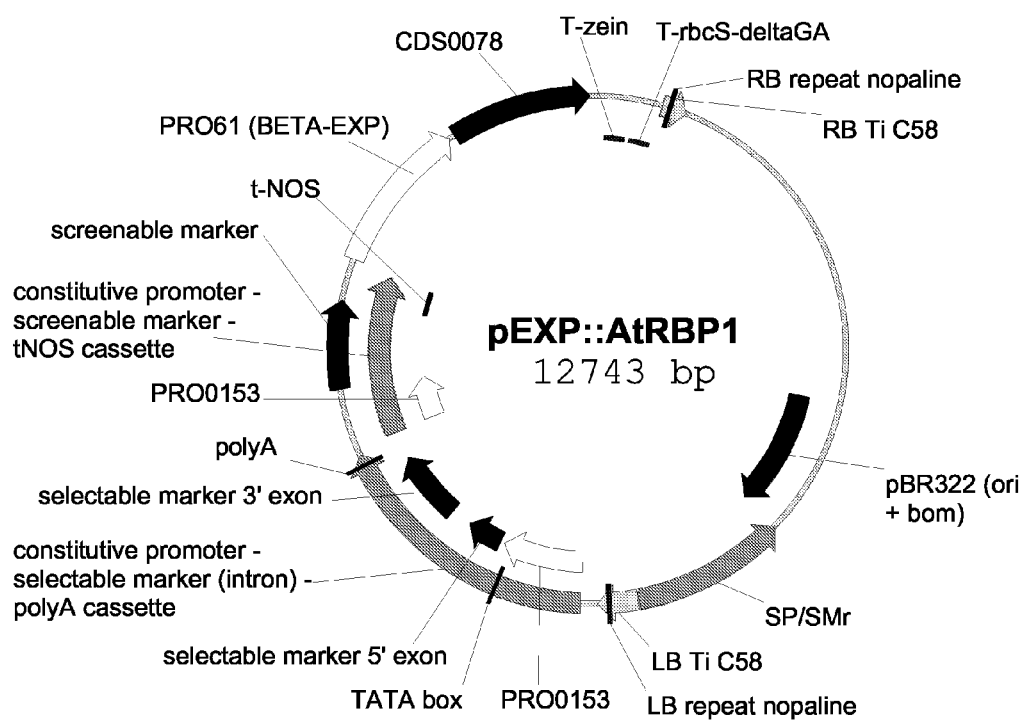
FIG. 4 shows a binary vector for expression in *Oryza sativa* of an *Arabidopsis thaliana* RBP1 (internal reference CDS0078) under the control of a beta expansin promoter (internal reference PRO0061).
Figure 5:
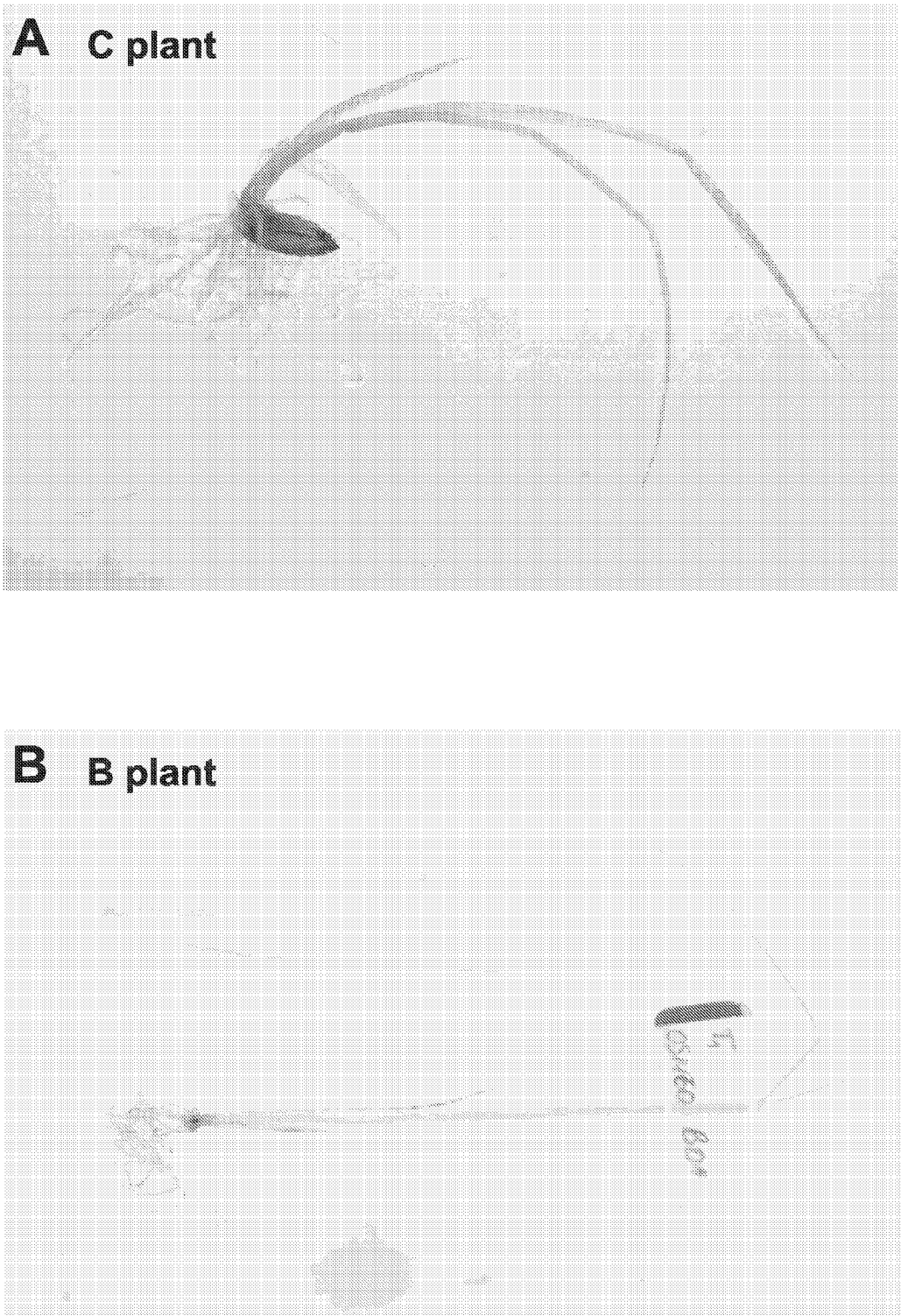
FIG. 5 shows photographs of GUS expression driven by a beta expansin promoter. The photograph of the "C plant" is of a rice plant GUS stained when it had reached a size of about 5 cm. The photograph of the "B plant" is of a rice plant GUS stained when it had reached a size of about 10 cm. Promoters with comparable expression profiles may also be useful in the methods of the invention.

The present invention will now be described with reference to the following examples, which are by way of illustration alone.

DNA manipulation: unless otherwise stated, recombinant DNA techniques are performed according to standard protocols described in (Sambrook (2001) Molecular Cloning: a laboratory manual, 3rd Edition Cold Spring Harbor Laboratory Press, CSH, New York) or in Volumes 1 and 2 of Ausubel et al. (1994), Current Protocols in Molecular Biology, Current Protocols. Standard materials and methods for plant molecular work are described in Plant Molecular Biology Labfase (1993) by R. D. D. Croy, published by BIOS Scientific Publications Ltd (UK) and Blackwell Scientific Publications (UK).

Example 1

Gene Cloning—Tobacco RNA-Binding Protein-Encoding Gene

A gene encoding an RNA-binding protein was first identified as an expressed sequence tag from Tobacco BY2 cells and was isolated as a partial sequence in a CDNA-AFLP experiment performed with cDNA made from a synchronized tobacco BY2 cell culture (*Nicotiniana tabacum* L. cv. Bright Yellow-2). Based on this cDNA-AFLP experiment, BY2 tags that were cell cycle modulated were identified and selected for further cloning. The expressed sequence tags were used to screen a Tobacco cDNA library and to isolate the full length cDNA.

Synchronization of BY2 Cells

Tobacco BY2 (*Nicotiana tabacum* L. cv. Bright Yellow-2) cultured cell suspension was synchronized by blocking cells in early S-phase with aphidicolin as follows. A cultured cell suspension of *Nicotiana tabacum* L. cv. Bright Yellow 2 was maintained as described (Nagata et al. Int. Rev. Cytol. 132, 1-30, 1992). For synchronization, a 7-day-old stationary culture was diluted 10-fold in fresh medium supplemented with aphidicolin (Sigma-Aldrich, St. Louis, Mo.; 5 mg/l), a DNA-polymerase a inhibiting drug. After 24 h, the cells were released from the block by several washings with fresh medium and they resumed their cell cycle progression.

RNA Extraction and cDNA Synthesis

Total RNA was prepared using LiCl precipitation (Sambrook et al., 2001) and poly($A^+$) RNA was extracted from 500 μg of total RNA using Oligotex columns (Qiagen, Hilden, Germany) according to the manufacturer's instructions. Starting from 1 μg of poly($A^+$) RNA, first-strand cDNA was synthesized by reverse transcription with a biotinylated oligo-$dT_{25}$ primer (Genset, Paris, France) and Superscript II (Life Technologies, Gaithersburg, Md.). Second-strand synthesis was done by strand displacement with *Escherichia coli* ligase (Life Technologies), DNA polymerase I (USB, Cleveland, Ohio) and RNAse-H (USB).

cDNA-AFLP Analysis

Five hundred ng of double-stranded cDNA was used for AFLP analysis as described (Vos et al., Nucleic Acids Res. 23 (21) 4407-4414, 1995; Bachem et al., Plant J. 9 (5) 745-53, 1996) with modifications. The restriction enzymes used were BstYl and Msel (Biolabs) and the digestion was done in two separate steps. After the first restriction digest with one of the enzymes, the 3' end fragments were collected on Dyna beads (Dynal, Oslo, Norway) by means of their biotinylated tail, while the other fragments were washed away. After digestion with the second enzyme, the released restriction fragments were collected and used as templates in the subsequent AFLP steps. For preamplifications, a Msel primer without selective nucleotides was combined with a BstYl primer containing either a T or a C as 3' most nucleotide. PCR conditions were as described (Vos et al., 1995). The obtained amplification mixtures were diluted 600-fold and 5 μl was used for selective amplifications using a $P^{33}$-labeled BstYl primer and the Amplitaq-Gold polymerase (Roche Diagnostics, Brussels, Belgium). Amplification products were separated on 5% polyacrylamide gels using the Sequigel system (Biorad). Dried gels were exposed to Kodak Biomax films as well as scanned in a phospholmager (Amersham Pharmacia Biotech, Little Chalfont, UK).

Characterization of AFLP Fragments

Bands corresponding to differentially expressed transcripts, among which was the transcript corresponding to SEQ ID NO 1, were isolated from the gel and eluted DNA was reamplified under the same conditions as for selective amplification. Sequence information was obtained either by direct sequencing of the reamplified polymerase chain reaction product with the selective BstYl primer or after cloning the fragments in pGEM-T easy (Promega, Madison, Wis.) or by sequencing individual clones. The obtained sequences were compared against nucleotide and protein sequences present in the publicly available databases by BLAST sequence alignments (Altschul et al., Nucleic Acids Res. 25 (17) 3389-3402 1997). When available, tag sequences were replaced with longer EST or isolated cDNA sequences to increase the chance of finding significant homology. The physical cDNA done corresponding to SEQ ID NO 1 was subsequently amplified from a commercial Tobacco cDNA library as follows.

Gene Cloning

A c-DNA library with average inserts of 1,400 by was made with poly($A^+$) isolated from actively dividing, non-synchronized BY2 tobacco cells. These library-inserts were cloned in the vector pCMVSPORT6.0, comprising a attB gateway cassette (Life Technologies). From this library 46,000 clones were selected, arrayed in 384-well microtiter plates, and subsequently spotted in duplicate on nylon filters. The arrayed clones were screened by using pools of several hundreds of radioactively labeled tags as probes (among which was the BY2-tag corresponding to the sequence of SEQ IDNO 1). Positive clones were isolated (among which the clone reacting with the BY2-tag corresponding to the sequence of SEQ ID NO 1), sequenced, and aligned with the tag sequence. In cases where hybridisation with the tag failed, the full-length cDNA corresponding to the tag was selected by PCR amplification as follows. Tag-specific primers were designed using primer3 program genome.wi.mit.edu/genome_software/other/primer3.html) and used in combination with the common vector primer to amplify partial cDNA inserts. Pools of DNA, from 50,000, 100,000, 150,000, and 300,000 cDNA clones were used as templates in PCR amplifications. Amplification products were isolated from agarose gels, cloned, sequenced and aligned with tags.

Subsequently, the full-length cDNA corresponding to SEQ ID NO 1 was cloned from the pCMVsport6.0 library vector into a suitable plant expression vector via an LR Gateway reaction.

LR Gateway Reaction to Clone CDS0701 into a Plant Expression Vector

The pCMV Sport 6.0 p2461 was subsequently used in an LR reaction with a Gateway destination vector suitable for rice transformation. This vector contains as functional elements within the T-DNA borders a plant selectable marker and a Gateway cassette intended for LR in vivo recombination with the sequence of interest already cloned in the donor vector. Upstream of this Gateway cassette is the rice prolamin promoter for seed specific expression of the gene.

After the recombination step, the resulting expression vector (see FIG. 2) was transformed into *Agrobacterium* strain LBA4404 and subsequently into rice plants.

Example 2

Rice Transformation

Mature dry seeds of the rice japonica cultivar Nipponbare (NB) were dehusked. Sterilization was carried out by incubating for one minute in 70% ethanol, followed by 30 minutes in 0.2% HgCl2, followed by a 6×15 minute wash with sterile distilled water. The sterile seeds were then germinated on a medium containing 2,4-D (callus induction medium). After incubation in the dark for four weeks, embryogenic, scutellum-derived calli were excised and propagated on the same medium. After two weeks, the calli were multiplied or propagated by subculture on the same medium for another 2 weeks. Embryogenic callus pieces were sub-cultured on fresh medium 3 days before co-cultivation (to boost cell division activity). *Agrobacterium* strain LBA4404 harbouring binary T-DNA vectors were used for co-cultivation. *Agrobacterium* was inoculated on AB medium with the appropriate antibiotics and cultured for 3 days at 28° C. The bacteria were then collected and suspended in liquid co-cultivation medium to a density (OD600) of about 1. The suspension was then transferred to a petri dish and the calli immersed in the suspension for 15 minutes. The callus tissues were then blotted dry on a filter paper and transferred to solidified, co-cultivation medium and incubated for 3 days in the dark at 25° C. Co-cultivated calli were grown on 2,4-D-containing medium for 4 weeks in the dark at 28° C. in the presence of a suitable concentration of the selective agent. During this period, rapidly growing resistant callus islands developed. After transfer of this material to a regeneration medium and incubation in the light, the embryogenic potential was released and shoots developed in the next four to five weeks. Shoots were excised from the calli and incubated for 2 to 3 weeks on an auxin-containing medium from which they were transferred to soil. Hardened shoots were grown under high humidity and short days in a greenhouse. Seeds were then harvested three to five months after transplanting. The method yielded single locus transformants at a rate of over 50 (Aldemita and Hodges, Planta, 199 612-617, 1996; Chan et al., Plant Mol. Biol. 22 (3) 491-506, 1993, Hiei et al., Plant J., 6 (2) 271-282, 1994).

Example 3

Evaluation and Results

Approximately 15 to 20 independent T0 rice transformants were generated. The primary transformants were transferred from tissue culture chambers to a greenhouse for growing and harvest of T1 seed. 5 events, of which the T1 progeny segregated 3:1 for presence/absence of the transgene, were retained. For each of these events, approximately 10 T1 seedlings containing the transgene (hetero- and homo-zygotes), and in the same number, approximately 10 T1 seedlings lacking the transgene (nullizygotes), were selected by monitoring visual marker expression. 4 T1 events were further evaluated in the T2 generation following the same evaluation procedure as for the T1 generation but with more individuals per event.

Statistical Analysis: F-Test

A two factor ANOVA (analysis of variants) was used as a statistical model for the overall evaluation of plant phenotypic characteristics. An F-test was carried out on all the parameters measured of all the plants of all the events transformed with the gene of the present invention. The F-test was carried out to check for an effect of the gene over all the transformation events and to verify for an overall effect of the gene, also known as a global gene effect. The threshold for significance for a true global gene effect was set at a 5% probability level for the F-test. A significant F-test value points to a gene effect, meaning that it is not only the presence or position of the gene that is causing the differences in phenotype.

3.1 Seed-Related Parameter Measurements

The mature primary panicles were harvested, bagged, barcode-labelled and then dried for three days in the oven at 37° C. The panicles were then threshed and all the seeds were collected and counted. The filled husks were separated from the empty ones using an air-blowing device. The empty husks were discarded and the remaining fraction was counted again. The filled husks were weighed on an analytical balance. The total seed yield was measured by weighing all filled husks harvested from a plant. The harvest index in the present invention is defined as a ratio of total seed yield and the aboveground area ($mm^2$) multiplied by a factor $10^6$.

The Table of results below show the p values from the F test for T1 and T2 evaluations. The percentage difference between the transgenics and the corresponding nullizygotes is also shown. For example, for total seed weight in the T1 generation, 3 out of 4 lines were positive for total seed weight (i.e., showed an increase in total seed weight (of greater than 32%) compared to the seed weight of corresponding nullizygote plants). 2 out of 4 of these lines showed a significant increase in total seed weight with a p value from the F test of 0.061.

TABLE 5

Results of the T1 generation

| T1 | Number of lines showing an increase | Difference | Number of lines showing a significant increase | p value of F test |
|---|---|---|---|---|
| Total weight seeds | 3 out 4 | >32% | 2 out 4 | <0.061 |
| Harvest index | 2 out 4 | >32% | 2 out 4 | <0.09 |

TABLE 6 results of the T2 generation

| T2 | Number of lines showing an increase | Difference | Number of lines showing a significant increase | p value of F test |
|---|---|---|---|---|
| Total weight seeds | 1 out 4 | >30% | 1 out 4 | <0.064 |
| Harvest index | 1 out 4 | >40% | 1 out 4 | <0.001 |

Example 4

Gene Cloning AtRBP1

The *Arabidopsis* AtRBPJ (CDS0078) was amplified by PCR using as template an *Arabidopsis thaliana* seedling cDNA library (Invitrogen, Paisley, UK). After reverse transcription of RNA extracted from seedlings, the cDNAs were cloned into pCMV Sport 6.0. Average insert size of the bank was 1.5 kb, and original number of clones was of $1.59 \times 10^7$ cfu. Original titer was determined to be $9.6 \times 10^5$ cfu/ml, after first amplification of $6 \times 10^{11}$ cfu/ml. After plasmid extraction, 200 ng of template was used in a 50 µl PCR mix. Primers prm00405 (sense 5' ggggacaagtttgtacaaaaaagcag-gcttcacaatggattatgatcggtacaagttat 3', SEQ ID NO: 39) and prm00406 (reverse, complementary: 5' ggggaccactttgtacaa-gaaagctgggtttaaaagagtccaaagaatttcact 3', SEQ ID NO: 40), which include the AttB sites for Gateway recombination, were used for PCR amplification. PCR was performed using Hifi Taq DNA polymerase in standard conditions. A PCR fragment of 1209 by was amplified and purified also using standard methods. The first step of the Gateway procedure, the BP reaction, was then performed, during which the PCR fragment recombines in vivo with the pDONR201 plasmid to produce, according to the Gateway terminology, an "entry clone", p00733. Plasmid pDONR201 was purchased from Invitrogen, as part of the Gateway® technology.

Example 5

Vector Construction AtRBP1

The entry clone p00733 was subsequently used in an LR reaction with p03069, a destination vector used for *Oryza sativa* transformation. This vector contained as functional elements within the T-DNA borders: a plant selectable marker; a visual marker expression cassette; and a Gateway cassette intended for LR in vivo recombination with the sequence of interest already cloned in the entry done. A Beta-Expansin promoter for expression in shoots was located upstream of this Gateway cassette.

After the LR recombination step, the resulting expression vector p04280 (FIG. 2) was transformed into the *Agrobacterium* strain LBA4404 and subsequently to *Oryza sativa* plants. Transformed rice plants were allowed to grow and were then examined for the parameters described in Example 6.

Example 6

Evaluation and Results AtRBP1

Approximately 15 to 20 independent T0 rice transformants were generated. The primary transformants were transferred from tissue culture chambers to a greenhouse for growing and harvest of T1 seed. 5 events, of which the T1 progeny segregated 3:1 for presence/absence of the transgene, were retained. For each of these events, approximately 10 T1 seedlings containing the transgene (hetero- and homo-zygotes), and in the same number, approximately 10 T1 seedlings lacking the transgene (nullizygotes), were selected by monitoring visual marker expression. 4 T1 events were further evaluated in the T2 generation following the same evaluation procedure as for the T1 generation but with more individuals per event. One line that was neutral in the first round was not taken along. In the T2 evaluation, 15T2 seedlings containing the transgene are compared to the same number of plants lacking the transgene (nullizygotes).

Statistical Analysis: F-Test

A two factor ANOVA (analysis of variants) was used as a statistical model for the overall evaluation of plant phenotypic characteristics. An F-test was carried out on all the parameters measured of all the plants of all the events transformed with the gene of the present invention. The F-test was carried out to check for an effect of the gene over all the transformation events and to verify for an overall effect of the gene, also known as a global gene effect. The threshold for significance for a true global gene effect was set at a 5% probability level for the F-test. A significant F-test value points to a gene effect, meaning that it is not only the presence or position of the gene that is causing the differences in phenotype.

6.1 Seed-Related Parameter Measurements

The mature primary panicles were harvested, bagged, barcode-labelled and then dried for three days in the oven at 37° C. The panicles were then threshed and all the seeds were collected and counted. The filled husks were separated from the empty ones using an air-blowing device. The empty husks were discarded and the remaining fraction was counted again. The filled husks were weighed on an analytical balance. This procedure resulted in the set of seed-related parameters described below.

The Table of results below show the p values from the F test for the T1 evaluations, the T2 evaluations and the combined p values from the F tests for the T1 and T2 evaluations. A combined analysis may be considered when two experiments have been carried out on the same events. This may be useful to check for consistency of the effects over the two experiments and to increase confidence in the conclusion. The method used is a mixed-model approach that takes into account the multilevel structure of the data (i.e. experiment—event—segregants). P-values are obtained by comparing likelihood ratio test to chi square distributions. Each of the tables also gives the % difference between the transgenics and the corresponding nullizygotes for each generation.

6.1.1 Aboveground Area

Plant aboveground area was determined by counting the total number of pixels from aboveground plant parts discriminated from the background. This value was averaged for the pictures taken on the same time point from the different angles and was converted to a physical surface value expressed in square mm by calibration. Experiments show that the aboveground plant area measured this way correlates with the biomass of plant parts above ground. The results of the T1 and T2 evaluation are shown in Table 7 below. As shown in the table below, the p value from the F test for the T2 evaluation (p value of 0.0011) and the combined data (with a p value of 0.0287) were significant indicating that the presence of the construct in the plants has a significant positive effect on aboveground area of transgenic plants.

TABLE 7

| Aboveground Area Aboveground area | | |
|---|---|---|
| | % Difference | P value |
| T1 Overall | 8 | 0.1779 |
| T2 Overall | 15 | 0.0011 |
| Combined | | 0.0012 |

6.1.2 Total Seed Yield Per Plant

The total seed yield was measured by weighing all filled husks harvested from a plant. As shown in Table 8 below, the p value from the F test for the T1 and T2 evaluation combined was significant (with a p value of 0.0287) indicating that the presence of the construct in the plants has a significant effect on the total seed weight of transgenic plants.

TABLE 8

| Total Seed Weight | | |
|---|---|---|
| | % Difference | P value |
| T1 | 12 | 0.3397 |
| T2 | 16 | 0.1356 |
| Combined | | 0.0287 |

6.1.3 Total Number of Seeds

As shown in Table 9 below, the p value from the F test for the T1 and T2 evaluation combined (and T2 individually) was significant (with a p value of 0.0006) indicating that the presence of the construct in the plants has a significant effect on the total number of seeds of transgenic plants.

TABLE 9

| Total Number of seeds | | |
|---|---|---|
| | % Difference | P value |
| T1 | 6 | 0.4044 |
| T2 | 23 | 0.0003 |
| Combined | | 0.0006 |

Example 7

GUS Expression Driven by Beta Expansin Promoter

The beta-expansin promoter was cloned into the pDONR201 entry plasmid of the Gateway™ system (Life Technologies) using the "BP recombination reaction". The identity and base pair composition of the cloned insert was confirmed by sequencing and additionally, the resulting plasmid was tested via restriction digests.

In order to clone the promoter in front of a reporter gene, each entry clone was subsequently used in an "LR recombination reaction" (Gateway™) with a destination vector. This destination vector was designed to operably link the promoter to the *Escherichia coli* beta-glucuronidase (GUS) gene via the substitution of the Gateway recombination cassette in front of the GUS gene. The resulting reporter vectors, comprising the promoter operably linked to GUS were subsequently transformed into *Agrobacterium* strain LBA4044 and subsequently into rice plants using standard transformation techniques.

Transgenic rice plants were generated from transformed cells. Plant growth was performed under normal conditions.

The plants or plant parts to be tested were covered with 90% ice-cold acetone and incubated for 30 min at 4° C. After 3 washes of 5 min with Tris buffer [15.76 g Trizma HCl (Sigma T3253)+2.922 g NaCl in 1 litre bi-distilled water, adjusted to pH 7.0 with NaOH], the material was covered by a Tris/ferricyanate/X-Gluc solution [9.8 ml Tris buffer+0.2 ml ferricyanate stock (0.33 g Potassium ferricyanate (Sigma P3667) in 10 ml Tris buffer)+0.2 ml X-Gluc stock (26.1 mg X-Gluc (Europa Bioproducts ML 113A) in 500 µl DMSO)]. Vacuum infiltration was applied for 15 to 30 minutes. The plants or plant parts were incubated for up to 16 hours at 37° C. until development of blue colour was visible. The samples were washed 3 times for 5 minutes with Tris buffer. Chlorophyll was extracted in ethanol series of 50%, 70% and 90% (each for 30 minutes).

The invention claimed is:

1. A method for increasing seed yield and/or biomass in a plant relative to a corresponding wild type plant, comprising transforming a plant with a nucleic acid encoding a polypeptide comprising the amino acid sequence of SEQ ID NO: 2; and
   screening for a plant having increased seed yield and/or biomass on the basis of said plant showing increased seed yield and/or biomass relative to a corresponding wild type plant.

2. The method of claim 1, wherein the nucleic acid is operably linked to a seed-preferred promoter.

3. The method of claim 2, wherein the seed-preferred promoter is a prolamin promoter.

4. The method of claim 1, wherein the nucleic acid is operably linked to a promoter capable of preferentially expressing said nucleic acid in shoots.

5. The method of claim 4, wherein the promoter has a comparable expression profile to a beta-expansin promoter.

6. The method of claim 1, wherein the increased seed yield is selected from any one or more of (i) increased seed biomass; (ii) increased number of (filled) seeds; (iii) increased seed size; (iv) increased seed volume; (v) increased harvest index; and (vi) increased thousand kernel weight (TKW).

7. A plant obtained by the method according to claim 1.

8. A construct comprising:
   (i) a nucleic acid encoding a polypeptide comprising the amino acid sequence of SEQ ID NO: 2;
   (ii) one or more control sequence capable of driving expression of the nucleic acid of (i); and optionally
   (iii) a transcription termination sequence.

9. The construct according to claim 8, wherein said control sequence is a promoter capable of driving expression in seed tissue.

10. The construct according to claim 9, wherein said promoter is a prolamin promoter.

11. A plant transformed with the construct according to claim 8.

12. A method for production of a transgenic plant having increased seed yield and/or biomass relative to a corresponding wild type plant, comprising:
   (i) introducing into a plant a nucleic acid encoding a polypeptide comprising the amino acid sequence of SEQ ID NO: 2;
   (ii) screening for a transgenic plant having increased seed yield and/or biomass on the basis of said plant showing increased seed yield and/or biomass relative to a corresponding wild type plant; and
   (iii) cultivating the transgenic plant under conditions promoting plant growth and development.

13. The plant according to claim 7, wherein said plant is a monocotyledonous plant.

14. A harvestable part of the plant according to claim 7, wherein said harvestable part comprises said nucleic acid.

15. The harvestable part according to claim 14, wherein said harvestable part is a seed.

16. The method of claim 12, wherein the nucleic acid is operably linked to a seed-preferred promoter or a promoter capable of preferentially expressing said nucleic acid in shoots.

17. The method of claim 12, wherein the increased seed yield is selected from any one or more of (i) increased seed biomass; (ii) increased number of (filled) seeds; (iii) increased seed size; (iv) increased seed volume; (v) increased harvest index; and (vi) increased thousand kernel weight (TKW).

18. The method of claim 12, further comprising obtaining a progeny plant from said transgenic plant, wherein said progeny plant comprises said nucleic acid and has increased seed yield and/or biomass relative to a corresponding wild type plant.

19. The method of claim 12, wherein the nucleic acid is operably linked to a prolamin promoter.

20. The method of claim 12, wherein the nucleic acid is operably linked to a promoter having a comparable expression profile to a beta-expansin promoter.

21. A progeny of the plant of claim 7, wherein said progeny comprises the nucleic acid encoding a polypeptide comprising the amino acid sequence of SEQ ID NO: 2 and has increased seed yield and/or biomass relative to a corresponding wild type plant.

22. A progeny of the plant of claim 11, wherein said progeny comprises the construct and has increased seed yield and/or biomass relative to a corresponding wild type plant.

* * * * *

UNITED STATES PATENT AND TRADEMARK OFFICE
CERTIFICATE OF CORRECTION

PATENT NO. : 8,455,719 B2
APPLICATION NO. : 11/660395
DATED : June 4, 2013
INVENTOR(S) : Frankard et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1758 days.

Signed and Sealed this
Eighth Day of September, 2015

Michelle K. Lee
*Director of the United States Patent and Trademark Office*